(12) United States Patent
Blumberg et al.

(10) Patent No.: US 12,110,333 B2
(45) Date of Patent: Oct. 8, 2024

(54) METHODS TO MANIPULATE ALPHA-FETOPROTEIN (AFP)

(71) Applicant: THE BRIGHAM AND WOMEN'S HOSPITAL, INC., Boston, MA (US)

(72) Inventors: Richard S. Blumberg, Waltham, MA (US); Kristi Baker, Edmonton (CA); Michal Pyzik, Cambridge, MA (US); Amit Gandhi, Billerica, MA (US)

(73) Assignee: THE BRIGHAM AND WOMEN'S HOSPITAL, INC.

( * ) Notice: Subject to any disclaimer, the term of this patent is extended or adjusted under 35 U.S.C. 154(b) by 1148 days.

(21) Appl. No.: 16/284,005

(22) Filed: Feb. 25, 2019

(65) Prior Publication Data

US 2020/0010543 A1 Jan. 9, 2020

Related U.S. Application Data

(63) Continuation of application No. 15/306,665, filed as application No. PCT/US2015/026860 on Apr. 21, 2015, now abandoned.

(60) Provisional application No. 62/101,539, filed on Jan. 9, 2015, provisional application No. 61/984,252, filed on Apr. 25, 2014.

(51) Int. Cl.
| | |
|---|---|
| *A61K 39/395* | (2006.01) |
| *A61K 45/06* | (2006.01) |
| *C07K 16/28* | (2006.01) |
| *C07K 16/44* | (2006.01) |

(52) U.S. Cl.
CPC ........ *C07K 16/283* (2013.01); *A61K 39/3955* (2013.01); *A61K 45/06* (2013.01); *C07K 16/44* (2013.01); *C07K 2317/76* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 8,232,067 B2 * | 7/2012 | Blumberg | C07K 14/70535 435/7.1 |
| 2002/0110556 A1 | 8/2002 | Moro | |
| 2012/0107845 A1 * | 5/2012 | Blumberg | C07K 14/76 422/69 |

OTHER PUBLICATIONS

Almagro & Fransson, Frontiers in Bioscience 2008; 13:1619-33 (Year: 2008).*
Padlan (Advances in Protein Chemistry, 1996, 49:57-133) (Year: 1996).*
Corada (Blood, 2001; 97:1679-84) (Year: 2001).*
Berglund et al., Protein Science, 2008, 17:606-613 (Year: 2008).*
Kulkarni-Kale et al. Nucleic Acid Research, 2005, 33:W168-W171 (Year: 2005).*
Li et al., "Alpha-fetoprotein receptor as an early indicator of HBx-driven hepatocarcinogenesis and its applications in tracing cancer cell metastasis", Cancer Lett, 330(2):170-80 (2013).
Mizejewski, "Review of the adenocarcinoma cell surface receptor for human alpha-fetoprotein; proposed identification of a widespread mucin as the tumor cell receptor", Tumour Biol, 34(3):1317-36 (2013).
Posypanova et al., "The receptor binding fragment of alpha-fetoprotein is a promising new vector for the selective delivery of antineoplastic agents", J Drug Target, 21(5):458-65 (2013).
Pyzik "Identification of a novel immunosuppressive FcRn ligand: implications for cancer", Modified May 14, 2012 [Retrieved from the Internet Oct. 24, 2016 http://webapps.cihr-irsc.gc.ca/funding/detail_e?pResearchId=65226533&p_version=CIHR&p_language=E&p_session_id=].
Sand et al., "Dissection of the neonatal Fc receptor (FcRn)-albumin interface using mutagenesis and anti-FcRn albumin-blocking antibodies", J Biol Chem, 289(24):17228-39 (2014).
Baker et al., "Immune and non-immune functions of the (not so) neonatal Fc receptor, FcRn," Semin Immunopathol. 31(2): 223-236 (2009).
Laderoute et al., "The identification, isolation and characterization of a 67 kilodalton, PNA-reactive autoantigen commonly expressed in human adenocarcinomas" Anticancer Res, 14(3B): 1233-45 (1994).
Simister et al., "Isolation and characterization of an Fc receptor from neonatal rat small intestine," Eur J Immunol. 15:733-738 (1985).
Adler et al. "Therapeutic antibodies against cancer." Hematology/Oncology Clinics of North America 26(3): 447-481 (2012).
Moro et al. "Monoclonal antibodies directed against a widespread oncofetal antigen: the alpha-fetoprotein receptor." Tumor Biology 14(2): 116-130 (1993).

(Continued)

*Primary Examiner* — Meera Natarajan
(74) *Attorney, Agent, or Firm* — NIXON PEABODY LLP; David S. Resnick; Mark J. Fitzgerald

(57) ABSTRACT

As demonstrated herein, soluble human FcRn binds to AFP with affinities greater than observed with albumin, and is able to interfere with FcRn-mediated protection of and functional associations with IgG. Accordingly, provided herein, in some aspects, are compositions and methods to inhibit FcRn and AFP interactions in diseases or disorders where elevated AFP levels are associated with immunosuppression. Also provided herein, in some aspects, are compositions and methods to enhance or potentiate FcRn and AFP interactions in diseases or disorders with decreased AFP levels or diseases or disorders where increasing AFP levels increasing with immunosuppression.

19 Claims, 24 Drawing Sheets
Specification includes a Sequence Listing.

(56) References Cited

OTHER PUBLICATIONS

Takahashi et al. "Angiogenesis of AFP producing gastric carcinoma: Correlation with frequent liver metastasis and its inhibition by anti-AFP antibody" Oncology Reports, 11 809-813 (2004).
Ahouse et al., "Mouse MHC class-I like Fc receptor encoded outside the MHC" Journal of Immunology 151: 6076-6088 (1993).
Baker et al. "Neonatal Fc receptors for IgG drive CD8+ T cell-mediated anti-cancer immunosurveillance at tolerogenic mucosal sites." Oncoimmunology 3(2): e27844 pp. 1-3 (2014).
Bitonti et al., "Pulmonary delivery of an erythropoietin Fo fusion protein in non-human primates through an immunoglobulin transport pathway" PNAS 101(26): 9763-9768 (2004).
Burmeister et al., "Crystal structure at 2.2 A resolution of the MHC-related neonatal Fc receptor," Nature 372 (6504): 336-343 (1994).
Burmeister et al., "Crystal structure of the complex of rat neonatal Fo receptor with Fc," Nature 372(6504): 379-383 (1994).
Christianson et al. "Monoclonal antibodies directed against human FcRn and their applications." mAbs 4(2): 208-216 (2012).
Dall'Acqua et al., "Properties of human IgG1s engineered for enhanced binding to the neonatal Fc receptor (FcRn)" Journal of Biological Chemistry 281(33): 23514-23524 (2006).
Firan et al., "The MHC class I-related receptor, FcRn, plays an essential role in the maternofetal transfer of gamma-globulin in humans" International Immunology 13(8): 993-1002 (2001).
Ghetie et al.,"Multiple roles for the major histocompatibility complex class I-related receptor FcRn" Annual Review of Immunology 18: 739-766 (2000).
Ghetie et al., "Transcytosis and catabolismof antibody" Immunologic Research 25(2): 97-113 (2002).
Huber et al., "Crystallization and stoichiometry of binding of a complex between a rat intestinal Fc receptor and Fc" Journal of Molecular Biology 230(3): 1077-1083 (1993).
Huber et al., "Crystallographic structure studies of an IgG molecule and an Fc fragment." Nature 264(5585): 415-420 (1976).
Ingram et al., "Alpha-Fetoprotein and albumin genes are in tandem in the mouse genome" PNAS 78(8): 4694-4698 (1981).
Kacskovics et al., "Cloning and characterization of the bovine MHC class I-like Fc receptor" Journal of Immunology 164: 1889-1897 (2000).
Kandil et al., "The human gene encoding the heavy chain of the major histocompatibility complex class I-like Fc receptor (FCGRT) maps to 19q13.3" Cytogenetics and Cell Genetics 73: 97-98 (1996).
Kim et al., "Localization of the site of the murine IgG1 molecule that is involved in binding to the murine intestinal Fc receptor" European Journal of Immunology 24(10): 2429-2434 (1994).
Kim et al., "Mapping the site on human IgG for binding of the MHC class I-related receptor, FcRn" European Journal of Immunology 29(9): 2819-2825 (1999).
Kuo et al. "Neonatal Fc receptor: from immunity to therapeutics." Journal of Clinical Immunology 30(6): 777-789 (2010).
Kuo et al., "N-Glycan Moieties in Neonatal Fc Receptor Determine Steady-state Membrane Distribution and Directional Transport of IgG" Journal of Biological Chemistry 284(13) 8292-8300 (2009).

Lepercq et al., "Diagnosis and management of intrauterine growth retardation" Hormone Research 49(suppl 2):14-19 (1998).
Martin et al., "Crystal structure at 2.8 A of an FcRn/heterodimeric Fc complex: mechanism of pH-dependent binding" Molecular Cell 7(4): 867-877 (2001).
Medasan et al., "Delineation of the amino acid residues involved in transcytosis and catabolismof mouse IgG1" Journal of Immunology 158(5): 2211-2217 (1997).
Mizejewski. "Review of the putative cell-surface receptors for alpha-fetoprotein: identification of a candidate receptor protein family." Tumor Biology 32(2): 241-258 (2011).
Ober et al., "Differences in promiscuity for antibody-FcRn interactions across species: implications for therapeutic antibodies" International Immunology 13(12): 1551-1559 (2001).
Raghavan et al., "Effects of receptor dimerization on the interaction between the class I major histocompatability complex-related Fc receptor and IgG" PNAS 92: 11200-11204 (1995).
Rooperian et al., "FcRn: the neonatal Fc receptor comes of age" Nature Reviews Immunology 7(9): 715-725 (2007).
Sanchez et al., "Stoichiometry of the interaction between the major histocompatibility complex-related Fc receptor and its Fc ligand" Biochemistry 38(29): 9471-9476 (1999).
Sand et al., "Dissection of the neonatal Fc receptor (FcRn)-albumin interface using mutagenesis and anti-FcRn albumin-blocking antibodies." Journal of Biological Chemistry 289(24): 17228-17239 (2014).
Schuck et al., "Sedimentation equilibrium analysis of recombinant mouse FcRn with murine IgG1" Molecular Immunology 36: 1117-1125 (1999).
Shields et al., "High resolution mapping of the binding site on human IgG1 for Fo gamma RI, Fc gamma RII, Fc gamma RIII, and FcRn and design of IgG1 variants with improved binding to the Fc gamma R" Journal of Biological Chemistry 276(9): 6591-6604 (2001).
Simister et al., "An Fc receptor structurally related to MHC class I antigens" Nature 337(6203): 184-187 (1989).
Sockolosky et al. "Engineering neonatal Fc receptor-mediated recycling and transcytosis in recombinant proteins by short terminal peptide extensions" PNAS 109(4): 16095-16100 (2012).
Story et al., "MHC class I-like Fc receptor cloned from human placenta" Journal of Experimental Medicine 180: 2377-2381 (1994).
Vaughn et al., "Identification of critical IgG binding epitopes on the neonatal Fc receptor" Journal of Molecular Biology 274(4): 597-607 (1997).
Vaughn et al., "Structural basis of pH-dependent antibody binding by the neonatal Fc receptor" Structure 6(1): 63-73 (1998).
West et al., "Crystal structure and immunoglobulin G binding properties of the human major histocompatibility complex-related Fc receptor" Biochemistry 39(32): 9698-9708 (2000).
Zalevsky et al., "Enhanced antibody half-life improves in vivo activity" Nature Biotechnology 28(2): 157-159 (2010).
Zhou et al., "Generation of mutated variants of the human form of the MHC class I-related receptor, FcRn, with increased affinity for mouse immunoglobulin G" Journal of Molecular Biology 332(4): 901-913 (2003).
Masopust et al., 2007, "A brief history of CD8 T cells," Eur. J. Immunol. 37: S103-S110.

* cited by examiner

HSA → ⎧ 466  4 ⎫
       ⎨ EKT[P]VSD ⎬
AFP → ⎩ 491        ⎭
       EMT[P]VNP

```
       416      421      426      431      436      441      446      451      456      461      466
HSA →  PQVSTPTLVEVSRNLGKVGSKCCKHPEAKRMPCAEDYLSVVLNQLCVLHEKTPV
       441      446      451      456      461      466      471      476      481      486      491
AFP →  PQLTSSELMAITRKMAATAATCCQLSEDKLLACGEGAADIIIGHLCIRHEMTPV
```

METHODS TO MANIPULATE ALPHA-FETOPROTEIN (AFP)

CROSS-REFERENCE TO RELATED APPLICATION

This application is a Continuation Application of U.S. Ser. No. 15/306,665 filed on Oct. 25, 2016, which is a 35 U.S.C. § 371 National Phase Entry Application of International Application No. PCT/US15/26860 filed Apr. 21, 2015, and which claims benefit under 35 U.S.C. § 119(e) of U.S. Provisional Application No. 61/984,252 filed Apr. 25, 2014, and U.S. Provisional Application No. 62/101,539 filed Jan. 9, 2015, the contents of each of which are incorporated herein by reference in their entireties.

GOVERNMENT SUPPORT

This invention was made with government support under DK-53056 awarded by the National Institutes of Health (NIH). The government has certain rights in the invention

SEQUENCE LISTING

The instant application contains a Sequence Listing which has been submitted in ASCII format via EFS-Web and is hereby incorporated by reference in its entirety. Said ASCII copy, created on Feb. 22, 2019, is named 043214-081613USC1_SL.txt and is 22,534 bytes in size.

TECHNICAL FIELD

The technical field relates to compositions and methods for modulating alpha-fetoprotein levels and activities.

BACKGROUND

Alpha-fetoprotein (AFP) is a major plasma protein in the fetus, where it is produced by the yolk sac and liver (Ingram et al., 1981). In an adult, its concentration is very low, except when a tumor, such as a hepatoma or teratoma, is present. The alpha-fetoprotein and albumin genes are syntenic, and mammalian AFP and serum albumin genes are believed to have arisen through duplication of an ancestral gene 300 to 500 million years ago.

SUMMARY

The compositions and methods described herein are based, in part, on the discovery that alpha-fetoprotein (AFP) is a third ligand for the neonatal Fc receptor. As demonstrated herein, soluble human FcRn binds to AFP with affinities greater than observed with albumin, and is able to interfere with FcRn-mediated protection of and functional associations with IgG. As further shown herein, the AFP binding site on FcRn overlaps with the albumin binding sites on FcRn, and antibodies that are specific for the albumin site on hFcRn can decrease FcRn-mediated AFP transport. As also demonstrated herein, the binding of FcRn to AFP occurs over a much wider pH range than that observed for IgG and albumin, which typically bind under acidic pH conditions. In addition, provided herein are single nucleotide polymorphisms in AFP that can impact binding of AFP with human FcRn, such as, for example, G109R, R487S, and S445L that increase AFP-FcRn binding, and T451I and D536V, that decrease AFP-FcRn binding.

Accordingly, provided herein, in some aspects, are compositions and methods to inhibit FcRn and AFP interactions in diseases or disorders where elevated AFP levels are associated with immunosuppression. Also provided herein, in some aspects, are compositions and methods to enhance or potentiate FcRn and AFP interactions in diseases or disorders with decreased AFP levels or diseases or disorders where AFP levels increase with immunosuppression.

In some aspects, provided herein are pharmaceutical compositions comprising an inhibitor of AFP-FcRn and a pharmaceutically acceptable carrier, wherein said inhibitor of AFP-FcRn inhibits binding between AFP and FcRn.

In some embodiments of these aspects and all such aspects described herein, the inhibitor of AFP-FcRn comprises a T451I and/or D536V polymorphism of wild-type AFP.

In some embodiments of these aspects and all such aspects described herein, the inhibitor of AFP-FcRn inhibits binding between Y521 and/or V522 of AFP and R42 of FcRn.

In some embodiments of these aspects and all such aspects described herein, the inhibitor of AFP-FcRn inhibits binding between P492 of AFP and R69 of FcRn.

In some embodiments of these aspects and all such aspects described herein, the inhibitor of AFP-FcRn inhibits binding between Q441 and/or V493 of AFP and E44 of FcRn.

In some embodiments of these aspects and all such aspects described herein, the inhibitor of AFP-FcRn inhibits binding between H534 and/or E589 of AFP and N173 of FcRn.

In some embodiments of these aspects and all such aspects described herein, the inhibitor of AFP-FcRn inhibits binding between the hydrophobic core of AFP and FcRn.

In some embodiments of these aspects and all such aspects described herein, the inhibitor of AFP-FcRn inhibits binding between L484, V493, V497, and/or F512 of AFP and V57, W59, and/or W61 of FcRn.

In some embodiments of these aspects and all such aspects described herein, the inhibitor of AFP-FcRn inhibits binding between T443 of AFP and E62 and/or W59 of FcRn.

In some embodiments of these aspects and all such aspects described herein, the inhibitor of AFP-FcRn inhibits binding between D529 of AFP and S230 of FcRn.

In some embodiments of these aspects and all such aspects described herein, the inhibitor of AFP-FcRn inhibits binding between S527 and/or D528 of AFP and E50 and/or 67Y of β2m complexed with FcRn.

In some embodiments of these aspects and all such aspects described herein, the inhibitor of AFP-FcRn inhibits binding between R604 of AFP and the carbonyl oxygen at E50 of β2m complexed with FcRn.

In some embodiments of these aspects and all such aspects described herein, the inhibitor of AFP-FcRn inhibits binding between Q597 of AFP and E69 of β2m complexed with FcRn.

In some embodiments of these aspects and all such aspects described herein, the inhibitor of AFP-FcRn inhibits binding between E106 of AFP and H161 of FcRn.

In some embodiments of these aspects and all such aspects described herein, the inhibitor of AFP-FcRn inhibits binding between S135 of AFP and H161 of FcRn.

In some embodiments of these aspects and all such aspects described herein, the inhibitor of AFP-FcRn inhibits binding between F531, F533, F552, and/or F575 of AFP and W53 of FcRn.

In some embodiments of these aspects and all such aspects described herein, the inhibitor of AFP-FcRn is an antibody or antigen-binding fragment thereof, a small molecule compound, or an RNA or DNA aptamer.

In some embodiments of these aspects and all such aspects described herein, the antibody or antigen-binding fragment thereof is a chimeric, humanized, or completely human antibody or antigen-binding fragment thereof.

In some embodiments of these aspects and all such aspects described herein, the inhibitor of AFP-FcRn inhibits or blocks the AFP binding site on FcRn.

Also provided herein, in some aspects, are pharmaceutical compositions comprising an AFP-FcRn potentiator and a pharmaceutically acceptable carrier.

In some embodiments of these aspects and all such aspects described herein, the AFP-FcRn potentiator comprises a G109R, R487S, and/or S445L polymorphism of wild-type AFP that increases AFP-FcRn binding.

In some embodiments of these aspects and all such aspects described herein, the AFP-FcRn potentiator enhances binding between Y521 and/or V522 of AFP and R42 of FcRn.

In some embodiments of these aspects and all such aspects described herein, the AFP-FcRn potentiator enhances binding between P492 of AFP and R69 of FcRn.

In some embodiments of these aspects and all such aspects described herein, the AFP-FcRn potentiator enhances binding between Q441 and/or V493 of AFP and E44 of FcRn.

In some embodiments of these aspects and all such aspects described herein, the AFP-FcRn potentiator enhances binding between H534 and/or E589 of AFP and N173 of FcRn.

In some embodiments of these aspects and all such aspects described herein, the AFP-FcRn potentiator enhances binding between the hydrophobic core of AFP and FcRn.

In some embodiments of these aspects and all such aspects described herein, the AFP-FcRn potentiator enhances binding between L484, V493, V497, and/or F512 of AFP and V57, W59, and/or W61 of FcRn.

In some embodiments of these aspects and all such aspects described herein, the AFP-FcRn potentiator enhances binding between T443 of AFP and E62 and/or W59 of FcRn.

In some embodiments of these aspects and all such aspects described herein, the AFP-FcRn potentiator enhances binding between D529 of AFP and S230 of FcRn.

In some embodiments of these aspects and all such aspects described herein, the AFP-FcRn potentiator enhances binding between S527 and/or D528 of AFP and E50 and/or 67Y of β2m complexed with FcRn.

In some embodiments of these aspects and all such aspects described herein, the AFP-FcRn potentiator enhances binding between R604 of AFP and the carbonyl oxygen at E50 β2m complexed with FcRn.

In some embodiments of these aspects and all such aspects described herein, the AFP-FcRn potentiator enhances binding between Q597 of AFP and E69 of β2m complexed with FcRn.

In some embodiments of these aspects and all such aspects described herein, the AFP-FcRn potentiator enhances binding between E106 of AFP and H161 of FcRn.

In some embodiments of these aspects and all such aspects described herein, the AFP-FcRn potentiator enhances binding between S135 of AFP and H161 of FcRn.

In some embodiments of these aspects and all such aspects described herein, the AFP-FcRn potentiator enhances binding between 531, F533, F552, and/or F575 of AFP and W53 of FcRn.

In some embodiments of these aspects and all such aspects described herein, the AFP-FcRn potentiator is an antibody or antigen-binding fragment thereof, a small molecule compound, an RNA or DNA aptamer, or an AFP functional fragment.

In some embodiments of these aspects and all such aspects described herein, the antibody or antigen-binding fragment thereof is a chimeric, humanized, or completely human antibody or antigen-binding fragment thereof.

In some embodiments of these aspects and all such aspects described herein, the AFP-FcRn potentiator binds FcRn and mimics AFP binding.

In some embodiments of these aspects and all such aspects described herein, the AFP-FcRn potentiator binds or physically interacts with AFP or FcRn, and enhances or promotes interactions between AFP and FcRn.

In some embodiments of these aspects and all such aspects described herein, the AFP-functional fragment comprises Y521 and/or V522 of AFP and can interact with R42 of FcRn.

In some embodiments of these aspects and all such aspects described herein, the AFP-functional fragment comprises P492 of AFP and can interact with R69 of FcRn.

In some embodiments of these aspects and all such aspects described herein, the AFP-functional fragment comprises Q441 and/or V493 of AFP and can interact with E44 of FcRn.

In some embodiments of these aspects and all such aspects described herein, the AFP-functional fragment comprises H534 and/or E589 of AFP and can interact with N173 of FcRn.

In some embodiments of these aspects and all such aspects described herein, the AFP-functional fragment comprises L484, V493, V497, and/or F512 of AFP and can interact with V57, W59, and/or W61 of FcRn.

In some embodiments of these aspects and all such aspects described herein, the AFP-functional fragment comprises T443 of AFP and can interact with E62 and/or W59 of FcRn.

In some embodiments of these aspects and all such aspects described herein, the AFP-functional fragment comprises D529 of AFP and can interact with S230 of FcRn.

In some embodiments of these aspects and all such aspects described herein, the AFP-functional fragment comprises S527 and/or D528 of AFP and can interact with E50 and/or 67Y of β2m complexed with FcRn.

In some embodiments of these aspects and all such aspects described herein, the AFP-functional fragment comprises R604 of AFP and can interact with the carbonyl oxygen at E50 of β2m complexed with FcRn.

In some embodiments of these aspects and all such aspects described herein, the AFP-functional fragment comprises Q597 of AFP and can interact with E69 of β2m complexed with FcRn.

In some embodiments of these aspects and all such aspects described herein, the AFP-functional fragment comprises E106 of AFP and can interact with H161 of FcRn.

In some embodiments of these aspects and all such aspects described herein, the AFP-functional fragment comprises S135 of AFP and can interact with In some embodiments of these aspects and all such aspects described herein, the AFP-functional fragment comprises F531, F533, F552, and/or F575 of AFP and can interact with W53 of FcRn.

In some embodiments of these aspects and all such aspects described herein, an AFP-functional fragment comprises SEQ ID NO: 4 or AFP (1-575).

In some embodiments of these aspects and all such aspects described herein, an AFP-functional fragment comprises SEQ ID NO: 5 or AFP (484-575).

In some aspects, provided herein are methods to inhibit or reduce FcRn and AFP interactions in a disease or disorder associated with elevated AFP levels comprising administering a therapeutically effective amount of any of the pharmaceutical compositions comprising an AFP-FcRn inhibitor described herein to a subject in need thereof.

In some embodiments of these aspects and all such aspects described herein, the subject has or has been diagnosed with cancer.

In some embodiments of these aspects and all such aspects described herein, the subject has or has been diagnosed with a cancer or tumor of primitive origin, a tumor of liver origin, such as a hepatoma, a tumor of biliary origin, such as cholangiocarcinoma, stomach cancer, pancreatic cancer, or a teratocarcinoma.

In some embodiments of these aspects and all such aspects described herein, the method further comprises administering an anti-cancer therapy or agent to the subject.

In some embodiments of these aspects and all such aspects described herein, the method further comprises administering administering a tumor or cancer antigen.

In some aspects, provided herein are methods to increase or potentiate FcRn and AFP interactions in diseases or disorders associated with decreased AFP levels, or where increasing AFP levels is beneficial, comprising administering a therapeutically effective amount of any of the pharmaceutical compositions comprising an AFP-FcRn potentiator described herein to a subject in need thereof.

In some embodiments of these aspects and all such aspects described herein, the subject in need is pregnant or is at risk for having a problem with establishing and/or maintaining a pregnancy.

In some embodiments of these aspects and all such aspects described herein, the subject has or has been diagnosed with an autoimmune disease or disorder.

In some embodiments of these aspects and all such aspects described herein, the subject has or has been diagnosed with host versus graft disease (HVGD), is an organ or tissue transplant recipient, or a recipient of an allogenic transplant.

Definitions

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, the terms "AFP-FcRn inhibitor" and "alpha fetoprotein and FcRn inhibitor," "inhibitor of AFP-FcRn," or "inhibitor of AFP and FcRn interactions" refer to a molecule or agent that significantly blocks, inhibits, reduces, or interferes with the interaction between AFP and FcRn and their resultant biological or functional activity in vitro, in situ, and/or in vivo, including activity of downstream pathways mediated by AFP binding to FcRn and signaling, such as, for example, transcytosis of AFP, inhibition of T cell stimulation by IgG comprising immune complex-primed dendritic cells, AFP-mediated inhibition of immune responses, and/or increased serum half-life of AFP. Exemplary AFP-FcRn inhibitors contemplated for use in the various aspects and embodiments described herein include, but are not limited to, antibodies or antigen-binding fragments thereof that specifically bind to one or more amino acid residues or epitopes on AFP and/or FcRn involved in the binding and/or interactions of AFP and FcRn, and inhibit/reduce/block AFP and FcRn interactions and/or binding; small molecule agents that target or specifically bind one or more amino acid residues on AFP and/or FcRn involved in the binding and/or interactions of AFP and FcRn, and inhibit/reduce/block AFP and FcRn interactions and/or binding; RNA or DNA aptamers that bind to AFP and/or FcRn and and inhibit/reduce/block AFP and FcRn interactions and/or binding; and/or AFP fragments or fusion polypeptides thereof that block endogenous AFP interactions with FcRn.

"Decreased/decreasing interaction between AFP and FcRn," "reduced/reducing interaction between AFP and FcRn," "inhibits binding," or "inhibited/inhibiting interaction between AFP and FcRn" as used interchangeably herein, generally means either reducing or inhibiting the interaction between or binding of AFP and FcRn by at least 5%, at least 10%, at least 25%, at least 50%, at least 60%, at least 70%, at least 80%, at least 90%, at least 95%, at least 98%, or more, compared to the interaction between AFP and FcRn under the same conditions but without the presence of AFP-FcRn inhibitors described herein. Assays for measuring such inhibition or reduced interactions are known in the art and are described herein in the Examples.

As used herein, the terms "AFP-FcRn potentiator," "potentiator of AFP-FcRn interaction," "AFP-FcRn activator agent," and "AFP-FcRn agonist agent" refer to a molecule or agent that mimics or up-regulates (e.g., increases, potentiates or supplements) the biological activity of AFP binding to FcRn in vitro, in situ, and/or in vivo, including downstream pathways mediated by AFP binding to FcRn and signaling, such as, for example, transcytosis of AFP, inhibition of T cell stimulation by immune complex-primed dendritic cells, AFP-mediated inhibition of immune responses, and/or increased serum half-life of AFP. An AFP-FcRn potentiator or agonist can be, in some embodiments, an AFP protein fragment or derivative thereof having at least one bioactivity of the wild-type AFP. An AFP-FcRn potentiator can also be a compound which increases the interaction of AFP with FcRn, for example. Exemplary AFP-FcRn potentiators or agonists contemplated for use in the various aspects and embodiments described herein include, but are not limited to, antibodies or antigen-binding fragments thereof that specifically bind to AFP bound to FcRn and enhance the interaction and/or block FcRn binding to albumin and/or IgG but allow binding of AFP to FcRn; RNA or DNA aptamers that bind to FcRn and mimic AFP binding to FcRn; AFP structural analogs or AFP fragment, derivatives, or fusion polypeptides thereof; and small molecule agents that target or bind to FcRn and act as functional mimics of AFP binding to FcRn.

As used herein, "antibodies" or "antigen-binding fragments" thereof include monoclonal, human, humanized or chimeric antibodies, single chain antibodies, Fab fragments, F(ab') fragments, fragments produced by a Fab expression library, and/or binding fragments of any of the above. Antibodies also refer to immunoglobulin molecules and immunologically active portions of immunoglobulin molecules, i.e., molecules that contain antigen or target binding sites or "antigen-binding fragments." The immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art.

The terms "antibody fragment" or "antigen-binding fragment" include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) a dAb fragment (Ward et al., Nature 341, 544-546 (1989)) which consists of a $V_H$ domain or a $V_L$ domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$-$C_H1$-$V_H$-$C_H1$) which, together with complementary light chain polypeptides, form a pair of antigen binding regions (Zapata et al. Protein Eng. 8(10):1057-1062 (1995); and U.S. Pat. No. 5,641,870); and modified versions of any of the foregoing (e.g., modified by the covalent attachment of polyalkylene glycol (e.g., polyethylene glycol, polypropylene glycol, polybutylene glycol) or other suitable polymer).

As used herein, an "epitope" can be formed both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein.

As used herein, "small molecule inhibitors" include, but are not limited to, small peptides or peptide-like molecules, soluble peptides, and synthetic non-peptidyl organic or inorganic compounds. A small molecule inhibitor or antagonist can have a molecular weight of any of about 100 to about 20,000 daltons (Da), about 500 to about 15,000 Da, about 1000 to about 10,000 Da.

The term "therapeutically effective amount" therefore refers to an amount of the inhibitors or potentiators described herein, using the methods as disclosed herein, that is sufficient to provide a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign tumors and malignant cancers, as well as dormant tumors or micrometastases. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death.

The term "anti-cancer therapy" refers to a therapy useful in treating cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also specifically contemplated for the methods described herein.

As used herein, the terms "tumor antigen" and "cancer antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER-2, mucins (i.e., MUC-1), prostate-specific antigen (PSA), and prostatic acid phosphatase (PAP). In addition, viral proteins such as hepatitis B (HBV), Epstein-Barr (EBV), and human papilloma (HPV) have been shown to be important in the development of hepatocellular carcinoma, lymphoma, and cervical cancer, respectively. However, due to the immunosuppression of patients diagnosed with cancer, the immune systems of these patients often fail to respond to the tumor antigens.

As used herein, the phrase "at risk for having a problem with establishing and/or maintaining a pregnancy" refers to a subject (e.g., a human) that is predisposed to experiencing a problem with establishing and/or maintaining a pregnancy. This predisposition may be genetic (e.g., a particular genetic tendency to experience a problem with establishing and/or maintaining a pregnancy, such as heritable disorders), or due to other factors (e.g., age, prior experience of a problem with establishing and/or maintaining a pregnancy, drug or alcohol use, environmental conditions, exposures to detrimental compounds present in the environment, etc.). Thus, it is not intended that the present invention be limited to any particular risk, nor is it intended that the present invention be limited to any particular problem with establishing and/or maintaining a pregnancy.

As used herein, an "autoimmune disease" refers to a class of diseases in which a subject's own antibodies react with host tissue or in which immune effector T cells are autoreactive to endogenous self-peptides and cause inflammation and/or destruction of tissue. Thus an immune response is mounted against a subject's own antigens, referred to as self-antigens. A "self-antigen" as used herein refers to an antigen of a normal host tissue. Normal host tissue does not include cancer cells.

DETAILED DESCRIPTION

Figure 1:
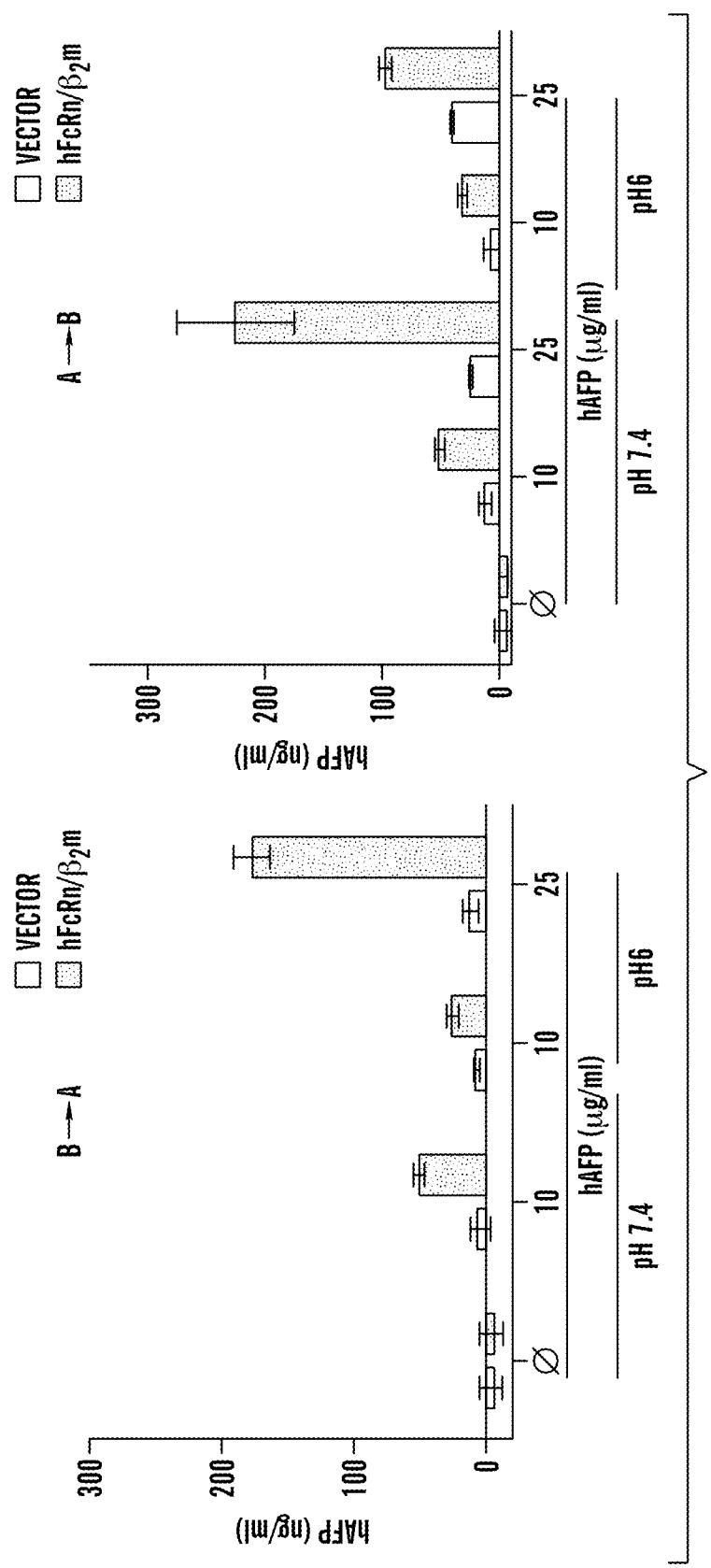
FIG. 1 demonstrates that hAFP is transcytosed by hFcRn at acidic and neutral pH. Transcytosis of human AFP in MDCK II cells co-expressing human FcRn and β2 microglobulin (hFcRn/β2m) or vector control at pH 6 and 7.4. B→A Basolateral to apical direction, A→B Apical to Basolateral direction.

Compositions and methods are provided herein that relate to the discoveries described herein that alpha fetal protein (AFP) is a third ligand for the neonatal Fc receptor or FcRn.
FcRn and Alpha Fetoprotein FcRn, also known as the neonatal Fc receptor, is encoded by the Fcgrt gene. It is a MHC class I-like transmembrane protein consisting of a heavy chain containing three extracellular domains (α1, α2 and α3), a single pass transmembrane domain and a short cytoplasmatic tail (Burmeister et al., 1994a,b; Martin et al., 2001). For proper function, the FcRn heavy chain non-covalently associates with the common β2-microglobulin subunit as a light chain, which interacts with FcRn via residues on the underside of the α1-α2 platform and the side of the α3 domain (West & Bjorkman, 2000). Although the tertiary structure resembles MHC class I molecules with which it shares 22-29% sequence homology (Simister & Mostov, 1989), the mouse and human FcRn genes are located outside the MHC locus, on chromosomes 7 and 19, respectively (Ahouse et al., 1993; Kandil et al., 1996). In further divergence from classical MHC molecules, the sites where peptide residues bind to MHC class I molecules are occluded in FcRn by an arginine side chain and a proline residue, so that FcRn does not present peptide antigens to T-cells (Burmeister et al., 1994a,b).

Most serum proteins have a short serum half-life (about 1-2 days). However, two types of serum proteins, namely albumin and antibodies of the IgG class, have greatly extended serum half-lives. For example, most subclasses of IgG have a half-life of about 10-20 days in humans. The Fc region of IgG is required for this extension of half-life. Thus, truncated IgG polypeptides carrying only the Fc region, and potentially also proteins carrying a short FcRn binding peptide sequence (FcBP) (Sockolosky et al. Proc Natl Acad Sci USA 2012, 109, 16095-100), also show such extended serum half-life. Moreover, when the Fc region is fused with a fusion partner (e.g., a biologically active protein), this Fc fusion protein shows an extended serum half-life due to its interaction with FcRn.

The mechanism by which FcRn extends the serum half-life of IgG and IgG Fc fusion proteins is well established (Ghetie and Ward, 2000, 2002; Roopenian and Akilesh, 2007). FcRn is localized in the endosomal compartments of many cell types, including vascular endothelium. Serum proteins are constantly being endocytosed and directed to the early endosomal vesicles. FcRn is harbored primarily in this acidified vesicle. In this acidified environment, the Fc region binds FcRn, and the IgG/FcRn complex is then recycled either apically or basolaterally back to the plasma membrane, whereupon exposure to the neutral pH 7.2 extracellular environment results in its release into the circulation. In contrast, other endocytosed proteins that do not bind FcRn are not rescued, and thus continue through the endosomal route to catabolic elimination, resulting in their short half-life. The biochemical mechanism by which the Fc region of IgG binds FcRn in an acidic environment is understood. The CH2-CH3-hinge region of the Fc region contains solvent exposed histidine residues, which when protonated, engage residues on FcRn with sufficient affinity to permit IgG to exploit the FcRn recycling pathway to escape catabolic elimination.

Between different species, FcRn exhibits considerable structural variations, which most likely account for the molecule's different ligand binding specificity and slight variations in its functions. The peptide sequences of rat and mouse FcRn, for example, are 91% homologous (Ahouse et al., 1993), whereas the extracellular region of human FcRn shares only 65% amino acid sequence identity with rat FcRn (Story et al., 1994). Bovine FcRn, on the other hand, displays 77% homology to its human counterpart, but exhibits further divergence from rodent FcRn (Kacskovics et al., 2000). Similarly, although mouse and rat FcRn exhibit promiscuous binding to multiple different species of IgG such as horse, rabbit and human, human FcRn binding is significantly more restricted and limited to itself and rabbit (Ober et al., 2001).

Elucidation of the crystal structure revealed that two FcRn molecules bind to a single IgG in a 2:1 stoichiometry (Huber et al., 1993; Sanchez et al., 1999; Schuck et al., 1999). Each IgG heavy chain contains three constant regions (Huber et al., 1976) with one of the FcRn molecules binding to the CH2-CH3 interface of the IgG Fc region (Huber et al., 1993; Sanchez et al., 1999; Schuck et al., 1999; West & Bjorkman, 2000). Such binding between IgG and FcRn occurs in a strictly pH-dependent manner with low micro- to nanomolar affinity at pH<6.5 but no binding at pH 7.5 (Raghavan et al., 1995). Several amino acids on both molecules have been identified to be critical for this interaction. Site-directed mutagenesis approaches have revealed that the residues Ile253, His310 and His435 of IgG play a central role in the interaction with FcRn, as shown within different species (mouse, human and rat) as well as for interspecies binding (Firan et al., 2001; Kim et al., 1994, 1999; Martin et al., 2001; Medesan et al., 1997; Raghavan et al., 1995; Shields et al., 2001). The pKa of His is 6.0-6.5 such that several histidine residues of IgG become protonated below physiologic pH, allowing for the formation of salt bridges with acidic residues on FcRn which in doing so provides the structural basis for the strict pH dependency of IgG-FcRn interactions.

As initially identified in the interaction between rat FcRn and rat IgG2a, residues on FcRn involved in binding IgG include Glu117, Glu118, Glu132, Trp133, Glu135 and Asp137 on the α2 helix (Martin et al., 2001). Although these residues are generally conserved between different species and the main tertiary structure of FcRn with three extracellular ligand-binding domains is preserved, differences between rodent and human FcRn have been described at specific residues and contribute to IgG binding (Vaughn et al., 1997). While human FcRn contains only a single N-glycan moiety in its a2 domain, rat FcRn possesses three additional N-glycan moieties in the α1, α2 and α3 domains (Ahouse et al., 1993; Kuo et al., 2009; Martin et al., 2001; West & Bjorkman, 2000). The Asn128 residue in the α2 domain of rat FcRn, which is lacking in human FcRn, binds to IgG forming a functional "carbohydrate handshake" (Martin et al., 2001; Vaughn & Bjorkman, 1998). In another example, human FcRn displays very limited interspecies IgG binding, extending only to rabbit IgG (Ober et al., 2001), whereas human IgG can bind to cynomolgus FcRn (Bitonti et al., 2004; Dall'Acqua et al., 2006; Zalevsky et al., 2010). Cynomolgus and human IgG have been demonstrated to bind equally well to cynomolgus monkey FcRn (Dall'Acqua et al., 2006), thereby further strengthening the evolutionary significance of the interaction between the Fc region and FcRn. Rodent FcRn, however, is known to be promiscuous by binding to IgG molecules from a variety of species including human, rabbit and bovine IgG as discussed above (Ober et al., 2001). Murinization of human FcRn by mutating the poorly conserved Leu137 residue within the α2 domain of human FcRn to the murine counterpart (glutamic acid) confers binding of human FcRn to mouse IgG1 and IgG2a while reducing binding to human IgG1 twofold (Zhou et al., 2003). The L137E mutation demonstrates that single docking topologies are vitally important in the binding of FcRn to IgG. Apart from the residues discussed above, Ile1 on β2m contributes to IgG binding, most likely by interacting with hydrophobic residues at position 309 of the IgG-Fc domain.

Accordingly, the term "FcRn" as used herein, refers to the molecule comprising the 365 amino acid FcRn large subunit p51 precursor having the amino acid sequence of: MGVPRPQPWALGLLLFLLPGSLGAESHLSLLYHL-TAVSSPAPGTPAFWVSGWLGPQQYLS YNSLRGEAE-PCGAWVWENQVSWYWEKETTDLRIKEKLFLEA-FKALGGKGPYTLQGLLGCE LGPDNTSVPTAKFALN-GEEFMNFDLKQGTWGGDWPEALAISQRWQQQD-KAANKELTFLLF SCPHRLREHLERGRGN-LEWKEPPSMRLKARPSSPGFSVLTCSAFSFYPPELQLR FLRNGL AAGTGQGDFGPNSDGSFHASSSLTVKSGDE-HHYCCIVQHAGLAQPLRVELESPAKSSVLV VGIVIGVLLLTAAAVGGALLWRRMRSGLPAP-WISLRGDDTGVLLPTPGEAQDADLKDVNV IPATA, (SEQ ID NO: 1), as described by, e.g., NP_001129491.1 or NP_004098.1, which non-covalently associates with the β2 microgobulin ("β2m") chain having the amino acid sequence of: MSRSVALAVLALLSLSGLEAIQRTP-KIQVYSRHPAENGKSNFLNCYVSGFHPSDIEVDLL KNGERIEKVEHSDLSFSKDWSFYLLY-YTEFTPTEKDEYACRVNHVTLSQPKIVKWDRDM (SEQ ID NO: 2), as described by, e.g., NP_004039.1, together with any naturally occurring allelic, splice variants, and processed forms thereof. Typically, FcRn refers to human FcRn. The term "FcRn" is also used to refer to truncated forms or fragments of the FcRn polypeptide that retains an FcRn function or activity of interest as described herein, such as, for example, binding to AFP. Reference to any such forms of FcRn can be identified in the application, e.g., by "FcRn (24-110)." Specific residues of FcRn can be referred to as, for example, "FcRn(53) or "W53 of FcRn," or "E69 of β2m of FcRn."

As described herein, the inventors have discovered that a third ligand for FcRn is alpha fetoprotein (AFP). As demonstrated herein, human AFP is transcytosed by FcRn at both acidic and neutral pHs, and increasing amounts of human AFP can inhibit FcRn-mediated transcytosis of IgG, and results in increased IgG clearance from systemic circulation, as well as decreased T cell stimulation by IgG immune complexes.

Alpha-fetoprotein (AFP) is a major plasma protein in the fetus, where it is produced by the yolk sac and liver (Ingram et al., 1981). In an adult, its concentration is very low, except when a tumor, such as a hepatoma or teratoma is present. The alpha-fetoprotein and albumin genes are syntenic, and mammalian AFP and serum albumin genes are believed to have arisen through duplication of an ancestral gene 300 to 500 million years ago. After birth, AFP is down-regulated thousands of fold, such that it is not expressed at high levels in a host under homeostatic conditions. It can become subsequently elevated and expressed at high levels during processes associated with particular types of pathology, such as cancers, particularly in tumors of liver origin (e.g., hepatoma), tumors of the biliary system (e.g., cholangiocarcinoma), and in tumors of primitive origin and that are poorly differentiated, such as teratocarcinomas. In addition, elevated AFP levels can occur during chronic liver inflammatory processes, liver regeneration, and during immune activation, such as allogeneic responses.

Accordingly, the term "AFP" as used herein, refers to the 609 amino acid polypeptide having the amino acid sequence of: MKWVESIFLIFLLNFTESRTLHRNEYGIASILDSYQCTAEISLADLATIFFAQFVQEATY KEVSKMVKDALTAIEKPTGDEQSSGCLENQLPAFLEELCHEKEILEKYGHSDCCSQSEEG RHNCFLAHKKPTPASIPLFQVPEPVTSCEAYEEDRETFMNKFIYEIARRHPFLYAPTILL WAARYDKIIPSCCKAENAVECFQTKAATVTKELRESSLLNQHACAVMKNFGTRTFQAITV TKLSQKFTKVNFTEIQKLVLDVAHVHEHCCRGDVLDCLQDGEKIMSYICSQQDTLSNKIT ECCKLTTLERGQCIIHAENDEKPEGLSPNLNRFLGDRDFNQFSSGEKNIFLASFVHEYSR RHPQLAVSVILRVAKGYQELLEKCFQTENPLECQDKGEEELQKYIQESQALAKRSCGLFQ KLGEYYLQNAFLVAYTKKAPQLTSSELMAITRKMAATAATCCQLSEDKLLACGEGAADII IGHLCIRHEMTPVNPGVGQCCTSSYANRRPCFSSLVVDETYVPPAFSDDKFIFHKDLCQA QGVALQTMKQEFLINLVKQKPQITEEQLEAVIADFSGLLEKCCQGQEQEVCFAEEGQKLI SKIRAALGV (SEQ ID NO: 3), as described by, e.g., NP_001125.1, together with any naturally occurring allelic, splice variants, and processed forms thereof. Typically, AFP refers to human AFP. The term "AFP" can also, in some embodiments, be used to refer to truncated forms or fragments of the AFP polypeptide that retain an AFP function or activity of interest as described herein, such as, for example, binding to FcRn. Reference to any such forms of AFP can be identified in the application, e.g., by "AFP (211-402)." Specific residues of AFP can be referred to as, for example, "AFP(531) or "F531 of AFP."

The discovery as described herein that AFP is a third ligand for FcRn provides novel compositions and methods for the treatment of conditions in which modulating the level of AFP is therapeutic.

Inhibitors and Potentiators of AFP-FcRn Interactions

Provided herein are compositions and methods thereof based, in part, on the discovery that alpha-fetoprotein (AFP) is a third ligand for the neonatal Fc receptor. As demonstrated herein, soluble human FcRn binds to AFP with affinities greater than observed with albumin, and less than that of IgG. As further shown herein, the AFP binding site on FcRn overlaps directly with both the albumin binding sites on FcRn binding sites on FcRn and indirectly with the IgG binding sites mainly through interactions with β2-microglobulin. IgG interactions with FcRn include amino acid contact sites within β2-microglobulin. Antibodies that are specific for the albumin site on hFcRn can decrease FcRn-mediated AFP transport. As also demonstrated herein, the binding of FcRn to AFP occurs over a much wider pH range than that observed for IgG and albumin, which typically bind under acidic pH conditions. In addition, provided herein are single nucleotide polymorphisms in AFP that can impact binding of AFP with human FcRn, such as, for example, G109R, R4875, and S445L that increase AFP-FcRn binding, and T451I and D536V, that decrease AFP-FcRn binding.

Accordingly, provided herein, in some aspects, are compositions and methods to inhibit or reduce FcRn and AFP interactions in diseases or disorders where elevated AFP levels are associated with immunosuppression. Also provided herein, in some aspects, are compositions and methods thereof to enhance or potentiate FcRn and AFP interactions in diseases or disorders with decreased AFP levels or diseases or disorders where increasing AFP levels is therapeutic, such as subjects in need of increasing immunosuppression.

In some aspects, provided herein are compositions, such as pharmaceutical compositions, comprising inhibitors of AFP-FcRn. Such inhibitors are used to inhibit/block the interaction between AFP and FcRn and/or reduce transcytosis of human AFP, and/or reduce serum half-life of AFP. In particular, in some embodiments of the aspects described herein, such AFP-FcRn inhibitors can be used to inhibit or block the AFP binding site on FcRn, which overlaps with the albumin binding sites on FcRn.

In some embodiments of these aspects and all such aspects described herein, an inhibitor of AFP-FcRn comprises a T451I and/or D536V polymorphism of wild-type AFP that decreases AFP-FcRn binding.

In some embodiments of these aspects and all such aspects described herein, an inhibitor of AFP-FcRn inhibits binding and/or interactions between Y521 and/or V522 of AFP and R42 of FcRn.

In some embodiments of these aspects and all such aspects described herein, an inhibitor of AFP-FcRn inhibits binding and/or interactions between P492 of AFP and R69 of FcRn.

In some embodiments of these aspects and all such aspects described herein, an inhibitor of AFP-FcRn inhibits binding and/or interactions between Q441 and/or V493 of AFP and E44 of FcRn.

In some embodiments of these aspects and all such aspects described herein, an inhibitor of AFP-FcRn inhibits binding and/or interactions between H534 and/or E589 of AFP and N173 of FcRn.

In some embodiments of these aspects and all such aspects described herein, an inhibitor of AFP-FcRn inhibits binding between the hydrophobic core of AFP and FcRn. In some such embodiments, an inhibitor of AFP-FcRn inhibits binding and/or interactions between L484, V493, V497, and/or F512 of AFP and V57, W59, and/or W61 of FcRn.

In some embodiments of these aspects and all such aspects described herein, an inhibitor of AFP-FcRn inhibits binding and/or interactions between T443 of AFP and E62 and/or W59 of FcRn.

In some embodiments of these aspects and all such aspects described herein, an inhibitor of AFP-FcRn inhibits binding and/or interactions between D529 of AFP and S230 of FcRn.

In some embodiments of these aspects and all such aspects described herein, an inhibitor of AFP-FcRn inhibits binding between S527 and/or D528 of AFP and E50 and/or 67Y of β2m complexed with FcRn.

In some embodiments of these aspects and all such aspects described herein, an inhibitor of AFP-FcRn inhibits binding between R604 of AFP and the carbonyl oxygen at E50 of β2m complexed with FcRn.

In some embodiments of these aspects and all such aspects described herein, an inhibitor of AFP-FcRn inhibits binding and/or interactions between Q597 of AFP and E69 of β2m complexed with FcRn.

In some embodiments of these aspects and all such aspects described herein, an inhibitor of AFP-FcRn inhibits binding and/or interactions between E106 of AFP and H161 of FcRn.

In some embodiments of these aspects and all such aspects described herein, an inhibitor of AFP-FcRn inhibits binding and/or interactions between S135 of AFP and H161 of FcRn.

In some embodiments of these aspects and all such aspects described herein, an inhibitor of AFP-FcRn inhibits binding and/or interactions between F531, F533, F552, and/or F575 of AFP and W53 of FcRn.

As used herein, the terms "AFP-FcRn inhibitor" and "alpha fetoprotein and FcRn inhibitor," "inhibitor of AFP-FcRn," or "inhibitor of AFP and FcRn interactions" refer to a molecule or agent that significantly blocks, inhibits, reduces, or interferes with the interaction between AFP and FcRn and their resultant biological or functional activity in vitro, in situ, and/or in vivo, including activity of downstream pathways mediated by AFP binding to FcRn and signaling, such as, for example, transcytosis of AFP, inhibition of T cell stimulation by immune complex-primed dendritic cells, AFP-mediated inhibition of immune responses, and/or increased serum half-life of AFP. Exemplary AFP-FcRn inhibitors contemplated for use in the various aspects and embodiments described herein include, but are not limited to, antibodies or antigen-binding fragments thereof that specifically bind to one or more amino acid residues or epitopes on AFP and/or FcRn involved in the binding and/or interactions of AFP and FcRn, and inhibit/reduce/block AFP and FcRn interactions and/or binding; small molecule agents that target or specifically bind one or more amino acid residues on AFP and/or FcRn involved in the binding and/or interactions of AFP and FcRn, and inhibit/reduce/block AFP and FcRn interactions and/or binding; RNA or DNA aptamers that bind to AFP and/or FcRn and inhibit/reduce/block AFP and FcRn interactions and/or binding; and/or AFP fragments or fusion polypeptides thereof that block endogenous AFP interactions with FcRn.

As used herein, an AFP-FcRn inhibitor has the ability to reduce or decrease the interaction between AFP and FcRn and/or their resultant biological or functional activity in vitro, in situ, and/or in vivo by at least 5%, at least 10%, at least 20%, at least 30%, at least 40%, at least 50%, at least 60%, at least 70%, at least 80%, at least 90%, at least 95%, at least 98%, at least 99%, or more, relative to the interaction and/or activity in the absence of the AFP-FcRn inhibitor.

"Decreased/decreasing interaction between AFP and FcRn," "reduced/reducing interaction between AFP and FcRn," "inhibits binding," or "inhibited/inhibiting interaction between AFP and FcRn" as used interchangeably herein, generally means either reducing or inhibiting the interaction between or binding of AFP and FcRn by at least 5%, at least 10%, at least 25%, at least 50%, at least 60%, at least 70%, at least 80%, at least 90%, at least 95%, at least 98%, or more, compared to the interaction between AFP and FcRn under the same conditions but without the presence of AFP-FcRn inhibitors described herein.

In some embodiments of the compositions, methods, and uses described herein, the AFP-FcRn inhibitor is an antibody or antigen-binding fragment thereof. In some embodiments of the aspects described herein, such AFP-FcRn inhibitors can be used to inhibit or block the AFP binding site on FcRn, which overlaps with the albumin binding sites on FcRn, as described herein. In some embodiments, an antibody or antigen-binding fragment inhibitor of AFP-FcRn binds to an epitope that comprises the AFP binding site on FcRn.

In some embodiments of these aspects and all such aspects described herein, the antibody or antigen-binding fragment inhibitor of AFP-FcRn inhibits binding and/or interactions between Y521 and/or V522 of AFP and R42 of FcRn.

In some embodiments of these aspects and all such aspects described herein, the antibody or antigen-binding fragment inhibitor of AFP-FcRn inhibits binding and/or interactions between P492 of AFP and R69 of FcRn.

In some embodiments of these aspects and all such aspects described herein, the antibody or antigen-binding fragment inhibitor of AFP-FcRn inhibits binding and/or interactions between Q441 and/or V493 of AFP and E44 of FcRn.

In some embodiments of these aspects and all such aspects described herein, the antibody or antigen-binding fragment inhibitor of AFP-FcRn inhibits binding and/or interactions between H534 and/or E589 of AFP and N173 of FcRn.

In some embodiments of these aspects and all such aspects described herein, the antibody or antigen-binding fragment inhibitor of AFP-FcRn inhibits binding between the hydrophobic core of AFP and FcRn. In some such embodiments, the antibody or antigen-binding fragment inhibitor of AFP-FcRn inhibits binding and/or interactions between L484, V493, V497, and/or F512 of AFP and V57, W59, and/or W61 of FcRn.

In some embodiments of these aspects and all such aspects described herein, the antibody or antigen-binding fragment inhibitor of AFP-FcRn inhibits binding and/or interactions between T443 of AFP and E62 and/or W59 of FcRn.

In some embodiments of these aspects and all such aspects described herein, the antibody or antigen-binding fragment inhibitor of AFP-FcRn inhibits binding and/or interactions between D529 of AFP and S230 of FcRn.

In some embodiments of these aspects and all such aspects described herein, the antibody or antigen-binding fragment inhibitor of AFP-FcRn inhibits binding between S527 and/or D528 of AFP and E50 and/or 67Y of $\beta 2m$ complexed with FcRn.

In some embodiments of these aspects and all such aspects described herein, the antibody or antigen-binding fragment inhibitor of AFP-FcRninhibits binding between R604 of AFP and the carbonyl oxygen at E50 of $\beta 2m$ complexed with FcRn.

In some embodiments of these aspects and all such aspects described herein, the antibody or antigen-binding fragment inhibitor of AFP-FcRn inhibits binding and/or interactions between Q597 of AFP and E69 of $\beta 2m$ complexed with FcRn.

In some embodiments of these aspects and all such aspects described herein, the antibody or antigen-binding fragment inhibitor of AFP-FcRn inhibits binding and/or interactions between E106 of AFP and H161 of FcRn.

In some embodiments of these aspects and all such aspects described herein, the antibody or antigen-binding fragment inhibitor of AFP-FcRn inhibits binding and/or interactions between S135 of AFP and H161 of FcRn.

In some embodiments of these aspects and all such aspects described herein, the antibody or antigen-binding fragment inhibitor of AFP-FcRn inhibits binding and/or interactions between F531, F533, F552, and/or F575 of AFP and W53 of FcRn.

Antibodies or antigen-binding fragments thereof that are specific for or that selectively bind AFP, FcRn, and/or AFP bound to FcRn, suitable for use in the compositions and for practicing the methods described herein are preferably monoclonal, and can include, but are not limited to, human, humanized or chimeric antibodies, comprising single chain antibodies, Fab fragments, F(ab') fragments, fragments produced by a Fab expression library, and/or binding fragments of any of the above. Antibodies also refer to immunoglobulin molecules and immunologically active portions of immunoglobulin molecules, i.e., molecules that contain antigen or target binding sites or "antigen-binding fragments." The immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art.

Examples of antibody fragments encompassed by the terms antibody fragment or antigen-binding fragment as described herein include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) a dAb fragment (Ward et al., Nature 341, 544-546 (1989)) which consists of a $V_H$ domain or a $V_L$ domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$-$C_H1$-$V_H$-$C_H1$) which, together with complementary light chain polypeptides, form a pair of antigen binding regions (Zapata et al. Protein Eng. 8(10): 1057-1062 (1995); and U.S. Pat. No. 5,641,870); and modified versions of any of the foregoing (e.g., modified by the covalent attachment of polyalkylene glycol (e.g., polyethylene glycol, polypropylene glycol, polybutylene glycol) or other suitable polymer).

With respect to a target or antigen, the term "ligand interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerisation (such as homomerization or heterodimerization) of the target or antigen; or any other site, epitope, antigenic determinant, part, domain or stretch of amino acid residues on the target or antigen that is involved in a biological action or mechanism of the target or antigen, i.e., AFP, FcRn, or AFP bound to FcRn. For example, in some embodiments, a ligand interaction site on FcRn can be any site to which IgG binds or interacts, or any site to which albumin binds or interacts, or any site to which AFP binds or interacts or which when interacting with AFP affects the conformation of the binding sites for albumin and/or IgG within the FcRn/β2-microglobulin heterodimeric complex. More generally, a "ligand interaction site" can be any site, epitope, antigenic determinant, part, domain or stretch of amino acid residues on a target or antigen to which a binding site of an AFP-FcRn inhibitor described herein can bind such that the interaction or binding between AFP and FcRn (and/or any pathway, interaction, signalling, biological mechanism or biological effect mediated by AFP binding to FcRn is involved) is modulated.

In the context of an antibody or antigen-binding fragment thereof, the term "specificity" or "specific for" refers to the number of different types of antigens or antigenic determinants to which a particular antibody or antigen-binding fragment thereof can bind. The specificity of an antibody or antigen-binding fragment or portion thereof can be determined based on affinity and/or avidity. The affinity, represented by the equilibrium constant for the dissociation ($K_D$) of an antigen with an antigen-binding protein, is a measure for the binding strength between an antigenic determinant and an antigen-binding site on the antigen-binding protein: the lesser the value of the $K_D$, the stronger the binding strength between an antigenic determinant and the antigen-binding molecule. Alternatively, the affinity can also be expressed as the affinity constant ($K_A$), which is $1/K_D$). As will be clear to the skilled person, affinity can be determined in a manner known per se, depending on the specific antigen of interest. Accordingly, an antibody or antigen-binding fragment thereof as defined herein is said to be "specific for" a first target or antigen compared to a second target or antigen when it binds to the first antigen with an affinity (as described above, and suitably expressed, for example as a $K_D$ value) that is at least 10 times, such as at least 100 times, and preferably at least 1000 times, and up to 10.000 times or more better than the affinity with which said amino acid sequence or polypeptide binds to another target or polypeptide. Preferably, when an antibody or antigen-binding fragment thereof is "specific for" a target or antigen, compared to another target or antigen, it is directed against said target or antigen, but not directed against another target or antigen.

However, as understood by one of ordinary skill in the art, in some embodiments, where a binding site on a target is shared or partially shared by multiple, different ligands, an antibody or antigen binding fragment thereof can specifically bind to a target, such as FcRn, and have the functional effect of inhibiting/preventing binding of multiple, different ligands, such as AFP, albumin, and/or IgG. For example, as demonstrated herein, the ADM31 antibody inhibits AFP binding to FcRn, as well as binding of albumin to FcRn (Sand, K. M., et B. Dalhus, G. J. Christianson, M. Bern, S. Foss, J. Cameron, D. Sleep, M. Bjoras, D. C. Roopenian, I. Sandlie and J. T. Andersen (2014). "Dissection of the neonatal Fc receptor (FcRn)-albumin interface using mutagenesis and anti-FcRn albumin-blocking antibodies." J Biol Chem 289(24): 17228-17239).

Avidity is the measure of the strength of binding between an antigen-binding molecule and the pertinent antigen. Avidity is related to both the affinity between an antigenic determinant and its antigen binding site on the antigen-binding molecule, and the number of pertinent binding sites present on the antigen-binding molecule. Typically, antigen-binding proteins will bind to their cognate or specific antigen with a dissociation constant ($K_D$ of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ M$^{-1}$) is generally considered to indicate non-specific binding. The $K_D$ for biological interactions which are considered meaningful (e.g., specific) are typically in the range of $10^{-10}$ M (0.1 nM) to $10^{-5}$ M (10000 nM). The stronger an interaction is, the lower is its $K_D$. Preferably, a binding site on a AFP-FcRn inhibitor antibody or antigen-binding fragment thereof described herein will bind to AFP and/or FcRn with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radio-immunoassays (RIA), enzyme immunoassays (EIA) and sandwich competition assays, and the different variants thereof known per se in the art; as well as other techniques as mentioned herein.

In some embodiments of the compositions, methods, and uses described herein, the AFP-FcRn inhibitor is a monoclonal antibody.

The term "monoclonal antibody," as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each antibody in a monoclonal preparation is directed against the same, single determinant on the antigen. It is to be understood that the term "monoclonal antibody" refers to an antibody that is derived from a single clone, including any eukaryotic, prokaryotic, or phage clone, and not the method by which it is produced. The term "monoclonal antibody" as used herein is not limited to antibodies produced through hybridoma technology, and the modifier "monoclonal" is not to be construed as requiring production of the antibody by any particular method. For example, the monoclonal antibodies to be used in accordance with the invention can be made by the hybridoma method first described by Kohler et al., Nature 256:495 (1975), or later adaptations thereof, or can be made by recombinant DNA methods (see, e.g., U.S. Pat. No. 4,816,567). The "monoclonal antibodies" can also be isolated from phage antibody libraries using the techniques described in Clackson et al., Nature 352:624-628 (1991) or Marks et al., J. Mol. Biol. 222:581-597 (1991), for example.

In some embodiments of the compositions, methods, and uses described herein, the AFP-FcRn inhibitor is a chimeric antibody derivative of an antibody or antigen-binding fragment thereof that binds AFP, FcRn, and/or AFP bound to FcRn.

As used herein, the term "chimeric antibody" refers to an antibody molecule in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). Chimeric antibody molecules can include, for example, one or more antigen binding domains from an antibody of a mouse, rat, or other species, with human constant regions. A variety of approaches for making chimeric antibodies have been described and can be used to make chimeric antibodies containing the immunoglobulin variable region which recognizes the desired antigen, e.g., AFP and/or FcRn. See, for example, Takeda et al., 1985, Nature 314:452; Cabilly et al., U.S. Pat. No. 4,816,567; Boss et al.; Tanaguchi et al., European Patent Publication EP171496; European Patent Publication 0173494, United Kingdom patent GB 2177096B).

In some embodiments of the compositions, methods, and uses described herein, the AFP-FcRn inhibitor is a humanized antibody derivative of an antagonist antibody or antigen-binding fragment thereof that binds AFP, FcRn, and/or AFP bound to FcRn.

Humanized forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

In some embodiments of the compositions, methods, and uses comprising any of the AFP-FcRn inhibitor antibodies or antigen-binding fragments thereof described herein, the AFP-FcRn inhibitor antibody or antigen-binding fragment is an antibody derivative. For example, but not by way of limitation, antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids, or alternative scaffolds such as centyrins, DARPINS, or fynomers engineered to bind FcRn and inhibit AFP.

The AFP-FcRn inhibitor antibodies and antigen-binding fragments thereof described herein can be generated by any suitable method known in the art. Monoclonal and polyclonal antibodies against, for example, FcRn, are known in the art. To the extent necessary, e.g., to generate antibodies with particular characteristics or epitope specificity, the skilled artisan can generate new monoclonal or polyclonal AFP-FcRn inhibitor antibodies as briefly discussed herein or as known in the art.

Polyclonal antibodies can be produced by various procedures well known in the art. For example, AFP, FcRn, or fragments thereof comprising one or more of the AFP and/or FcRn interaction sites, can be administered to various host animals including, but not limited to, rabbits, mice, rats, etc. to induce the production of sera containing polyclonal antibodies specific for the protein. Polyclonal antibodies are preferably raised in animals by multiple subcutaneous (sc) or intraperitoneal (ip) injections of the relevant antigen and an adjuvant. It can be useful to conjugate the antigen to a protein that is immunogenic in the species to be immunized, e.g., keyhole limpet hemocyanin, serum albumin, bovine thyroglobulin, or soy-bean trypsin inhibitor using a bifunctional or derivatizing agent, for example, maleimidobenzoyl sulfosuccinimide ester (conjugation through cysteine residues), N-hydroxy-succinimide (through lysine residues), glutaraldehyde, succinic anhydride, $SOCl_2$, or $R^1N=C=NR$, where R and $R^1$ are different alkyl groups. Various other adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Suitable adjuvants are also well known to one of skill in the art.

Monoclonal antibodies can be prepared using a wide variety of techniques known in the art including the use of hybridoma, recombinant, and phage display technologies, or a combination thereof. Various methods for making monoclonal antibodies described herein are available in the art. For example, the monoclonal antibodies can be made using the hybridoma method first described by Kohler et al., Nature, 256:495 (1975), or any later developments thereof, or by recombinant DNA methods (U.S. Pat. No. 4,816,567). For example, monoclonal antibodies can be produced using hybridoma techniques including those known in the art and taught, for example, in Harlow et al., Antibodies: A Laboratory Manual, (Cold Spring Harbor Laboratory Press, 2nd ed., 1988); Hammer-ling, et al., in: Monoclonal Antibodies and T-Cell Hybridomas 563-681 (Elsevier, N.Y., 1981) (said references incorporated by reference in their entireties). Methods for producing and screening for specific antibodies using hybridoma technology are routine and well known in the art. In another example, antibodies useful in the methods and compositions described herein can also be generated using various phage display methods known in the art, such as isolation from antibody phage libraries generated using the techniques described in McCafferty et al., Nature, 348: 552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

In some embodiments of the compositions, methods, and uses described herein, completely human antibodies are used as AFP-FcRn inhibitors, which are particularly desirable for the therapeutic treatment of human patients.

Human antibodies can be made by a variety of methods known in the art, including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741, the contents of which are herein incorporated by reference in their entireties.

Human antibodies can also be produced using transgenic mice which express human immunoglobulin genes, and upon immunization are capable of producing a full repertoire of human antibodies in the absence of endogenous immunoglobulin production. For an overview of this technology for producing human antibodies, see, Lonberg and Huszar, 1995, Int. Rev. Immunol. 13:65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, the contents of which are herein incorporated by reference in their entireties. In addition, companies such as Abgenix, Inc. (Freemont, Calif.) and Medarex (Princeton, N.J.) can be engaged to provide human antibodies directed against a selected antigen using technology similar to that described above. See also, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and Duchosal et al. Nature 355:258 (1992), the contents of which are herein incorporated by reference in their entireties. Alternatively, phage display technology (McCafferty et al., Nature 348:552-553 (1990)) can be used to produce human antibodies and antibody fragments in vitro, from immunoglobulin variable (V) domain gene repertoires from unimmunized donors. Human antibodies can also be generated by in vitro activated B cells (see U.S. Pat. Nos. 5,567,610 and 5,229,275, the contents of which are herein incorporated by reference in their entireties). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1994, Bio/technology 12:899-903).

"An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

As used herein, "antibody variable domain" refers to the portions of the light and heavy chains of antibody molecules that include amino acid sequences of Complementarity Determining Regions (CDRs; i.e., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop. For example, the CDRH1 of the human heavy chain of antibody 4D5 includes amino acids 26 to 35.

"Framework regions" (hereinafter FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

As used herein, a "chimeric antibody" refers to a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science, 1985, 229:1202; Oi et al, 1986, BioTechniques 4:214; Gillies et al., 1989, J. Immunol. Methods 125:191-202; U.S. Pat. Nos. 5,807,715; 4,816,567; and 4,816,397, the contents of which are herein incorporated by reference in their entireties.

"Humanized antibodies," as the term is used herein, refer to antibody molecules from a non-human species, where the antibodies that bind the desired antigen, i.e., AFP, FcRn, and/or AFP bound to FcRn, have one or more CDRs from the non-human species, and framework and constant regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., 1988, Nature 332:323. Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology, 1991, 28(4/5):489-498; Studnicka et al., 1994, Protein Engineering 7(6):805-814; Roguska. et al, 1994, PNAS 91:969-973), and chain shuffling (U.S. Pat. No. 5,565,332), the contents of which are herein incorporated by reference in their entireties. Accordingly, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), the contents of which are herein incorporated by reference in their entireties, by substituting rodent CDRs or CDR sequences for the corresponding sequences of a human antibody. Accordingly, such "humanized" antibodies are chimeric antibodies (U.S. Pat. No. 4,816,567, the contents of which are herein incorporated by reference in its entirety) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The "Fab" fragment contains a variable and constant domain of the light chain and a variable domain and the first constant domain ($C_H1$) of the heavy chain. $F(ab')_2$ antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

The expression "linear antibodies" refers to the antibodies described in Zapata et al., Protein Eng., 8(10):1057-1062

(1995). Briefly, these antibodies comprise a pair of tandem Fd segments ($V_H$-$C_H1$-$V_H$-$C_H1$) which, together with complementary light chain polypeptides, form a pair of antigen binding regions. Linear antibodies can be bispecific or monospecific.

Various techniques have been developed for the production of antibody or antigen-binding fragments. The antibodies described herein can be fragmented using conventional techniques and the fragments screened for utility in the same manner as described above for the whole antibodies. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). For example, Fab and F(ab')$_2$ fragments of the bispecific and multispecific antibodies described herein can be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the $C_H1$ domain of the heavy chain. However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

Examples of techniques which can be used to produce single-chain Fvs and antibodies include those described in U.S. Pat. Nos. 4,946,778 and 5,258,498; Huston et al., 1991, Methods in Enzymology 203:46-88; Shu et al., 1993, PNAS 90:7995-7999; and Skerra et al., 1988, Science 240:1038-1040. For some uses, including the in vivo use of antibodies in humans as described herein and in vitro proliferation or cytotoxicity assays, it is preferable to use chimeric, humanized, or human antibodies.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by $V_H$ and $V_L$ domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al., J. Mol. Biol. 226:889-896 (1992).

As used herein "complementary" refers to when two immunoglobulin domains belong to families of structures which form cognate pairs or groups or are derived from such families and retain this feature. For example, a $V_H$ domain and a $V_L$ domain of a natural antibody are complementary; two $V_H$ domains are not complementary, and two $V_L$ domains are not complementary. Complementary domains can be found in other members of the immunoglobulin superfamily, such as the $V_\alpha$ and $V_\beta$ (or γ and δ) domains of the T-cell receptor. Domains which are artificial, such as domains based on protein scaffolds which do not bind epitopes unless engineered to do so, are non-complementary. Likewise, two domains based on, for example, an immunoglobulin domain and a fibronectin domain are not complementary.

In some embodiments of the compositions, methods, and uses described herein, the AFP-FcRn inhibitor is a small molecule inhibitor, agent, or compound. In some embodiments of the aspects described herein, such AFP-FcRn small molecule inhibitors or small molecule inhibitors of AFP-FcRn can be used to inhibit or block the AFP binding site on FcRn, which overlaps with the albumin and IgG binding activities on FcRn, as described herein.

Such small molecule inhibitors include, but are not limited to, small peptides or peptide-like molecules, soluble peptides, and synthetic non-peptidyl organic or inorganic compounds. A small molecule inhibitor or antagonist can have a molecular weight of any of about 100 to about 20,000 daltons (Da), about 500 to about 15,000 Da, about 1000 to about 10,000 Da.

In some embodiments of these aspects and all such aspects described herein, the small molecule inhibitor of AFP-FcRn inhibits binding and/or interactions between Y521 and/or V522 of AFP and R42 of FcRn.

In some embodiments of these aspects and all such aspects described herein, the small molecule inhibitor of AFP-FcRn inhibits binding and/or interactions between P492 of AFP and R69 of FcRn.

In some embodiments of these aspects and all such aspects described herein, the small molecule inhibitor of AFP-FcRn inhibits binding and/or interactions between Q441 and/or V493 of AFP and E44 of FcRn.

In some embodiments of these aspects and all such aspects described herein, the small molecule inhibitor of AFP-FcRn inhibits binding and/or interactions between H534 and/or E589 of AFP and N173 of FcRn.

In some embodiments of these aspects and all such aspects described herein, the small molecule inhibitor of AFP-FcRn inhibits binding between the hydrophobic core of AFP and FcRn. In some such embodiments, the small molecule inhibitor of AFP-FcRn inhibits binding and/or interactions between L484, V493, V497, and/or F512 of AFP and V57, W59, and/or W61 of FcRn.

In some embodiments of these aspects and all such aspects described herein, the small molecule inhibitor of AFP-FcRn inhibits binding and/or interactions between T443 of AFP and E62 and/or W59 of FcRn.

In some embodiments of these aspects and all such aspects described herein, the small molecule inhibitor of AFP-FcRn inhibits binding and/or interactions between D529 of AFP and S230 of FcRn.

In some embodiments of these aspects and all such aspects described herein, the small molecule inhibitor of AFP-FcRn inhibits binding between S527 and/or D528 of AFP and E50 and/or 67Y of β2m complexed with FcRn.

In some embodiments of these aspects and all such aspects described herein, the small molecule inhibitor of AFP-FcRn inhibits binding between R604 of AFP and the carbonyl oxygen at E50 of β2m complexed with FcRn.

In some embodiments of these aspects and all such aspects described herein, the small molecule inhibitor of AFP-FcRn inhibits binding and/or interactions between Q597 of AFP and E69 of β2m complexed with FcRn.

In some embodiments of these aspects and all such aspects described herein the small molecule inhibitor of AFP-FcRn inhibits binding and/or interactions between E106 of AFP and H161 of FcRn.

In some embodiments of these aspects and all such aspects described herein, the small molecule inhibitor of AFP-FcRn inhibits binding and/or interactions between S135 of AFP and H161 of FcRn.

In some embodiments of these aspects and all such aspects described herein, the small molecule inhibitor of AFP-FcRn inhibits binding and/or interactions between F531, F533, F552, and/or F575 of AFP and W53 of FcRn.

In some embodiments of the compositions, methods, and uses described herein, an AFP-FcRn inhibitor is an RNA or DNA aptamer that binds or physically interacts with AFP, and blocks interactions between AFP and FcRn. In some embodiments of the compositions, methods, and uses described herein, an AFP-FcRn inhibitor is an RNA or DNA aptamer that binds or physically interacts with FcRn, and blocks interactions between AFP and FcRn. In some embodiments of the cocompositions, methods, and uses described herein, the aptamer comprises at least one RNA or DNA aptamer that binds to the FcRn large subunit p51 heavy chain precursor of FcRn. In some embodiments of the compositions, methods, and uses described herein, the aptamer comprises at least one RNA or DNA aptamer that binds to the β2m subunit of FcRn.

In some embodiments of these aspects and all such aspects described herein, the the RNA or DNA aptamer inhibitor of AFP-FcRn inhibits binding and/or interactions between Y521 and/or V522 of AFP and R42 of FcRn.

In some embodiments of these aspects and all such aspects described herein, the RNA or DNA aptamer inhibitor of AFP-FcRn inhibits binding and/or interactions between P492 of AFP and R69 of FcRn.

In some embodiments of these aspects and all such aspects described herein, the RNA or DNA aptamer inhibitor of AFP-FcRn inhibits binding and/or interactions between Q441 and/or V493 of AFP and E44 of FcRn.

In some embodiments of these aspects and all such aspects described herein, the RNA or DNA aptamer inhibitor of AFP-FcRn inhibits binding and/or interactions between H534 and/or E589 of AFP and N173 of FcRn.

In some embodiments of these aspects and all such aspects described herein, the RNA or DNA aptamer inhibitor of AFP-FcRn inhibits binding between the hydrophobic core of AFP and FcRn. In some such embodiments, the RNA or DNA aptamer inhibitor of AFP-FcRn inhibits binding and/or interactions between L484, V493, V497, and/or F512 of AFP and V57, W59, and/or W61 of FcRn.

In some embodiments of these aspects and all such aspects described herein, the RNA or DNA aptamer inhibitor of AFP-FcRn inhibits binding and/or interactions between T443 of AFP and E62 and/or W59 of FcRn.

In some embodiments of these aspects and all such aspects described herein, the RNA or DNA aptamer inhibitor of AFP-FcRn inhibits binding and/or interactions between D529 of AFP and S230 of FcRn.

In some embodiments of these aspects and all such aspects described herein, the RNA or DNA aptamer inhibitor of AFP-FcRn inhibits binding between S527 and/or D528 of AFP and E50 and/or 67Y of β2m complexed with FcRn.

In some embodiments of these aspects and all such aspects described herein, the RNA or DNA aptamer inhibitor of AFP-FcRn inhibits binding between R604 of AFP and the carbonyl oxygen at E50 of β2m complexed with FcRn.

In some embodiments of these aspects and all such aspects described herein, the RNA or DNA aptamer inhibitor of AFP-FcRn inhibits binding and/or interactions between Q597 of AFP and E69 of β2m complexed with FcRn.

In some embodiments of these aspects and all such aspects described herein the RNA or DNA aptamer inhibitor of AFP-FcRn inhibits binding and/or interactions between E106 of AFP and H161 of FcRn.

In some embodiments of these aspects and all such aspects described herein, the RNA or DNA aptamer inhibitor of AFP-FcRn inhibits binding and/or interactions between S135 of AFP and H161 of FcRn.

In some embodiments of these aspects and all such aspects described herein, the RNA or DNA aptamer inhibitor of AFP-FcRn inhibits binding and/or interactions between F531, F533, F552, and/or F575 of AFP and W53 of FcRn.

AFP-FcRn inhibitors for use in the compositions, methods, and uses described herein can be identified or characterized using methods known in the art, such as protein-protein binding assays, biochemical screening assays, immunoassays, and cell-based assays, which are well known in the art, including, but not limited to, those described herein in the Examples and Figures.

For example, to identify a molecule that inhibits interaction between AFP and FcRn, transcytosis assays can be used, as described herein. For example, cells, such as MDCK II cells, that co-express human FcRn and β2m, can be tested for basolateral to apical transcytosis of AFP in the presence of a putative AFP-FcRn inhibitor (i.e., a test agent) and a control agent. If AFP transcytosis is inhibited by the presence of the test agent, relative to the transcytosis in the presence of the control agent, the test agent can be deemed a candidate inhibitor that inhibits binding between AFP and FcRn. Additional assays, such as, for example, Biacore assays, can be used to further determine whether and how a candidate agent inhibits binding between FcRn and AFP.

Also provided herein, in some aspects, are compositions, such as pharmaceutical compositions, comprising potentiators of AFP-FcRn interactions. Such potentiators are used to enhance/increase/potentiate the interaction between AFP and FcRn and/or increase transcytosis of human AFP, and/or increase serum half-life of AFP, thereby increasing immunosuppressive activities of AFP in the treatment of disorders and conditions in need of enhanced AFP levels, including autoimmune disorders, transplant patients, and high-risk pregnancies, for example.

As used herein, the terms "AFP-FcRn potentiator," "potentiator of AFP-FcRn interaction," AFP-FcRn activator agent," and "AFP-FcRn agonist agent" refer to a molecule or agent that mimics or up-regulates (e.g., increases, potentiates or supplements) the biological activity of AFP binding to FcRn in vitro, in situ, and/or in vivo, including downstream pathways mediated by AFP binding to FcRn and signaling, such as, for example, transcytosis of AFP, inhibition of T cell stimulation by immune complex-primed dendritic cells, AFP-mediated inhibition of immune responses, and/or increased serum half-life of AFP. An AFP-FcRn potentiator or agonist can be, in some embodiments, an AFP protein fragment or derivative thereof having at least one bioactivity of the wild-type AFP. An AFP-FcRn potentiator can also be a compound which increases the interaction of AFP with FcRn, for example. Exemplary AFP-FcRn potentiators or agonists contemplated for use in the various aspects and embodiments described herein include, but are not limited to, antibodies or antigen-binding fragments thereof that specifically bind to AFP bound to FcRn and enhance the interaction and/or block FcRn binding to albumin and/or IgG but allow binding of AFP to FcRn; RNA or DNA aptamers that bind to FcRn and mimic AFP binding to FcRn; AFP structural analogs or AFP functional fragments, derivatives, or fusion polypeptides thereof; and small molecule agents that target or bind to FcRn and act as functional mimics of AFP binding to FcRn.

As used herein, an AFP-FcRn potentiator has the ability to increase or enhance the activity of AFP binding to FcRn or mimic/replicate the downstream functional consequences mediated by AFP binding to FcRn by at least 5%, at least 10%, at least 20%, at least 30%, at least 40%, at least 50%, at least 60%, at least 70%, at least 80%, at least 90%, at least 95%, at least 98%, at least 99%, at least 100%, at least 1.5-fold, at least 2-fold, at least 5-fold, at least 10-fold, at least 25-fold, at least 50-fold, at least 100-fold, at least 1000-fold, or more relative to the activity or expression level in the absence of the AFP-FcRn potentiator.

In some embodiments of these aspects and all such aspects described herein, an AFP-FcRn potentiator comprises a G109R, R487S, and/or S445L polymorphism of wild-type AFP that increases AFP-FcRn binding.

In some embodiments of these aspects and all such aspects described herein, an AFP-FcRn potentiator enhances binding and/or interactions between Y521 and/or V522 of AFP and R42 of FcRn.

In some embodiments of these aspects and all such aspects described herein, an AFP-FcRn potentiator enhances binding and/or interactions between P492 of AFP and R69 of FcRn.

In some embodiments of these aspects and all such aspects described herein, an AFP-FcRn potentiator enhances binding and/or interactions between Q441 and/or V493 of AFP and E44 of FcRn.

In some embodiments of these aspects and all such aspects described herein, an AFP-FcRn potentiator enhances binding and/or interactions between H534 and/or E589 of AFP and N173 of FcRn.

In some embodiments of these aspects and all such aspects described herein, an AFP-FcRn potentiator enhances binding between the hydrophobic core of AFP and FcRn. In some such embodiments, an AFP-FcRn potentiator enhances binding and/or interactions between L484, V493, V497, and/or F512 of AFP and V57, W59, and/or W61 of FcRn.

In some embodiments of these aspects and all such aspects described herein, an AFP-FcRn potentiator enhances binding and/or interactions between T443 of AFP and E62 and/or W59 of FcRn.

In some embodiments of these aspects and all such aspects described herein, an AFP-FcRn potentiator enhances binding and/or interactions between D529 of AFP and S230 of FcRn.

In some embodiments of these aspects and all such aspects described herein, an AFP-FcRn potentiator enhances binding between S527 and/or D528 of AFP and E50 and/or 67Y of β2m complexed with FcRn.

In some embodiments of these aspects and all such aspects described herein, an AFP-FcRn potentiator enhances binding between R604 of AFP and the carbonyl oxygen at E50 of β2m complexed with FcRn.

In some embodiments of these aspects and all such aspects described herein, an AFP-FcRn potentiator enhances binding and/or interactions between Q597 of AFP and E69 of β2m complexed with FcRn.

In some embodiments of these aspects and all such aspects described herein, an AFP-FcRn potentiator enhances binding and/or interactions between E106 of AFP and H161 of FcRn.

In some embodiments of these aspects and all such aspects described herein, an AFP-FcRn potentiator enhances binding and/or interactions between S135 of AFP and H161 of FcRn.

In some embodiments of these aspects and all such aspects described herein, an AFP-FcRn potentiator enhances binding and/or interactions between F531, F533, F552, and/or F575 of AFP and W53 of FcRn.

In some embodiments of the compositions, methods, and uses described herein, the AFP-FcRn potentiator is an antibody or antigen-binding fragment thereof that selectively binds or physically interacts with AFP bound to FcRn and enhances the interaction of AFP and FcRn, and/or blocks FcRn binding to albumin and/or IgG but allows binding of AFP to FcRn, thereby resulting in increased transcytosis of AFP, increased inhibition of T cell stimulation by immune complex-primed dendritic cells, increased AFP-mediated inhibition of immune responses, and/or increased serum half-life of AFP. Exemplary assays to measure increases or up-regulation of downstream pathway activities are known to those of ordinary skill in the art and are provided herein in the Examples.

In some embodiments of the compositions, methods, and uses described herein, an AFP-FcRn potentiator is a monoclonal antibody. In some embodiments of the compositions, methods, and uses described herein, an AFP-FcRn potentiator is an antibody fragment or antigen-binding fragment, as the term is described elsewhere herein.

In some embodiments of the compositions, methods, and uses described herein, an AFP-FcRn potentiator is a chimeric antibody derivative of the AFP-FcRn potentiator antibodies and antigen-binding fragments thereof, as the term is described elsewhere herein.

In some embodiments of the compositions, methods, and uses described herein, an AFP-FcRn potentiator is a humanized antibody derivative, as the term is described elsewhere herein.

In some embodiments, the AFP-FcRn potentiator antibodies and antigen-binding fragments thereof described herein include derivatives that are modified, i.e., by the covalent attachment of any type of molecule to the antibody, provided that covalent attachment does not prevent the antibody from binding to the target antigen.

In some embodiments, the AFP-FcRn potentiator antibodies and antigen-binding fragments thereof described herein are completely human antibodies or antigen-binding fragments thereof, which are particularly desirable for the therapeutic treatment of human patients. Human antibodies can be made by a variety of methods known in the art, and as described in more detail elsewhere herein.

The AFP-FcRn potentiator antibodies and antigen-binding fragments thereof described herein, as well as any of the other antibodies or antigen-binding fragments thereof described herein in various aspects and embodiments, can be generated by any suitable method known in the art.

In some embodiments of the compositions, methods, and uses described herein, the AFP-FcRn potentiator is a small molecule potentiator, activator, or agonist, including, but not limited to, small peptides or peptide-like molecules, soluble peptides, and synthetic non-peptidyl organic or inorganic compounds. A small molecule activator or agonist can have a molecular weight of any of about 100 to about 20,000 daltons (Da), about 500 to about 15,000 Da, about 1000 to about 10,000 Da. In some embodiments of the compositions, methods, and uses described herein, an AFP-FcRn potentiator comprises a small molecule that binds FcRn and mimics AFP binding. Exemplary sites of small molecule binding include, but are not limited to, the portion of FcRn that binds specifically to AFP, or to the portions of FcRn adjacent to the AFP binding site.

In some embodiments of the compositions, methods, and uses described herein, an AFP-FcRn potentiator is an RNA or DNA aptamer that binds or physically interacts with AFP or FcRn, and enhances or promotes interactions between AFP and FcRn.

In some embodiments of the compositions, methods, and uses described herein, an AFP-FcRn potentiator comprises an AFP structural analog, functional fragment, or derivative, such as an AFP variant engineered to possess increased binding to the FcRn/β2-microglobulin complex. The term "AFP structural analog," "AFP functional fragment," or "AFP derivative" as used herein, refer to compounds, such as peptides, that can bind to FcRn under physiological conditions in vitro or in vivo, wherein the binding at least partially mimics or increases an FcRn mediated biological activity. Suitable AFP structural analogs, functional fragments, or derivatives can be designed and synthesized through molecular modeling of AFP binding to FcRn, for example.

In some embodiments of these aspects and all such aspects described herein, an AFP-functional fragment comprises Y521 and/or V522 of AFP and can interact with R42 of FcRn.

In some embodiments of these aspects and all such aspects described herein, an AFP-functional fragment comprises P492 of AFP and can interact with R69 of FcRn.

In some embodiments of these aspects and all such aspects described herein, an AFP-functional fragment comprises Q441 and/or V493 of AFP and can interact with E44 of FcRn.

In some embodiments of these aspects and all such aspects described herein, an AFP-functional fragment comprises H534 and/or E589 of AFP and can interact with N173 of FcRn.

In some embodiments of these aspects and all such aspects described herein, an AFP-functional fragment comprises L484, V493, V497, and/or F512 of AFP and can interact with V57, W59, and/or W61 of FcRn.

In some embodiments of these aspects and all such aspects described herein, an AFP-functional fragment comprises T443 of AFP and can interact with E62 and/or W59 of FcRn.

In some embodiments of these aspects and all such aspects described herein, an AFP-functional fragment comprises D529 of AFP and can interact with S230 of FcRn.

In some embodiments of these aspects and all such aspects described herein, an AFP-functional fragment comprises S527 and/or D528 of AFP and can interact with E50 and/or 67Y of β2m complexed with FcRn.

In some embodiments of these aspects and all such aspects described herein, an AFP-functional fragment comprises R604 of AFP and can interact with the carbonyl oxygen at E50 of β2m complexed with FcRn.

In some embodiments of these aspects and all such aspects described herein, an AFP-functional fragment comprises Q597 of AFP and can interact with E69 of β2m complexed with FcRn.

In some embodiments of these aspects and all such aspects described herein, an AFP-functional fragment comprises E106 of AFP and can interact with H161 of FcRn.

In some embodiments of these aspects and all such aspects described herein, an AFP-functional fragment comprises S135 of AFP and can interact with H161 of FcRn.

In some embodiments of these aspects and all such aspects described herein, an AFP-functional fragment comprises F531, F533, F552, and/or F575 of AFP and can interact with W53 of FcRn.

In some embodiments of these aspects and all such aspects described herein, an AFP-functional fragment comprises

```
                                              (SEQ ID NO: 4)
MKWVESIFLIFLLNFTESRTLHRNEYGIASILDSYQCTAEISLADLATIF

FAQFVQEATYKEVSKMVKDALTAIEKPTGDEQSSGCLENQLPAFLEELCH

EKEILEKYGHSDCCSQSEEGRHNCFLAHKKPTPASIPLFQVPEPVTSCEA

YEEDRETFMNKFIYEIARRHPFLYAPTILLWAARYDKIIPSCCKAENAVE

CFQTKAATVTKELRESSLLNQHACAVMKNFGTRTFQAITVTKLSQKFTKV

NFTEIQKLVLDVAHVHEHCCRGDVLDCLQDGEKIMSYICSQQDTLSNKIT

ECCKLTTLERGQCIIHAENDEKPEGLSPNLNRFLGDRDFNQFSSGEKNIF

LASFVHEYSRRHPQLAVSVILRVAKGYQELLEKCFQTENPLECQDKGEEE

LQKYIQESQALAKRSCGLFQKLGEYYLQNAFLVAYTKKAPQLTSSELMAI

TRKMAATAATCCQLSEDKLLACGEGAADIIIGHLCIRHEMTPVNPGVGQC

CTSSYANRRPCFSSLVVDETYVPPAFSDDKFIFHKDLCQAQGVALQTMKQ

EFLINLVKQKPQITEEQLEAVIADF
or

AFP (1-575).
```

In some embodiments of these aspects and all such aspects described herein, an AFP-functional fragment comprises

```
                                              (SEQ ID NO: 5)
LCIRHEMTPVNPGVGQCCTSSYANRRPCFSSLVVDETYVPPAFSDDKFIF

HKDLCQAQGVALQTMKQEFLINLVKQKPQITEEQLEAVIADF
or

AFP (484-575).
```

The term "AFP functional fragment," as used herein, refers to a fragment of AFP that specifically binds to FcRn and can be transcytosed across a cell membrane, and can, in some embodiments, increase serum half-life of a protein to which it is fused or conjugated. Accordingly, the term "functional" when used in conjunction with a fragment, "derivative" or "variant" refers to a protein molecule that possesses a desired biological activity that is substantially similar to a biological activity of the entity or molecule of which it is a fragment, derivative or variant. By "substantially similar" in this context is meant that the biological activity, e.g., specifically bind to FcRn and be transcytosed across a cell membrane, and can, in some embodiments, increase serum half-life of a protein to which it is fused or conjugated, is at least 50% as active as a reference, e.g., a corresponding wild-type or endogenous AFP, and preferably at least 60% as active, 70% as active, 80% as active, 90% as active, 95% as active, 100% as active or even higher (i.e., the variant or derivative has greater activity than the wild-type), e.g., 110% as active, 120% as active, or more. Assays to measure the biological activity of an AFP functional fragment are known in the art, and non-limiting examples are provided herein in the Examples.

In some embodiments of these aspects and all such aspects described herein, an AFP-functional fragment differs from endogenous AFP by one or more amino acid or nucleic acid deletions, additions, substitutions or side-chain modifications, yet retains one or more functions or biological activities of the naturally occurring molecule. Amino acid substitutions include alterations in which an amino acid is replaced with a different naturally-occurring or a non-conventional amino acid residue. Such substitutions may be classified as "conservative," in which case an amino acid residue contained in a polypeptide is replaced with another naturally occurring amino acid of similar character either in relation to polarity, side chain functionality or size. Substitutions encompassed by variants as described herein may also be "non conservative," in which an amino acid residue which is present in a peptide is substituted with an amino acid having different properties (e.g., substituting a charged or hydrophobic amino acid with alanine), or alternatively, in which a naturally-occurring amino acid is substituted with a non-conventional amino acid. Also encompassed within the term "variant," when used with reference to a polynucleotide or polypeptide, are variations in primary, secondary, or tertiary structure, as compared to a reference polynucleotide or polypeptide, respectively (e.g., as compared to a wild-type polynucleotide or polypeptide).

As used herein the term "derivative" refers to a polypeptide that is derived from wild-type AFP as described herein, e.g., an AFP functional fragment, and includes peptides which have been chemically modified by techniques such as adding additional side chains, ubiquitination, labeling, pegylation (derivatization with polyethylene glycol), and insertion, deletion or substitution of amino acid mimetics and/or unnatural amino acids that do not normally occur in the sequence of wild-type AFP that is basis of the derivative. For example, in some embodiments, an AFP derivative can comprise a label, such as, for example, an epitope, e.g., a FLAG epitope or a V5 epitope or an HA epitope. Such a tag can be useful for, for example, purifying a fusion protein derivative. The term "derivative" also encompasses a derivatized polypeptide, such as, for example, a polypeptide modified to contain one or more-chemical moieties other than an amino acid. The chemical moiety can be linked covalently to the peptide, e.g., via an amino terminal amino acid residue, a carboxy terminal amino acid residue, or at an internal amino acid residue. Such modifications include the addition of a protective or capping group on a reactive moiety in the polypeptide, addition of a detectable label, and other changes that do not adversely destroy the activity of the AFP derivative or fusion protein. In some embodiments, an AFP derivative contains additional chemical moieties not normally a part of the molecule. Such moieties can improve its solubility, absorption, biological half life, etc. The moieties can alternatively decrease the toxicity of the molecule, or eliminate or attenuate an undesirable side effect of the molecule, etc. Moieties capable of mediating such effects are disclosed, for example, in Remington's Pharmaceutical Sciences, 18th edition, A. R. Gennaro, Ed., MackPubl., Easton, PA (1990).

In some embodiments, an AFP functional fragment comprises an AFP functional fragment that differs by 1 conservative substitution, 2 conservative substitutions, 3 conservative substitutions, 4 conservative substitutions, 5 conservative substitutions, 6 conservative substitutions, 7 conservative substitutions, 8 conservative substitutions, 9 conservative substitutions, 10 or fewer conservative substitutions, 15 or fewer conservative substitutions, 20 or fewer conservative substitutions, 25 or fewer conservative substitutions, 30 or fewer conservative substitutions, 35 or fewer conservative substitutions, 40 or fewer conservative substitutions, 45 or fewer conservative substitutions, or 50 or fewer conservative substitutions, relative to the the sequence of the naturally occurring AFP molecule or a domain or portion thereof of AFP having the desired biological activity.

In some embodiments, an AFP functional fragment differs by 1 or fewer non-conservative substitutions, 2 or fewer non-conservative substitutions, 3 or fewer non-conservative substitutions, 4 or fewer non-conservative substitutions, 5 or fewer non-conservative substitutions, 6 or fewer non-conservative substitutions, 7 or fewer or non-conservative substitutions, 8 or fewer non-conservative substitutions, 9 or fewer non-conservative substitutions, 10 or fewer or non-conservative substitutions, 15 or fewer or non-conservative substitutions, relative to the the sequence of the naturally occurring AFP molecule or a domain or portion thereof of AFP having the desired biological activity.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

AFP-FcRn potentiators for use in the compositions, methods, and uses described herein can be identified or characterized using methods known in the art, such as protein-protein binding assays, biochemical screening assays, immunoassays, and cell-based assays, which are well known in the art, such as those described herein in the Examples.

For the clinical use of the methods and uses described herein, administration of the compositions comprising AFP-FcRn inhibitors or AFP-FcRn potentiators can include formulation into pharmaceutical compositions or pharmaceutical formulations for parenteral administration, e.g., intravenous; mucosal, e.g., intranasal; ocular, or other mode of administration. In some embodiments, the AFP-FcRn inhibitors or AFP-FcRn potentiators described herein, can be administered along with any pharmaceutically acceptable carrier compound, material, or composition which results in an effective treatment in the subject. Thus, a pharmaceutical formulation for use in the methods described herein can contain an AFP-FcRn inhibitors or AFP-FcRn potentiator as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of an AFP-FcRn inhibitor or AFP-FcRn potentiator. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (19) pH buffered solutions; (20) polyesters, polycarbonates and/or polyanhydrides; (21) bulking agents, such as polypeptides and amino acids (22) serum components, such as serum albumin, HDL and LDL; (23) C2-C12 alchols, such as ethanol; and (24) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

The AFP-FcRn inhibitors or AFP-FcRn potentiators described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (7) nasally. Additionally, an AFP-FcRn inhibitor or AFP-FcRn potentiator can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

Further embodiments of the formulations and modes of administration of the compositions comprising AFP-FcRn inhibitors or AFP-FcRn potentiators that can be used in the methods described herein are described below.

Parenteral Dosage Forms. Parenteral dosage forms of the AFP-FcRn inhibitors or AFP-FcRn potentiators can also be administered to a subject by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Aerosol formulations. An AFP-FcRn inhibitor or AFP-FcRn potentiator can be packaged in a pressurized aerosol container together with suitable propellants, for example, hydrocarbon propellants like propane, butane, or isobutane with conventional adjuvants. An AFP-FcRn inhibitor or AFP-FcRn potentiator described herein, can also be administered in a non-pressurized form such as in a nebulizer or atomizer. An AFP-FcRn inhibitor or AFP-FcRn potentiator described herein, can also be administered directly to the airways in the form of a dry powder, for example, by use of an inhaler.

Suitable powder compositions include, by way of illustration, powdered preparations of AFP-FcRn inhibitors or AFP-FcRn potentiators described herein, thoroughly intermixed with lactose, or other inert powders acceptable for intrabronchial administration. The powder compositions can be administered via an aerosol dispenser or encased in a breakable capsule which can be inserted by the subject into a device that punctures the capsule and blows the powder out in a steady stream suitable for inhalation. The compositions can include propellants, surfactants, and co-solvents and can be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

The formulations of the AFP-FcRn inhibitors or AFP-FcRn potentiators described herein, further encompass anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, N.Y., N.Y.: 1995). Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms. In some embodiments of the aspects described herein, AFP-FcRn inhibitors or AFP-FcRn potentiators can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of an AFP-FcRn inhibitor or AFP-FcRn potentiator is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the AFP-FcRn inhibitors or AFP-FcRn potentiators described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUOLITE® A568 and DUOLITE® AP143 (Rohm & Haas, Spring House, Pa. USA).

In some embodiments of the methods described herein, the AFP-FcRn inhibitors or AFP-FcRn potentiators for use in the methods described herein are administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the disorder occurs continuously in the subject, for example where the subject has continuous or chronic symptoms of a viral infection. Each pulse dose can be reduced and the total amount of the AFP-FcRn inhibitors or AFP-FcRn potentiators described herein administered over the course of treatment to the subject or patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Methods of Treatment and Uses of AFP-FcRn Inhibitors and Potentiators

As demonstrated herein, alpha-fetoprotein (AFP) is a third ligand for the neonatal Fc receptor and soluble human FcRn binds to AFP with affinities greater than observed with albumin, and less than that of IgG. As further shown herein, the AFP binding site on FcRn interferes with the albumin and IgG binding activities of FcRn, and antibodies that are specific for the albumin site on hFcRn can decrease FcRn-mediated AFP transport. As also demonstrated herein, the binding of FcRn to AFP occurs over a much wider pH range than that observed for IgG and albumin, which typically bind under acidic pH conditions. In addition, provided herein are single nucleotide polymorphisms in AFP that can impact binding of AFP with human FcRn, such as, for example, G109R, R4875, and S445L that increase AFP-FcRn binding, and T451I and D536V, that decrease AFP-FcRn binding.

Accordingly, provided herein, in some aspects, are methods to inhibit or reduce FcRn and AFP interactions in diseases or disorders where elevated AFP levels are associated with immunosuppression comprising administering a therapeutically effective amount of a pharmaceutical composition comprising an AFP-FcRn inhibitor to a subject in need thereof.

In some embodiments of these aspects and all such aspects described herein, an AFP-FcRn inhibitor comprises a T451I and/or D536V polymorphism of wild-type AFP that decreases AFP-FcRn binding.

In some embodiments of these aspects and all such aspects described herein, an AFP-FcRn inhibitor inhibits binding and/or interactions between Y521 and/or V522 of AFP and R42 of FcRn.

In some embodiments of these aspects and all such aspects described herein, an AFP-FcRn inhibitor inhibits binding and/or interactions between P492 of AFP and R69 of FcRn.

In some embodiments of these aspects and all such aspects described herein, an AFP-FcRn inhibitor inhibits binding and/or interactions between Q441 and/or V493 of AFP and E44 of FcRn.

In some embodiments of these aspects and all such aspects described herein, an AFP-FcRn inhibitor inhibits binding and/or interactions between H534 and/or E589 of AFP and N173 of FcRn.

In some embodiments of these aspects and all such aspects described herein, an AFP-FcRn inhibitor inhibits binding between the hydrophobic core of AFP and FcRn. In some such embodiments, an AFP-FcRn inhibitor inhibits binding and/or interactions between L484, V493, V497, and/or F512 of AFP and V57, W59, and/or W61 of FcRn.

In some embodiments of these aspects and all such aspects described herein, an AFP-FcRn inhibitor inhibits binding and/or interactions between T443 of AFP and E62 and/or W59 of FcRn.

In some embodiments of these aspects and all such aspects described herein, an AFP-FcRn inhibitor inhibits binding and/or interactions between D529 of AFP and S230 of FcRn.

In some embodiments of these aspects and all such aspects described herein, an AFP-FcRn inhibitor inhibits binding between S527 and/or D528 of AFP and E50 and/or 67Y of β2m complexed with FcRn.

In some embodiments of these aspects and all such aspects described herein, an AFP-FcRn inhibitor inhibits binding between R604 of AFP and the carbonyl oxygen at E50 of β2m complexed with FcRn.

In some embodiments of these aspects and all such aspects described herein, an AFP-FcRn inhibitor inhibits binding and/or interactions between Q597 of AFP and E69 of β2m complexed with FcRn.

In some embodiments of these aspects and all such aspects described herein, an AFP-FcRn inhibitor inhibits binding and/or interactions between E106 of AFP and H161 of FcRn.

In some embodiments of these aspects and all such aspects described herein, an AFP-FcRn inhibitor inhibits binding and/or interactions between S135 of AFP and H161 of FcRn.

In some embodiments of these aspects and all such aspects described herein, an AFP-FcRn inhibitor inhibits binding and/or interactions between F531, F533, F552, and/or F575 of AFP and W53 of FcRn.

In some embodiments of these aspects and all such aspects described herein, a subject having a disease or disorder associated with elevated AFP levels has or has been diagnosed with cancer.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; cholangiocarcinoma; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intraepithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; teratocarcinoma; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), tumors of primitive origins and Meigs' syndrome.

In some embodiments of these methods and all such methods described herein, a subject having a disease or disorder associated with elevated AFP levels has or has been diagnosed with a cancer or tumor of primitive origin, a tumor of liver origin, such as a hepatoma, a tumor of biliary origin, such as cholangiocarcinoma, stomach cancer, pancreatic cancer, or a teratocarcinoma.

In some embodiments of these methods and all such methods described herein, the methods further comprise administering an anti-cancer therapy or agent to a subject in addition to the AFP-FcRn inhibitors described herein.

The term "anti-cancer therapy" refers to a therapy useful in treating cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets PD1, PDL1, PDL2, TIM3 or any TIM family member, CEACAM1 or any CEACAM family member, ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also specifically contemplated for the methods described herein.

In some embodiments, an anti-cancer thereapy comprises an immunotherapy such as adoptive cell transfer. "Adoptive cell transfer," as used herein, includes immunotherapies involving genetically engineering a subject or patient's own T cells to produce special receptors on their surface called chimeric antigen receptors (CARs). CARs are proteins that allow the T cells to recognize a specific protein (antigen) on tumor cells. These engineered CAR T cells are then grown in the laboratory until they number in the billions. The expanded population of CART cells is then infused into the patient. After the infusion, the T cells multiply in the subject's body and, with guidance from their engineered receptor, recognize and kill cancer cells that harbor the antigen on their surfaces.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including active fragments and/or variants thereof.

In some embodiments of these methods and all such methods described herein, the methods further comprise administering a chemotherapeutic agent to the subject being administered the AFP-FcRn inhibitors described herein.

Non-limiting examples of chemotherapeutic agents can include include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chlorambucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE, vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB.); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above. In addition, the methods of treatment can further include the use of radiation or radiation therapy.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; Baltzer L, Berkery R (eds): Oncology Pocket Guide to Chemotherapy, 2nd ed. St. Louis, Mosby-Year Book, 1995; Fischer D S (ed): The Cancer Chemotherapy Handbook, 4th ed. St. Louis, Mosby-Year Book, 2003)).

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

In some embodiments of these methods and all such methods described herein, the methods further comprise administering a tumor or cancer antigen to a subject being administered the AFP-FcRn inhibitors described herein.

A number of tumor antigens have been identified that are associated with specific cancers. As used herein, the terms "tumor antigen" and "cancer antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER-2, mucins (i.e., MUC-1), prostate-specific antigen (PSA), and prostatic acid phosphatase (PAP). In addition, viral proteins such as hepatitis B (HBV), Epstein-Barr (EBV), and human papilloma (HPV) have been shown to be important in the development of hepatocellular carcinoma, lymphoma, and cervical cancer, respectively. However, due to the immunosuppression of patients diagnosed with cancer, the immune systems of these patients often fail to respond to the tumor antigens.

By "reduce" or "inhibit" in terms of the cancer treatment methods described herein is meant the ability to cause an overall decrease preferably of 20% or greater, 30% or greater, 40% or greater, 45% or greater, more preferably of 50% or greater, of 55% or greater, of 60% or greater, of 65% or greater, of 70% or greater, and most preferably of 75% or greater, 80% or greater, 85% or greater, 90% or greater, or 95% or greater, for a given parameter or symptom. Reduce or inhibit can refer to, for example, the symptoms of the disorder being treated, the presence or size of metastases or micrometastases, the size of the primary tumor, the presence or the size of the dormant tumor, etc.

As used herein, "alleviating a symptom of a cancer or tumor" is ameliorating any condition or symptom associated with the cancer such as the symptoms of the cancer being treated, the presence or size of metastases or micrometastases, the size of the primary tumor, the presence or the size of the dormant tumor, etc. As compared with an equivalent untreated control, such as a subject prior to the administration of the AFP-FcRn inhibitors, such reduction or degree of prevention is at least 5%, 10%, 20%, 40%, 50%, 60%, 80%, 90%, 95%, or more as measured by any standard technique known to one of ordinary skill in the art. A patient or subject who is being treated for a cancer or tumor is one who a medical practitioner has diagnosed as having such a condition. Diagnosis can be by any suitable means.

Also provided herein, in some aspects, are methods to increase or potentiate FcRn and AFP interactions in diseases or disorders associated with decreased AFP levels or where increasing AFP levels is beneficial comprising administering a therapeutically effective amount of a pharmaceutical composition comprising an AFP-FcRn potentiator to a subject in need thereof.

In some embodiments of these aspects and all such aspects described herein, an AFP-FcRn potentiator comprises a G109R, R487S, and/or S445L polymorphism of wild-type AFP that increases AFP-FcRn binding.

In some embodiments of these aspects and all such aspects described herein, an AFP-FcRn potentiator enhances binding and/or interactions between Y521 and/or V522 of AFP and R42 of FcRn.

In some embodiments of these aspects and all such aspects described herein, an AFP-FcRn potentiator enhances binding and/or interactions between P492 of AFP and R69 of FcRn.

In some embodiments of these aspects and all such aspects described herein, an AFP-FcRn potentiator enhances binding and/or interactions between Q441 and/or V493 of AFP and E44 of FcRn.

In some embodiments of these aspects and all such aspects described herein, an AFP-FcRn potentiator enhances binding and/or interactions between H534 and/or E589 of AFP and N173 of FcRn.

In some embodiments of these aspects and all such aspects described herein, an AFP-FcRn potentiator enhances binding between the hydrophobic core of AFP and FcRn. In some such embodiments, an AFP-FcRn potentiator enhances binding and/or interactions between L484, V493, V497, and/or F512 of AFP and V57, W59, and/or W61 of FcRn.

In some embodiments of these aspects and all such aspects described herein, an AFP-FcRn potentiator enhances binding and/or interactions between T443 of AFP and E62 and/or W59 of FcRn.

In some embodiments of these aspects and all such aspects described herein, an AFP-FcRn potentiator enhances binding and/or interactions between D529 of AFP and S230 of FcRn.

In some embodiments of these aspects and all such aspects described herein, an AFP-FcRn potentiator enhances binding between S527 and/or D528 of AFP and E50 and/or 67Y of β2m complexed with FcRn.

In some embodiments of these aspects and all such aspects described herein, an AFP-FcRn potentiator enhances binding between R604 of AFP and the carbonyl oxygen at E50 of β2m complexed with FcRn.

In some embodiments of these aspects and all such aspects described herein, an AFP-FcRn potentiator enhances binding and/or interactions between Q597 of AFP and E69 of β2m complexed with FcRn.

In some embodiments of these aspects and all such aspects described herein, an inhibitor of AFP-FcRn inhibits binding and/or interactions between E106 of AFP and H161 of FcRn.

In some embodiments of these aspects and all such aspects described herein, an inhibitor of AFP-FcRn inhibits binding and/or interactions between S135 of AFP and H161 of FcRn.

In some embodiments of these aspects and all such aspects described herein, an inhibitor of AFP-FcRn inhibits binding and/or interactions between F531, F533, F552, and/or F575 of AFP and W53 of FcRn.

In some embodiments of the compositions, methods, and uses described herein, the AFP-FcRn potentiator is an antibody or antigen-binding fragment thereof that selectively binds or physically interacts with AFP bound to FcRn and enhances the interaction of AFP and FcRn, and/or blocks FcRn binding to albumin and/or IgG but allows binding of AFP to FcRn, thereby resulting in increased transcytosis of AFP, increased inhibition of T cell stimulation by immune complex-primed dendritic cells, increased AFP-mediated inhibition of immune responses, and/or increased serum half-life of AFP.

In some embodiments of these methods and all such methods described herein, a subject in need of increased AFP levels or increased AFP and FcRn interaction or binding is a pregnant subject.

In some embodiments of these methods and all such methods described herein, a subject in need of increased AFP levels or increased AFP and FcRn interaction or binding is a subject at risk for having a problem with establishing and/or maintaining a pregnancy.

In some embodiments, prior to administrating the pharmaceutical compositions comprising AFP-FcRn potentiators described herein to a subject, a subject is first identified as one who has one or more of the following: placental insufficiency (See, e.g., Lepercq and Mahieu-Caputo, 1998, Horm. Res. 49(suppl 2): 14-19); a specific maternal weight and/or height prior to pregnancy (e.g., that is identified as being at risk for non full-term pregnancy); low weight gain during pregnancy; maternal history of non-full term pregnancies (e.g., spontaneous abortion, stillbirth, neonatal death, and/or premature parturition); previous offspring with low birth weight; specific maternal activities placing the pregnancy at risk (e.g., smoking, alcohol and/or drug use, and/or poor nutrition); early intrauterine infections; maternal medical diseases; multiparous pregnancies; a history of or newly experienced complications arising during pregnancy; and/or a general desire for establishing pregnancy and/or maintenance of a healthy pregnancy.

In some embodiments of these methods and all such methods described herein, a subject in need of increased AFP levels or increased AFP and FcRn interaction or binding has or has been diagnosed with an autoimmune disease or disorder.

The methods described herein can, in some aspects, be employed in the context of treatment for an autoimmune disease.

Accordingly, in some embodiments of these methods and all such methods described herein, the autoimmune diseases to be treated or prevented using the methods described herein, include, but are not limited to: rheumatoid arthritis, Crohn's disease or colitis, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjogren's syndrome, insulin resistance, and autoimmune diabetes mellitus (type 1 diabetes mellitus; insulin-dependent diabetes mellitus). Autoimmune disease has been recognized also to encompass atherosclerosis and Alzheimer's disease. In some embodiments of the aspects described herein, the autoimmune disease is selected from the group consisting of multiple sclerosis, type-I diabetes, Hashimoto's thyroiditis, Crohn's disease or colitis, rheumatoid arthritis, systemic lupus erythematosus, gastritis, autoimmune hepatitis, hemolytic anemia, autoimmune hemophilia, autoimmune lymphoproliferative syndrome (ALPS), autoimmune uveoretinitis, glomerulonephritis, Guillain-Barre syndrome, psoriasis and myasthenia gravis.

In some embodiments of these methods and all such methods described herein, a subject in need of increased AFP levels or increased AFP and FcRn interaction or binding has or has been diagnosed with host versus graft disease (HVGD). In a further such embodiment, the subject being treated with the methods described herein is an organ or tissue transplant recipient. In some embodiments, the methods are used for increasing transplantation tolerance in a subject. In some such embodiments, the subject is a recipient of an allogenic transplant.

The transplant can be any organ or tissue transplant, including but not limited to heart, kidney, liver, skin, pancreas, bone marrow, skin or cartilage. "Transplantation tolerance," as used herein, refers to a lack of rejection of the donor organ by the recipient's immune system.

As used herein, in regard to any of the compositions, methods, and uses comprising AFP-FcRn inhibitors or potentiators described herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

The terms "subject," "patient," and "individual" as used in regard to any of the methods described herein are used interchangeably herein, and refer to an animal, for example a human, recipient of the inhibitos described herein. For treatment of disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like. Production mammal, e.g. cow, sheep, pig, and the like are also encompassed in the term subject.

The term "effective amount" as used herein refers to the amount of a AFP-FcRn inhibitor or potentiator described herein, needed to alleviate at least one or more symptom of the disease or disorder being treated, and relates to a sufficient amount of pharmacological composition to provide the desired effect, e.g., increase or decrease serum AFP levels. The term "therapeutically effective amount" therefore refers to an amount of the inhibitors or potentiators described herein, using the methods as disclosed herein, that is sufficient to provide a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions, methods, and uses that exhibit large therapeutic indices are preferred. A therapeutically effective dose can be estimated initially from cell culture assays. Also, a dose can be formulated in animal models to achieve a circulating plasma concentration range that includes the IC50, which achieves a half-maximal inhibition of measured function or activity) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

The AFP-FcRn inhibitors or potentiators described herein can be administered to a subject in need thereof by any appropriate route which results in an effective treatment in the subject. As used herein, the terms "administering," and "introducing" are used interchangeably and refer to the placement of an AFP-FcRn inhibitors or potentiators into a subject by a method or route which results in at least partial localization of such agents at a desired site, such as a tumor site or site of inflammation, such that a desired effect(s) is produced.

In some embodiments, the AFP-FcRn inhibitors or potentiators described herein can be administered to a subject by any mode of administration that delivers the agent systemically or to a desired surface or target, and can include, but is not limited to, injection, infusion, instillation, and inhalation administration. To the extent that polypeptide agents can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of the AFP-FcRn inhibitors or potentiators, other than directly into a target site, tissue, or organ, such that it enters the subject's circulatory system and, thus, is subject to metabolism and other like processes.

It is understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Exemplary embodiments of the various aspects disclosed herein can be described by one or more of the following numbered paragraphs:

A. A pharmaceutical composition comprising an inhibitor of AFP-FcRn and a pharmaceutically acceptable carrier, wherein said inhibitor of AFP-FcRn inhibits binding between alpha-fetoprotein (AFP) and FcRn.

B. The pharmaceutical composition of paragraph A, wherein the inhibitor of AFP-FcRn comprises a T451I and/or D536V polymorphism of wild-type AFP.

C. The pharmaceutical composition of any one of paragraphs A-B, wherein the inhibitor of AFP-FcRn inhibits binding between Y521 and/or V522 of AFP and R42 of FcRn.

D. The pharmaceutical composition of any one of paragraphs A-C, wherein the inhibitor of AFP-FcRn inhibits binding between P492 of AFP and R69 of FcRn.

E. The pharmaceutical composition of any one of paragraphs A-D, wherein the inhibitor of AFP-FcRn inhibits binding between Q441 and/or V493 of AFP and E44 of FcRn.

F. The pharmaceutical composition of any one of paragraphs A-E, wherein the inhibitor of AFP-FcRn inhibits binding between H534 and/or E589 of AFP and N173 of FcRn.

G. The pharmaceutical composition of any one of paragraphs A-F, wherein the inhibitor of AFP-FcRn inhibits binding between the hydrophobic core of AFP and FcRn.

H. The pharmaceutical composition of any one of paragraphs A-G, wherein the inhibitor of AFP-FcRn inhibits binding between L484, V493, V497, and/or F512 of AFP and V57, W59, and/or W61 of FcRn.

The pharmaceutical composition of any one of paragraphs A-H, wherein the inhibitor of AFP-FcRn inhibits binding between T443 of AFP and E62 and/or W59 of FcRn.

J. The pharmaceutical composition of any one of paragraphs A-I, wherein the inhibitor of AFP-FcRn inhibits binding between D529 of AFP and S230 of FcRn.

K. The pharmaceutical composition of any one of paragraphs A-J, wherein the inhibitor of AFP-FcRn inhibits binding between S527 and/or D528 of AFP and E50 and/or 67Y of β2m complexed with FcRn.

L. The pharmaceutical composition of any one of paragraphs A-K, wherein the inhibitor of AFP-FcRn inhibits binding between R604 of AFP and the carbonyl oxygen at E50 of β2m complexed with FcRn.

M. The pharmaceutical composition of any one of paragraphs A-L, wherein the inhibitor of AFP-FcRn inhibits binding between Q597 of AFP and E69 of β2m complexed with FcRn.

N. The pharmaceutical composition of any one of paragraphs A-M, wherein the inhibitor of AFP-FcRn inhibits binding between E106 of AFP and H161 of FcRn.

O. The pharmaceutical composition of any one of paragraphs A-N, wherein the inhibitor of AFP-FcRn inhibits binding between S135 of AFP and H161 of FcRn.

P. The pharmaceutical composition of any one of paragraphs A-O, wherein the inhibitor of AFP-FcRn inhibits binding between F531, F533, F552, and/or F575 of AFP and W53 of FcRn.

Q. The pharmaceutical composition of any one of paragraphs A-P, wherein the inhibitor of AFP-FcRn is an antibody or antigen-binding fragment thereof, a small molecule compound, or an RNA or DNA aptamer.

R. The pharmaceutical composition of paragraph Q, wherein the antibody or antigen-binding fragment thereof is a chimeric, humanized, or completely human antibody or antigen-binding fragment thereof.

S. The pharmaceutical composition of any one of paragraphs A-R, wherein the inhibitor of AFP-FcRn inhibits or blocks the AFP binding site on FcRn.

T. A pharmaceutical composition comprising an AFP-FcRn potentiator and a pharmaceutically acceptable carrier.

U. The pharmaceutical composition of paragraph T, wherein the AFP-FcRn potentiator comprises a G109R, R487S, and/or S445L polymorphism of wild-type alpha-fetoprotein (AFP) that increases AFP-FcRn binding.

V. The pharmaceutical composition of any one of paragraphs T-U, wherein the AFP-FcRn potentiator enhances binding between Y521 and/or V522 of AFP and R42 of FcRn.

W. The pharmaceutical composition of any one of paragraphs T-V, wherein the AFP-FcRn potentiator enhances binding between P492 of AFP and R69 of FcRn.

X. The pharmaceutical composition of any one of paragraphs T-W, wherein the AFP-FcRn potentiator enhances binding between Q441 and/or V493 of AFP and E44 of FcRn.

Y. The pharmaceutical composition of any one of paragraphs T-X, wherein the AFP-FcRn potentiator enhances binding between H534 and/or E589 of AFP and N173 of FcRn.

Z. The pharmaceutical composition of any one of paragraphs T-Y, wherein the AFP-FcRn potentiator enhances binding between the hydrophobic core of AFP and FcRn.

AA. The pharmaceutical composition of any one of paragraphs T-Z, wherein the AFP-FcRn potentiator enhances binding between L484, V493, V497, and/or F512 of AFP and V57, W59, and/or W61 of FcRn.

BB. The pharmaceutical composition of any one of paragraphs T-AA, wherein the AFP-FcRn potentiator enhances binding between T443 of AFP and E62 and/or W59 of FcRn.

CC. The pharmaceutical composition of any one of paragraphs T-BB, wherein the AFP-FcRn potentiator enhances binding between D529 of AFP and S230 of FcRn.

DD. The pharmaceutical composition of any one of paragraphs T-CC, wherein the AFP-FcRn potentiator enhances binding between S527 and/or D528 of AFP and E50 and/or 67Y of β2m complexed with FcRn.

EE. The pharmaceutical composition of any one of paragraphs T-DD, wherein the AFP-FcRn potentiator enhances binding between R604 of AFP and the carbonyl oxygen at E50 β2m complexed with FcRn.

FF. The pharmaceutical composition of any one of paragraphs T-EE, wherein the AFP-FcRn potentiator enhances binding between Q597 of AFP and E69 of β2m complexed with FcRn.

GG. The pharmaceutical composition of any one of paragraphs T-FF, wherein the AFP-FcRn potentiator enhances binding between E106 of AFP and H161 of FcRn.

HH. The pharmaceutical composition of any one of paragraphs T-GG, wherein the AFP-FcRn potentiator enhances binding between S135 of AFP and H161 of FcRn.

II. The pharmaceutical composition of any one of paragraphs T-HH, wherein the AFP-FcRn potentiator enhances binding between 531, F533, F552, and/or F575 of AFP and W53 of FcRn.

JJ. The pharmaceutical composition of any one of paragraphs T-II, wherein the AFP-FcRn potentiator is an antibody or antigen-binding fragment thereof, a small molecule compound, an RNA or DNA aptamer, or an AFP functional fragment.

KK. The pharmaceutical composition of paragraph JJ, wherein the antibody or antigen-binding fragment thereof is a chimeric, humanized, or completely human antibody or antigen-binding fragment thereof.

LL. The pharmaceutical composition of any one of paragraphs T-KK, wherein the AFP-FcRn potentiator binds FcRn and mimics AFP binding MM. The pharmaceutical composition of any one of paragraphs T-LL, wherein the AFP-FcRn potentiator binds or physically interacts with AFP or FcRn, and enhances or promotes interactions between AFP and FcRn.

NN. The pharmaceutical composition of paragraph MM, wherein the AFP-functional fragment comprises Y521 and/or V522 of AFP and can interact with R42 of FcRn.

OO. The pharmaceutical composition of any one of paragraphs JJ or NN, wherein the AFP-functional fragment comprises P492 of AFP and can interact with R69 of FcRn.

PP. The pharmaceutical composition of any one of paragraphs JJ or NN-OO, wherein the AFP-functional fragment comprises Q441 and/or V493 of AFP and can interact with E44 of FcRn.

QQ. The pharmaceutical composition of any one of paragraphs JJ or NN-PP, wherein the AFP-functional fragment comprises H534 and/or E589 of AFP and can interact with N173 of FcRn.

RR. The pharmaceutical composition of any one of paragraphs JJ or NN-QQ, wherein the AFP-functional fragment comprises L484, V493, V497, and/or F512 of AFP and can interact with V57, W59, and/or W61 of FcRn.

SS. The pharmaceutical composition of any one of paragraphs JJ or NN-RR, wherein the AFP-functional fragment comprises T443 of AFP and can interact with E62 and/or W59 of FcRn.

TT. The pharmaceutical composition of any one of paragraphs JJ or NN-SS, wherein the AFP-functional fragment comprises D529 of AFP and can interact with S230 of FcRn.

UU. The pharmaceutical composition of any one of paragraphs JJ or NN-TT, wherein the AFP-functional fragment comprises S527 and/or D528 of AFP and can interact with E50 and/or 67Y of β2m complexed with FcRn.

VV. The pharmaceutical composition of any one of paragraphs JJ or NN-UU, wherein the AFP-functional fragment comprises R604 of AFP and can interact with the carbonyl oxygen at E50 of β2m complexed with FcRn.

WW. The pharmaceutical composition of any one of paragraphs JJ or NN-VV, wherein the AFP-functional fragment comprises Q597 of AFP and can interact with E69 of β2m complexed with FcRn.

XX. The pharmaceutical composition of any one of paragraphs JJ or NN-WW, wherein the AFP-functional fragment comprises E106 of AFP and can interact with H161 of FcRn.

YY. The pharmaceutical composition of any one of paragraphs JJ or NN-XX, wherein the AFP-functional fragment comprises S135 of AFP and can interact with H161 of FcRn.

ZZ. The pharmaceutical composition of any one of paragraphs JJ or NN-YY, wherein the AFP-functional fragment comprises F531, F533, F552, and/or F575 of AFP and can interact with W53 of FcRn.

AAA. A method to inhibit or reduce FcRn and alpha-fetoprotein (AFP) interactions in a disease or disorder associated with elevated AFP levels comprising administering a therapeutically effective amount of a pharmaceutical composition comprising an AFP-FcRn inhibitor of any one of paragraphs A-S to a subject in need thereof.

BBB. The method of paragraph AAA, wherein the subject has or has been diagnosed with cancer.

CCC. The method of any one of paragraphs AAA or BBB, wherein the subject has or has been diagnosed with a cancer or tumor of primitive origin, a tumor of liver origin, such as a hepatoma, a tumor of biliary origin, such as cholangiocarcinoma, stomach cancer, pancreatic cancer, or a teratocarcinoma.

DDD. The method of any one of paragraphs AAA-CCC, further comprising administering an anti-cancer therapy or agent to the subject.

EEE. The method of any one of paragraphs AAA-DDD, further comprising administering a tumor or cancer antigen.

FFF. A method to increase or potentiate FcRn and alpha-fetoprotein (AFP) interactions in diseases or disorders associated with decreased AFP levels or where increasing AFP levels is beneficial comprising administering a therapeutically effective amount of a pharmaceutical composition comprising an AFP-FcRn potentiator of any one of paragraphs T-ZZ to a subject in need thereof.

GGG. The method of paragraph FFF, wherein the subject in need is pregnant or is at risk for having a problem with establishing and/or maintaining a pregnancy.

HHH. The method of paragraph FFF, wherein the subject has or has been diagnosed with an autoimmune disease or disorder.

III. The method of paragraph FFF, wherein the subject has or has been diagnosed with host versus graft disease (HVGD), is an organ or tissue transplant recipient, or a recipient of an allogenic transplant.

EXAMPLES hAFP transcytosis assays were performed as previously described for IgG. In brief, MDCK II cells expressing hβ$_2$m and hFcRn or mβ$_2$m and mFcRn or vector controls (expressing only 11β2m) were grown to confluence on transwells (Costar) and allowed to polarize over 4 days. 12 hours before the transcytosis experiment, the medium was changed to serum-free media without antibiotics. On the day of experiment, the transwells were incubated with HBSS pH 7.4 for 20 minutes before placing on a new 12 well plate (Costar) where the input chamber contained AFP HBSS pH 6.0 or 7.4 (with) and the exit chamber contained HBSS pH 7.4. For blocking AFP transcytosis with the mouse anti-human FcRn antibody (ADM31) or isotype control (IgG2b), transwells were pre-incubated for 20 min with the respective antibodies in HBSS pH 7.4 prior to the addition of AFP to the same side of the chamber. After 2 hours incubation in 36° C. and 5% CO$_2$, the medium at the opposite chamber was harvested and the hAFP concentration was measured using ELISA method. For the AFP inhibition of IgG transcytosis, AFP and IgG were both added in HBSS pH 6 to the input chamber and 2 hours later the medium at the opposite chamber was harvested and IgG was quantified using ELISA method.

In vitro cross-presentation assays were carried out by pulsing 1×10⁵ isolated DC with preformed immune complexes (0.5 µg/ml NIP-conjugated OVA+100 µg/ml anti-NIP IgG or anti-NIP IHH-IgG) for 2-3 h followed by extensive washing and the addition of 2×10⁵ purified OT-I CD8⁺ T cells. The presentation assays were carried out accordingly with the distinction of utilizing 2×10⁵ purified OT-II CD4⁺ T cells. Depending on condition, DCs were pre-incubated with hAFP (50 or 100 µg/ml) or HSA (50 or 100 µg/ml) in presence or absence of ADM31 or IgG2b isotype control (75 or 100 µg/ml). Immune complexes were formed using ovalbumin conjugated to the hapten NIP (4-hydroxy-3-iodo-5-nitrophenylacetic acid) and NIP-specific chimeric IgG (IgG) or IHH-IgG. IHH-IgG is a mutational variant of the chimeric IgG protein which contains a NIP-specific mouse Fab fragment and a human IgG1 Fc fragment and which has been rendered incapable of FcRn binding due to the introduction of mutations in three critical amino acids in the Fc region which are required for FcRn ligation. Cytokine secretion was measured after 24 h or 48 h by ELISA. For the measurement of proliferation, OT-I CD8⁺ T cells were stained with eFluor670 Proliferation Dye according to the manufacturer's instructions (eBioscience) and stimulated as described above.

For in vivo enhanced clearance of hIgG upon hAFP administration effect, hFCGRT/hB2M/mFcgrt−/− mice were injected i.p. with hIgG (100 µg/mouse) and the following day with hAFP (100 µg/mouse). 24, 48 and 72 hrs later blood samples were collected and the amount of hIgG was quantified by ELISA and compared to Day 0.

Surface plasmon resonance was conducted using a Biacore 3000 instrument (GE Healthcare) with CM5 sensor chips coupled with recombinant human FcRn & hβ₂m heterodimer protein or mouse FcRn & mβ₂m (1000 RU). The coupling was performed by injecting 25 µg/mL of the protein diluted in 10 mM sodium acetate pH 5.0 using the amine coupling kit (GE Healthcare). Phosphate buffer (67 mM phosphate buffer, 0.15 M NaCl, 0.005% Tween 20) at pH 6.0 or pH 7.4 was used as running buffer. Glycine pH 2.5 was used for regeneration of the flow cells. hAFP (SinoBiological) was injected at 25° C. with a flow rate of 25 µl/min, and data were analyzed using the BIAevaluation 4.1 software where the sensorgrams were zero adjusted and reference cell values subtracted.

FIG. 1 demonstrates that human AFP (hAFP) is transcytosed by human FcRn (hFcRn) at acidic and neutral pH. Transcytosis of AFP by MDCK II cells co-expressing FcRn and β2 microglobulin (hFcRn/β2m) or vector control at pH 6 and 7.4. B→A Basolateral to apical direction, A→B Apical to basolateral direction.

Figure 2:
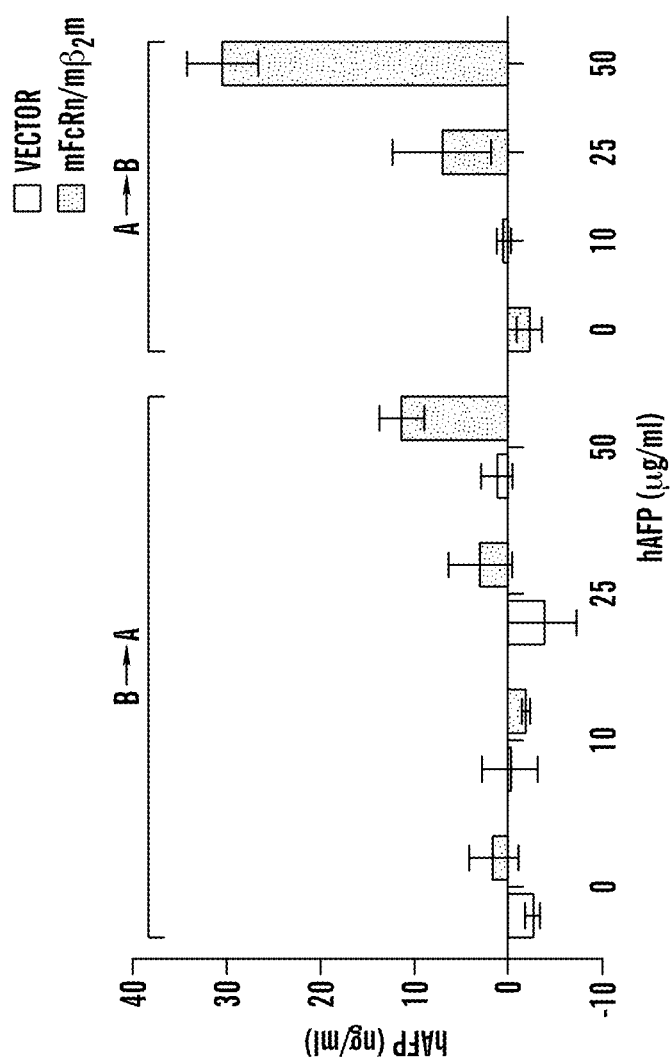
FIG. 2 demonstrates that hAFP is transcytosed by mouse FcRn. Transcytosis of human AFP in MDCK II cells co-expressing mouse FcRn and β2 microglobulin (mFcRn/mβ2m) or vector control at pH 7.4. B→A Basolateral to apical direction, A→B Apical to Basolateral direction.

FIG. 2 demonstrates that hAFP is transcytosed by mouse FcRn. Transcytosis of AFP by MDCK II cells co-expressing mouse FcRn and β2 microglobulin (mFcRn/mβ2m) or vector control at pH 7.4. B→A Basolateral to apical direction, A→B Apical to basolateral direction.

Figure 3:
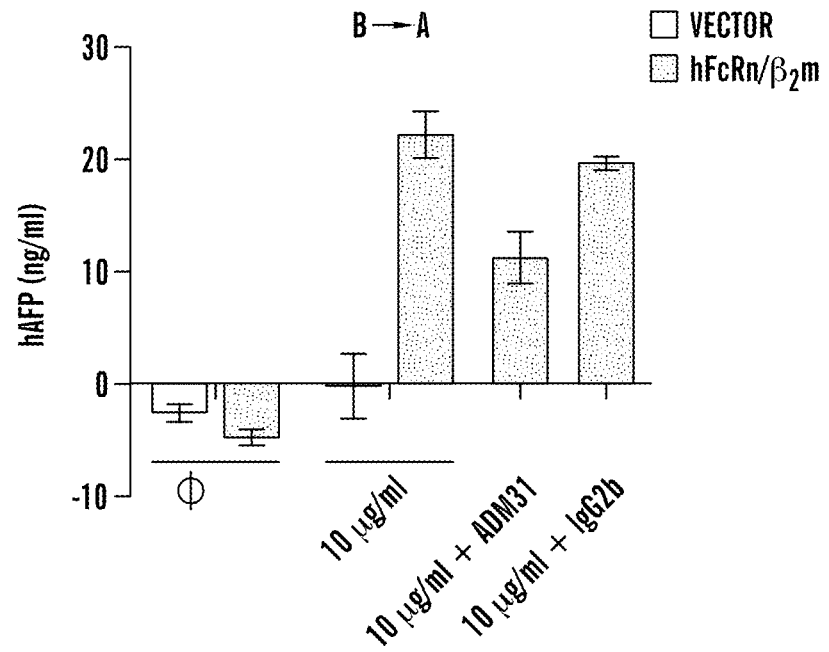
FIG. 3 demonstrates that AFP transcytosis by hFcRn is blocked by ADM31 antibody, which specifically binds to an epitope on FcRn that contains the albumin binding site. Transcytosis of human AFP in MDCK II cells co-expressing human FcRn and β2 microglobulin (mFcRn/mβ2m) or vector control at pH 7.4 in presence of anti-human FcRn antibody (ADM31) or isotype control. B→A Basolateral to apical direction.

FIG. 3 demonstrates that hAFP transcytosis by hFcRn is blocked by ADM31 antibody. Transcytosis of AFP by MDCK II cells co-expressing hFcRn, hβ2m (mFcRn/mβ2m) or vector control at pH 7.4 in presence of anti-human FcRn antibody (ADM31) or isotype control (IgG2b). B→A Basolateral to apical direction.

Figure 4:
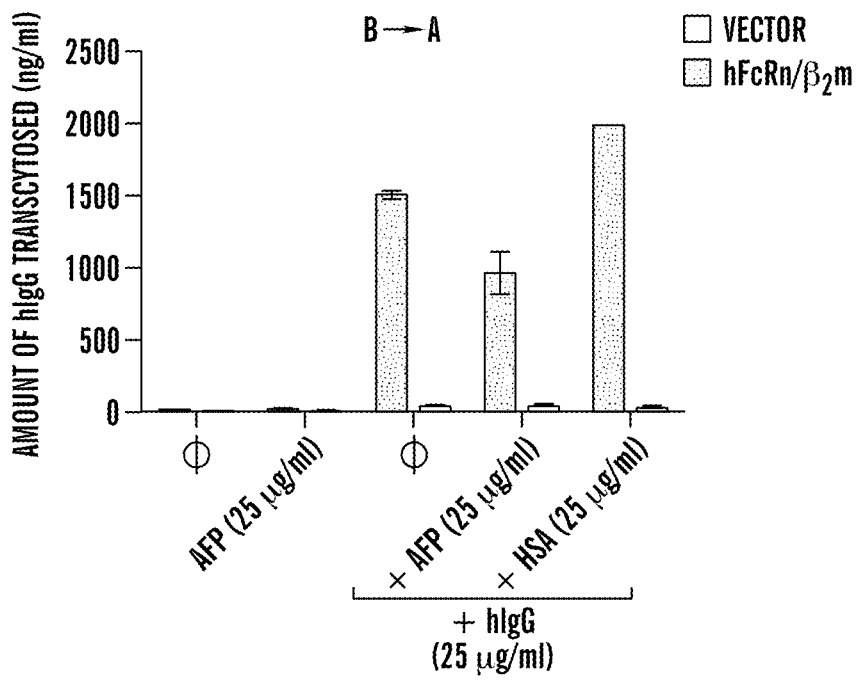
FIG. 4 demonstrates that AFP hinders FcRn-mediated transcytosis of IgG. Transcytosis of human IgG in MDCK II cells co-expressing human FcRn and β2 microglobulin (hFcRn/hβ2m) or vector control at pH 6 which have been pre-incubated with hAFP or Human Serum Albumin (HSA) as control at pH 7.4. Basolateral to apical direction is shown.

FIG. 4 demonstrates that AFP hinders FcRn-mediated transcytosis of IgG. Transcytosis of human IgG by MDCK II cells co-expressing hFcRn, hβ2m, or vector control at pH 6 which have been pre-incubated with hAFP or Human Serum Albumin (HSA) as control at pH 7.4. Basolateral to apical direction is shown.

Figure 5:
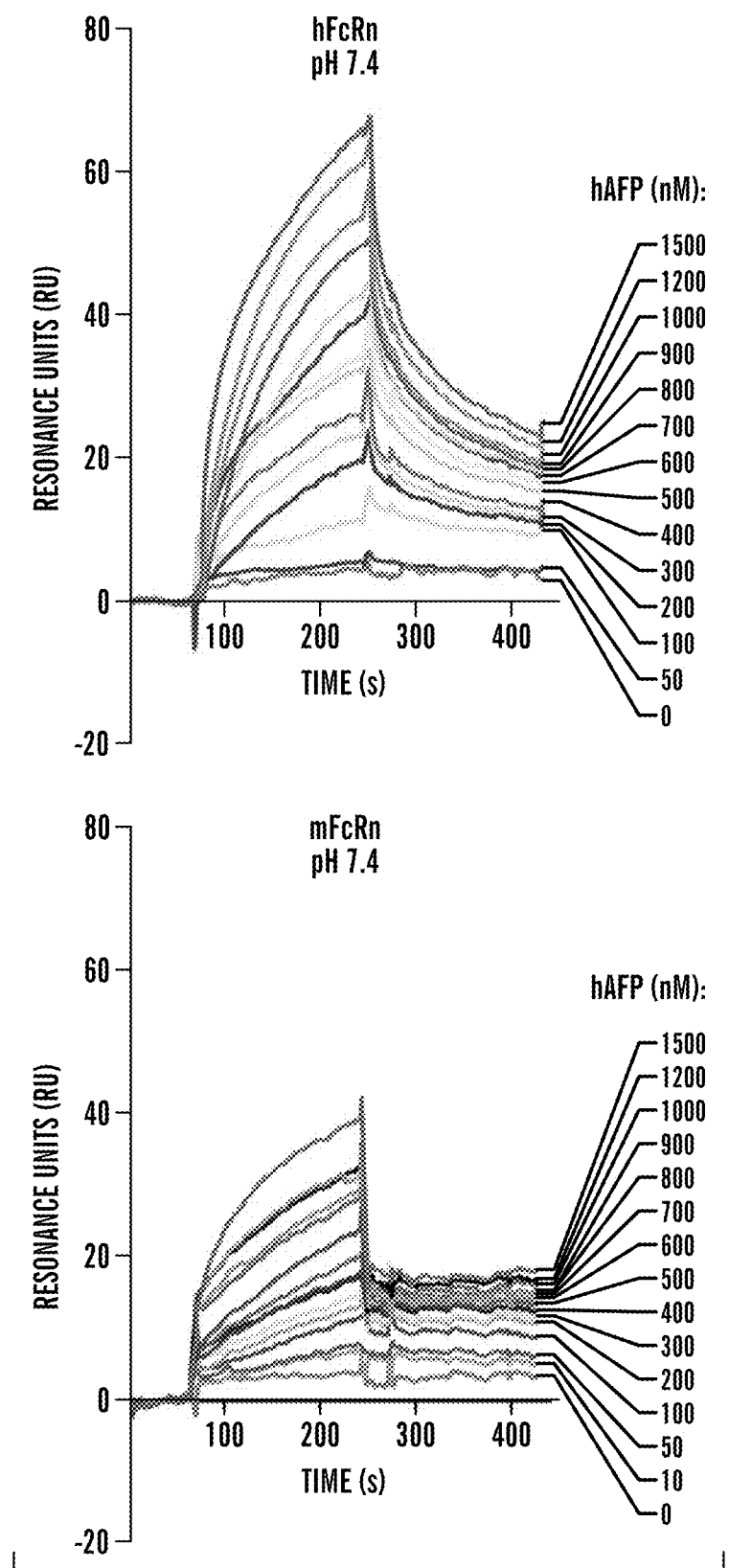
FIG. 5 demonstrates that AFP binds to human and mouse FcRn at neutral pH. SPR analyses of hAFP binding to hFcRn (left panel) or mFcRn (right panel) at neutral pH.

FIG. 5 demonstrates that AFP binds to human and mouse FcRn at neutral pH. SPR analyses of hAFP binding to hFcRn (left panel) or mFcRn (right panel) at neutral pH.

Figure 6:
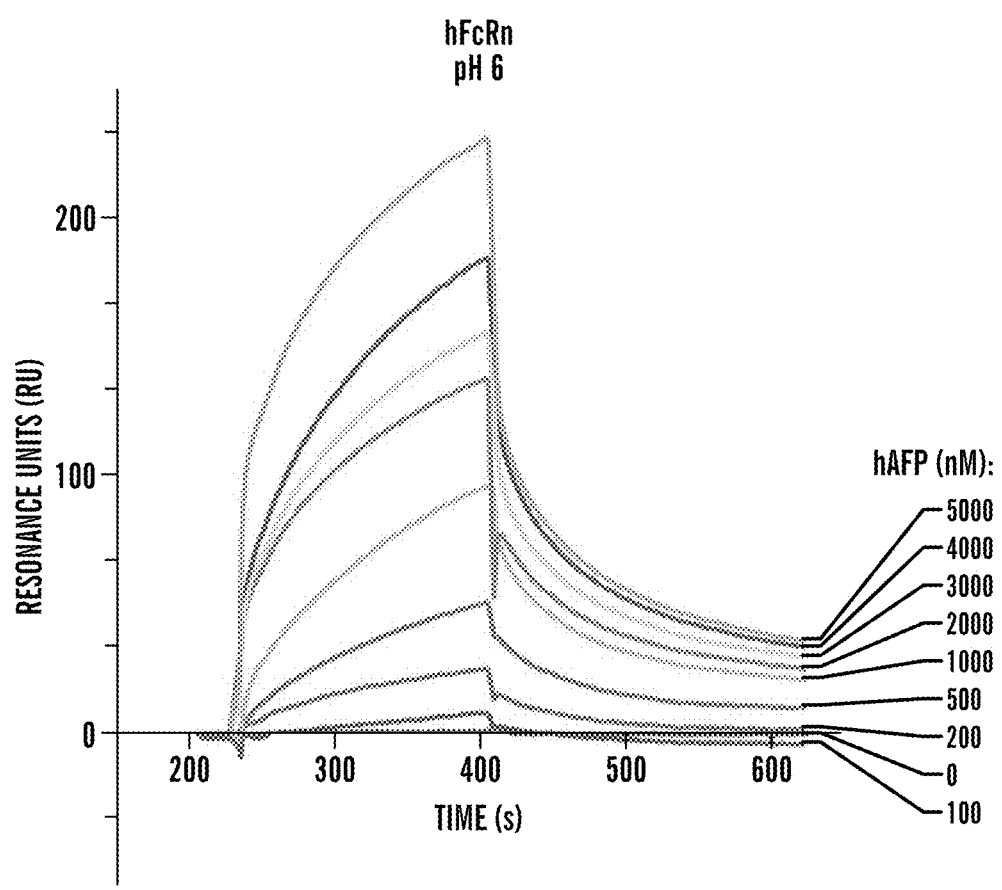
FIG. 6 demonstrates that AFP binds to hFcRn at acidic pH. SPR analyses of hAFP binding to hFcRn at pH 6.

FIG. 6 demonstrates that AFP binds to hFcRn at acidic pH. SPR analyses of hAFP binding to hFcRn at pH 6.

Figure 7:
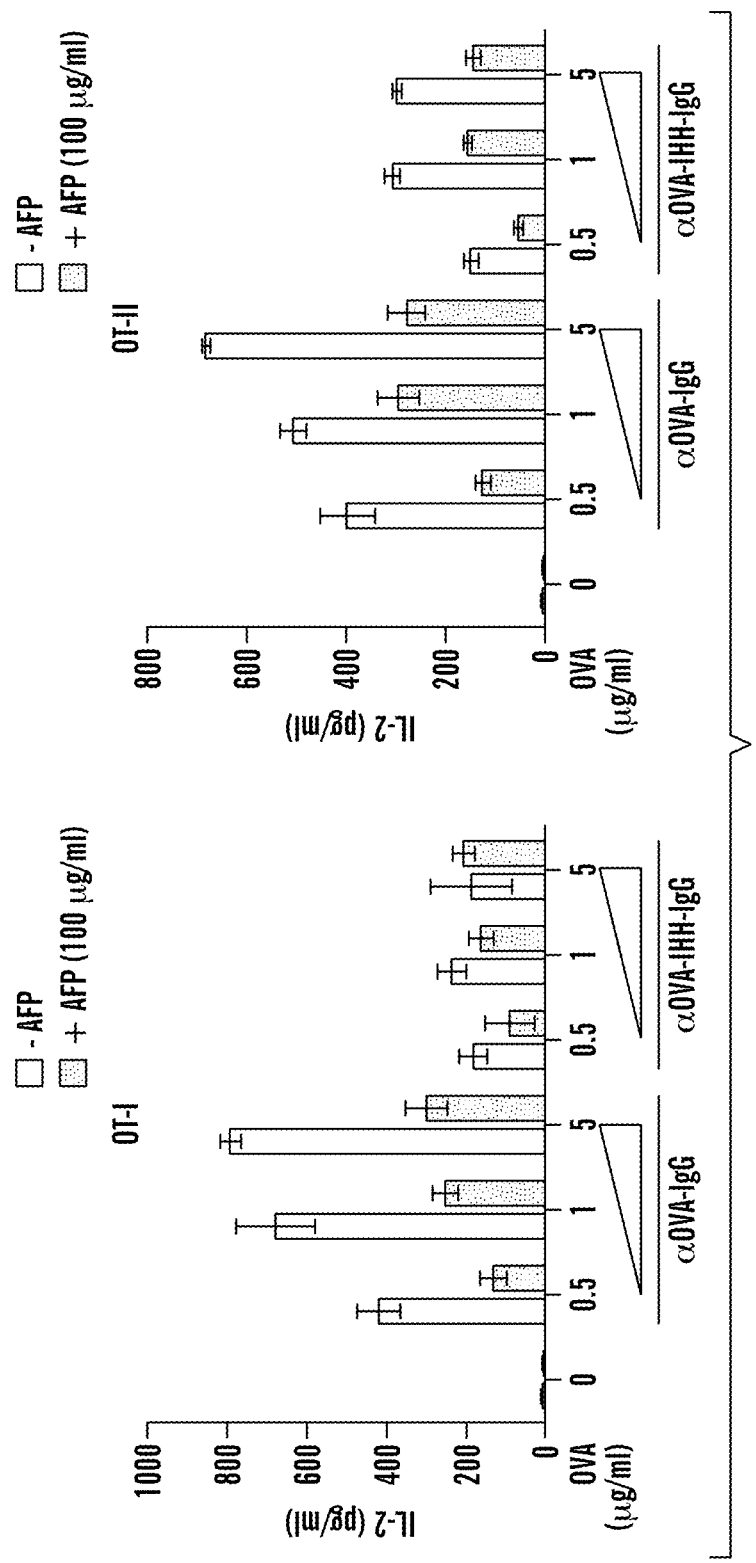
FIG. 7 demonstrates that AFP inhibits T cell stimulation by IgG-immune complex (IC) primed dendritic cells (DC). hAFP blocks proliferation (IL-2 secretion) of CD8+ (OT-I, left panel) or CD4+ (OT-II, right panel) T cells in response to antigen in IgG-IC from bone marrow (BM). DC from hFCGRT/hB2M/mFcgrt−/− human FcRn and β2-microglobulin transgenic and mouse FcRn knockout) mice were treated with 100 μg/ml of IgG or IHH-IgG (FcRn-defective IgG) in association with 0, 0.5, 1, or 5 μg/ml of OVA in presence of 100 μg/ml of hAFP and then co-cultured with either OVA-specific CD8+ or CD4+ T cells. 24 after the stimulation IL-2 secretion in the supernatants were measured by ELISA.

FIG. 7 demonstrates that AFP inhibits T cell stimulation by IgG-IC primed DC. hAFP blocks proliferation (IL-2 secretion) of CD8⁺ (OT-I, left panel) or CD4⁺ (OT-II, right panel) T cells in response to antigen in IgG-IC. BMDC from hFCGRT/hB2M/mFcgrt−/− mice were treated with 100 µg/ml of IgG or IHH-IgG in association with 0, 0.5, 1, or 5 µg/ml of OVA in presence of 100 µg/ml of hAFP and then co-cultured with either OVA-specific CD8⁺ or CD4⁺ T cells. 24 after the stimulation IL-2 secretion in the supernatants were measured by ELISA.

Figure 8:
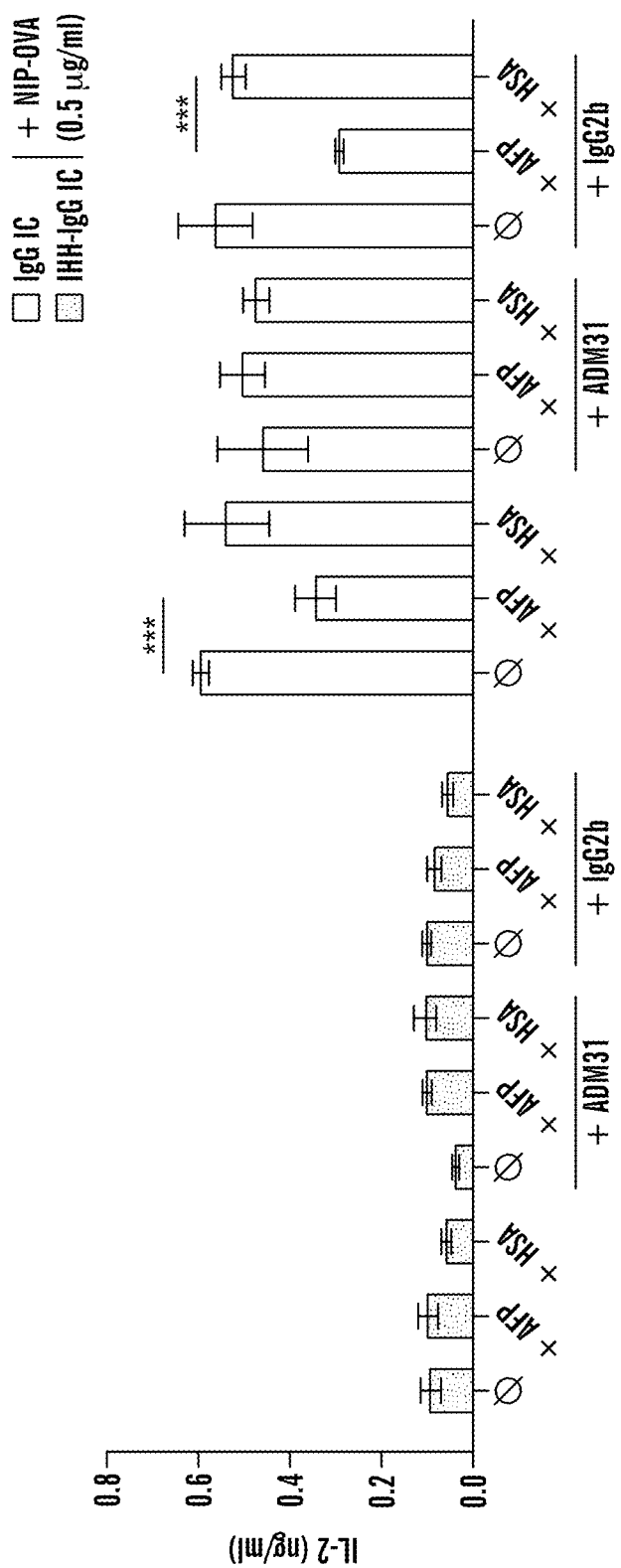
FIG. 8 demonstrates that ADM31 blocks AFP-FcRn-mediated inhibitory functions. ADM31 α-hFcRn monoclonal antibody blocks hAFP inhibition of CD8+ T cell IL-2 secretion in response to antigen in IgG-IC. BMDC from hFCGRT/hB2M/mFcgrt−/− mice were treated with 100 μg/ml of IgG or IHH-IgG in association with 0.5 μg/ml OVA in presence of 50 μg/ml of hAFP or HSA and 50 μg/ml of ADM31 or isotype control, and then co-cultured with OVA-specific CD8+ T cells. 24 after the stimulation IL-2 secretion in the supernatants were measured by ELISA.

FIG. 8 demonstrates that ADM31 blocks AFP-FcRn-mediated inhibitory functions. ADM31, a monoclonal anti-hFcRn antibody blocks hAFP inhibition of CD8⁺ T cell IL-2 secretion in response to antigen in IgG-IC. BMDC from hFCGRT/hB2M/mFcgrt mice were treated with 100 µg/ml of IgG or IHH-IgG in association with 0.5 µg/ml OVA in presence of 50 µg/ml of hAFP or HSA and 50 µg/ml of ADM31 or isotype control, and then co-cultured with OVA-specific CD8⁺ T cells. 24 after the stimulation IL-2 secretion in the supernatants were measured by ELISA.

Figure 9:
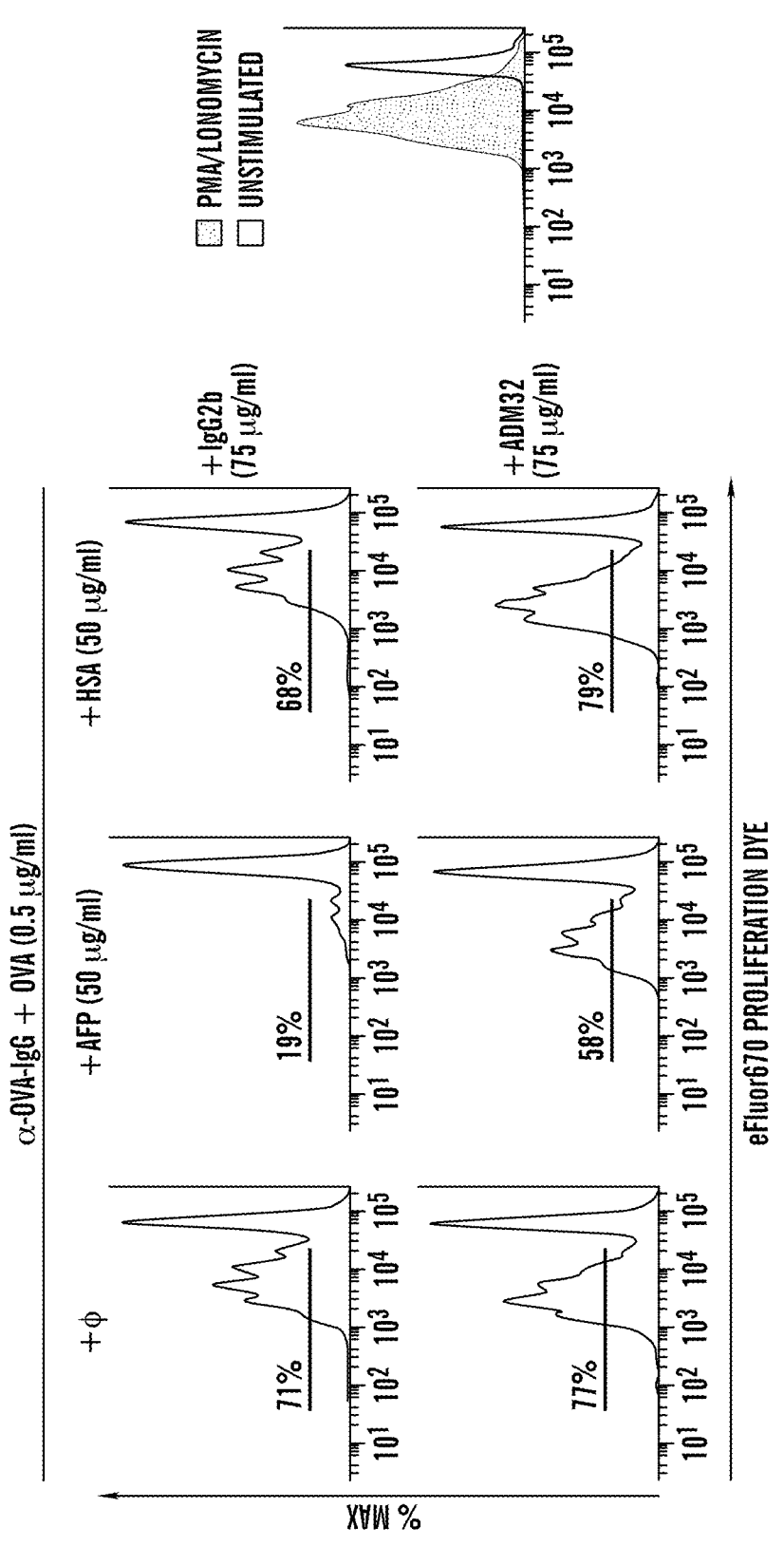
FIG. 9 demonstrates that ADM31 blocks AFP-FcRn-mediated inhibitory functions. ADM31 α-hFcRn monoclonal antibody blocks hAFP inhibition of CD8+ T cell proliferation in response to antigen in IgG-IC. BMDC from hFCGRT/hB2M/mFcgrt−/− mice were treated with 100 μg/ml of IgG or IHH-IgG in association with 0.5 μg/ml OVA in presence of 50 μg/ml of hAFP or HSA and 50 μg/ml of ADM31 or isotype control, and then co-cultured with CD8+ T cells labelled with eFluor670 Proliferation Dye. 72 hrs later the cells were acquired. Percent of proliferated cells is displayed.

FIG. 9 demonstrates that ADM31 blocks AFP-FcRn-mediated inhibitory functions. ADM31 blocks hAFP inhibition of CD8⁺ T cell proliferation in response to antigen in IgG-IC. BMDC from hFCGRT/hB2M/mFcgrt mice were treated with 100 µg/ml of IgG or IHH-IgG in association with 0.5 µg/ml OVA in presence of 50 µg/ml of hAFP or HSA and 50 µg/ml of ADM31 or IgG2b isotype control, and then co-cultured with CD8⁺ T cells labelled with eFluor670 Proliferation Dye. 72 hrs later the cells were acquired. Percent of proliferated cells is displayed.

Figure 10:
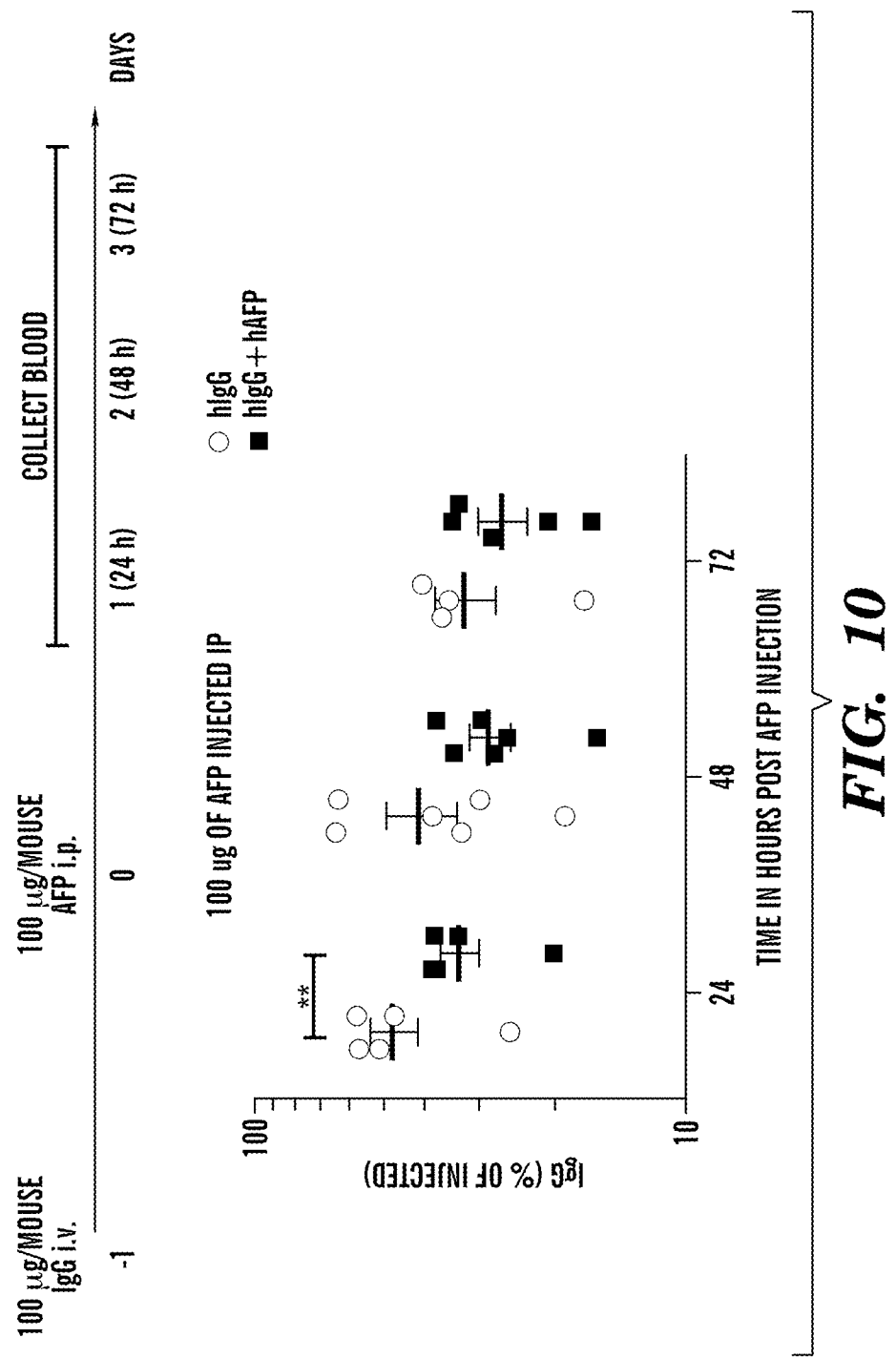
FIG. 10 demonstrates that administration of hAFP results in increased clearance of hIgG antibodies from systemic circulation. hFCGRT/hB2M/mFcgrt−/− mice were injected with hIgG and the following day with hAFP. 24, 48 and 72 hrs later blood samples were collected and the amount of hIgG was quantified by ELISA and compared to Day 0. The results illustrate that AFP injection resulted in faster clearance of hIgG from circulation.

FIG. 10 demonstrates that administration of hAFP results in increased clearance of hIgG antibodies from systemic circulation. hFCGRT/hB2M/mFcgrt mice were injected with hIgG and the following day with hAFP. 24, 48 and 72 hrs later blood samples were collected and the amount of hIgG was quantified by ELISA and compared to Day 0. The results illustrate that AFP injection resulted in faster clearance of hIgG from circulation.

Figure 11:
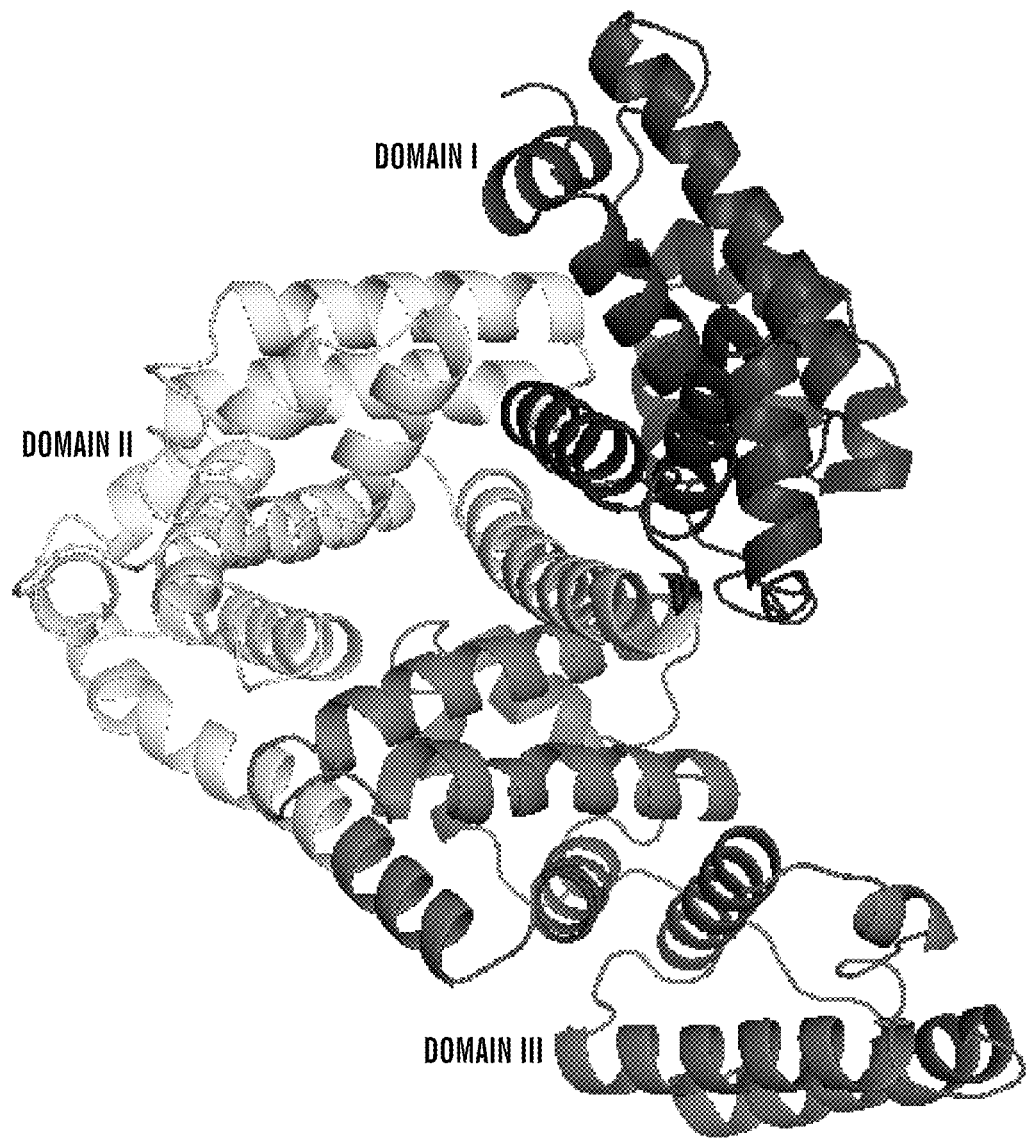
FIG. 11 shows an AFP homology model derived from human serum albumin (HSA) Crystal Structure (PDB ID: 4NOF). Based on high homology between HSA and AFP, a structural model of AFP was built and superimposed on FcRn:HSA:Fc-YTE structure (PDB ID 4N0U) with RMSD of 0.072. All the figures were drawn using PyMOL (DELANO SCIENTIFIC) and labels were added using ADOBE® Photoshop.

FIG. 11 shows an AFP homology model derived from HSA Crystal Structure (PDB ID: 4N0F).

Figure 12:
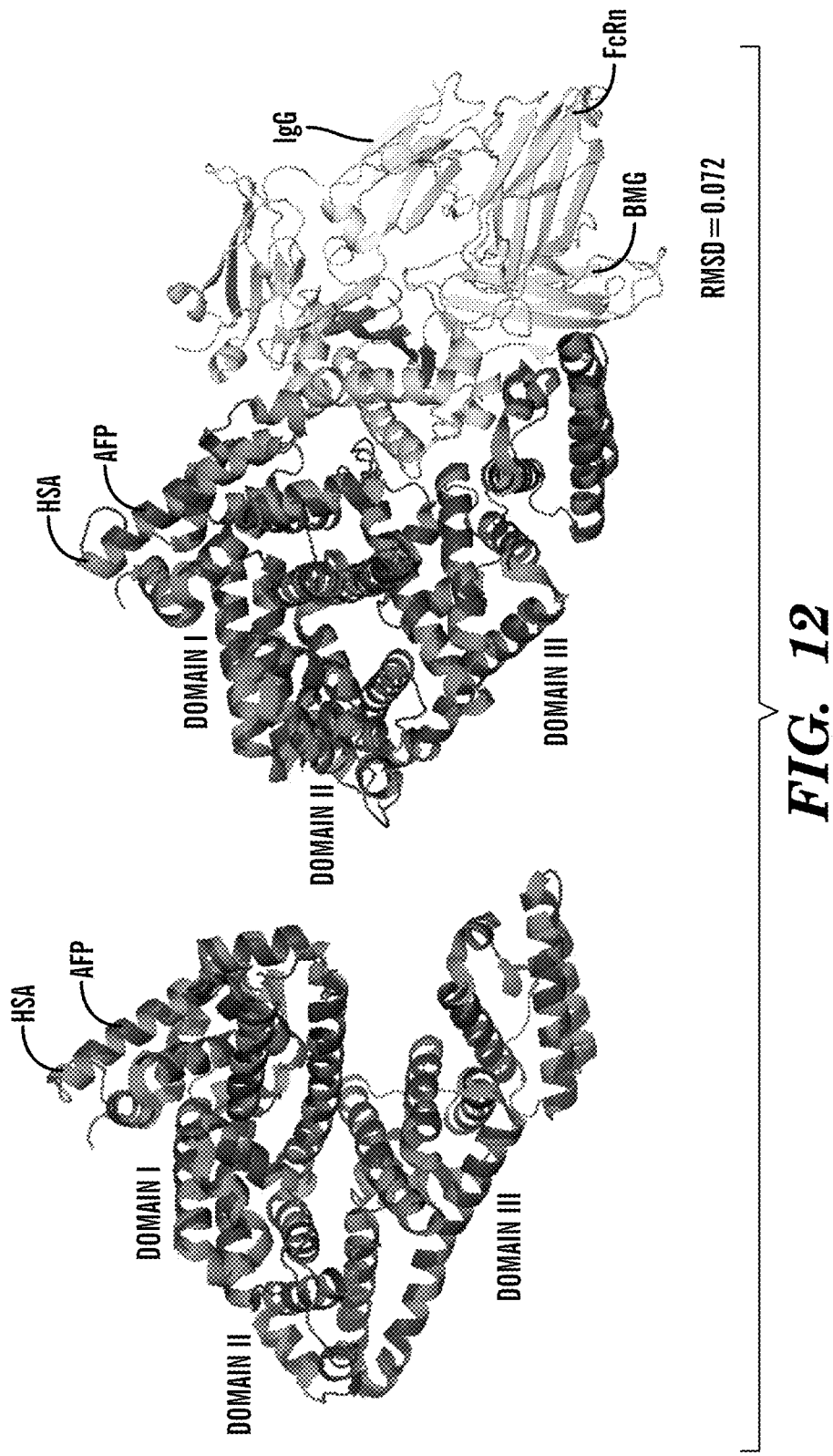
FIG. 12 depicts superimposition of AFP model on HSA (left panel) or FcRn-HSA-IgG ternary complex crystal structure (PDB ID: 4NOU) (right panel).

FIG. 12 depicts superimposition of AFP model on FcRn-HSA-IgG ternary complex crystal structure (PDB ID: 4NOU).

Figure 13:
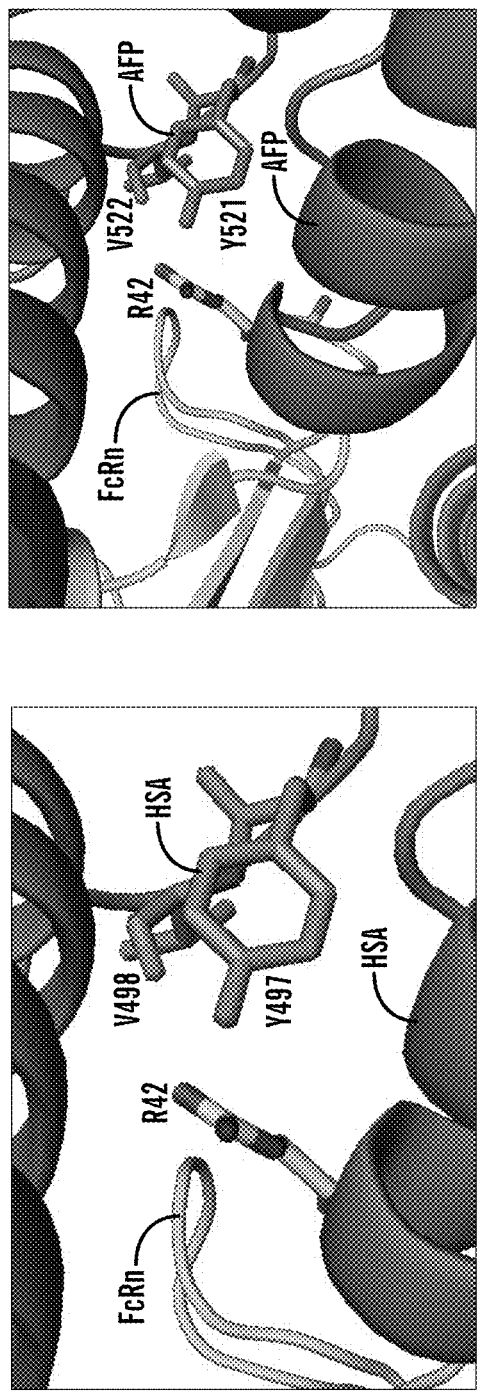
FIG. 13 depicts HSA Y497/V498 residues are conserved in AFP (Y521/V522) and interact with FcRn R42. HSA/AFP have conserved residues in Domain III that establish binding to FcRn.

FIG. 13 depicts HSA Y497/V498 residues are conserved in AFP (Y521/V522) and interact with FcRn R42. HSA/AFP conserved residues in Domain III that establish binding to FcRn.

Figure 14:
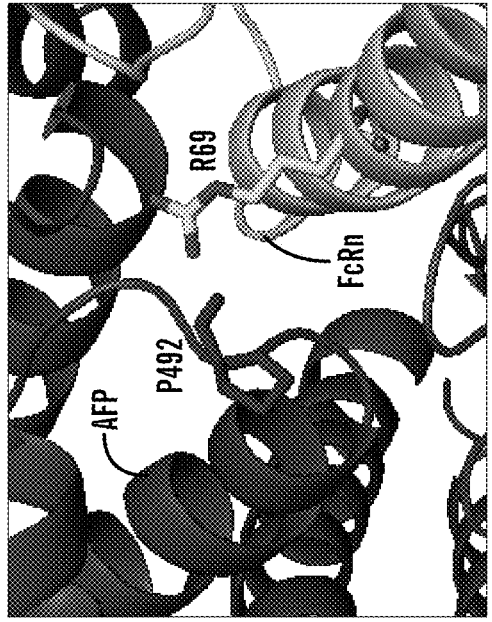
FIG. 14 demonstrates that HSA P468 residue is conserved in AFP (P492) and interacts with FcRn R69. HSA/AFP conserved residues in Domain III that establish binding to FcRn FIG. 15 demonstrates that HSA Q417/V469 residues are conserved in AFP (Q441/V493) and interact with FcRn E44. HSA/AFP conserved residues in Domain III establish binding to FcRn AFP. HSA V469/AFPV493 make backbone contacts with conserved HSA H464/AFP H488.
Figure 14:
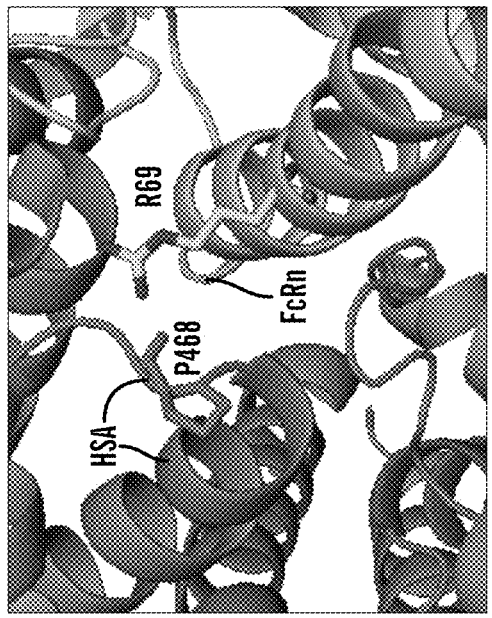
Figure 15:
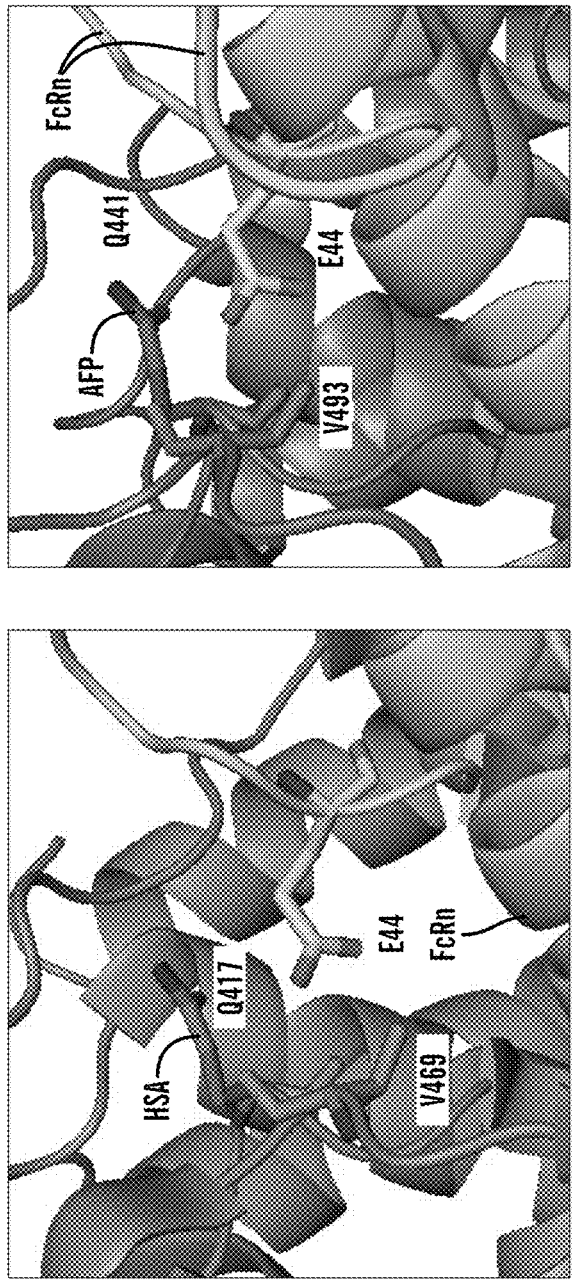

FIG. 14 demonstrates that HSA P468 residue is conserved in AFP (P492) and interacts with FcRn R69. HSA/AFP conserved residues in Domain III that establish binding to FcRn FIG. 15 demonstrates that HSA Q417/V469 residues are conserved in AFP (Q441/V493) and interact with FcRn E44. HSA/AFP conserved residues in Domain III that establish binding to FcRn AFP. HSA V469/AFPV493 make backbone contacts with conserved HSA H464/AFP H488.

Figure 16:
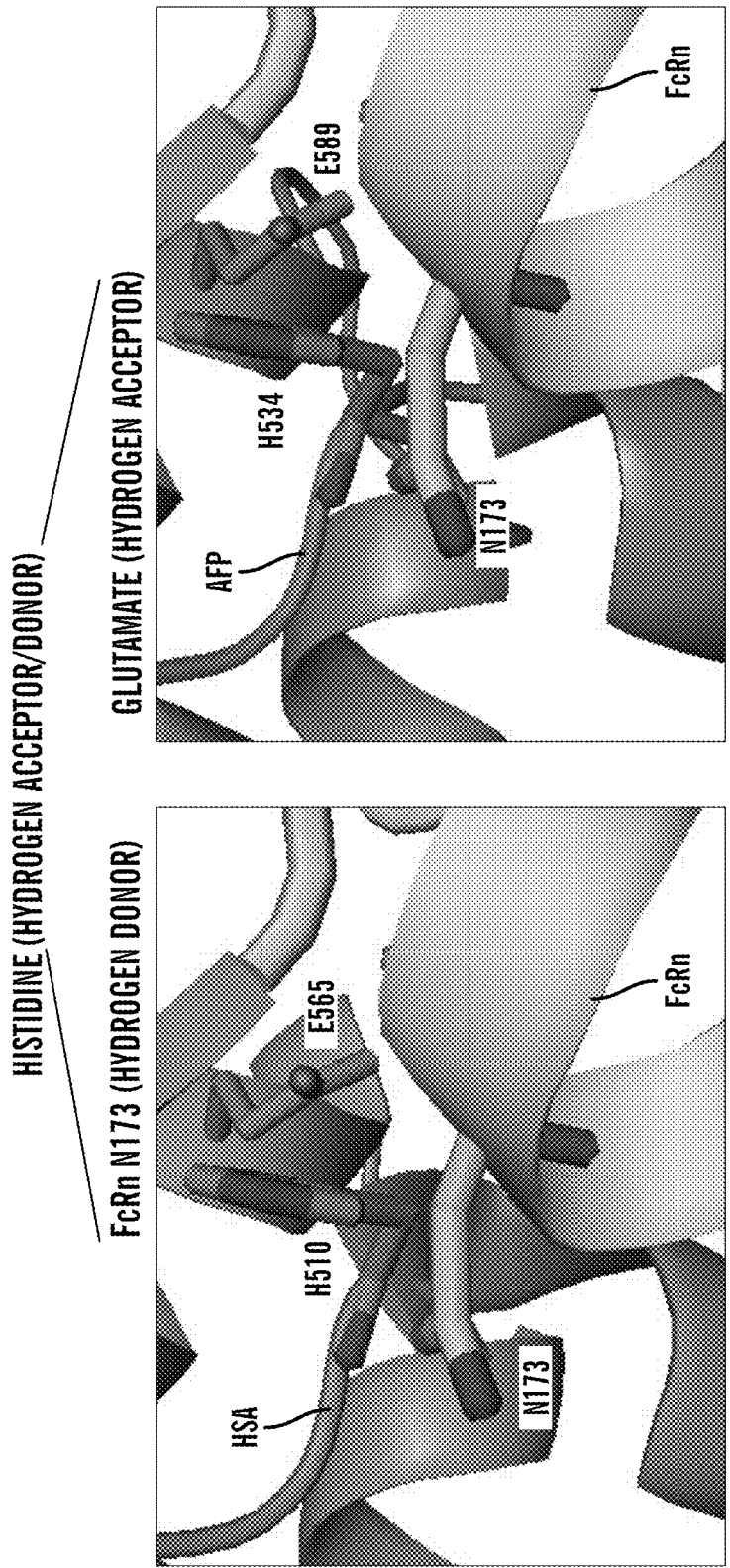
FIG. 16 demonstrates that HSA H510/E565 residues are conserved in AFP (H534/E589) and interact with FcRn N173. HSA/AFP conserved residues in Domain III establish binding to FcRn.

FIG. 16 demonstrates that HSA H510/E565 residues are conserved in AFP (H534/E589) and interact with FcRn N173. HSA/AFP conserved residues in Domain III establish binding to FcRn.

Figure 17:
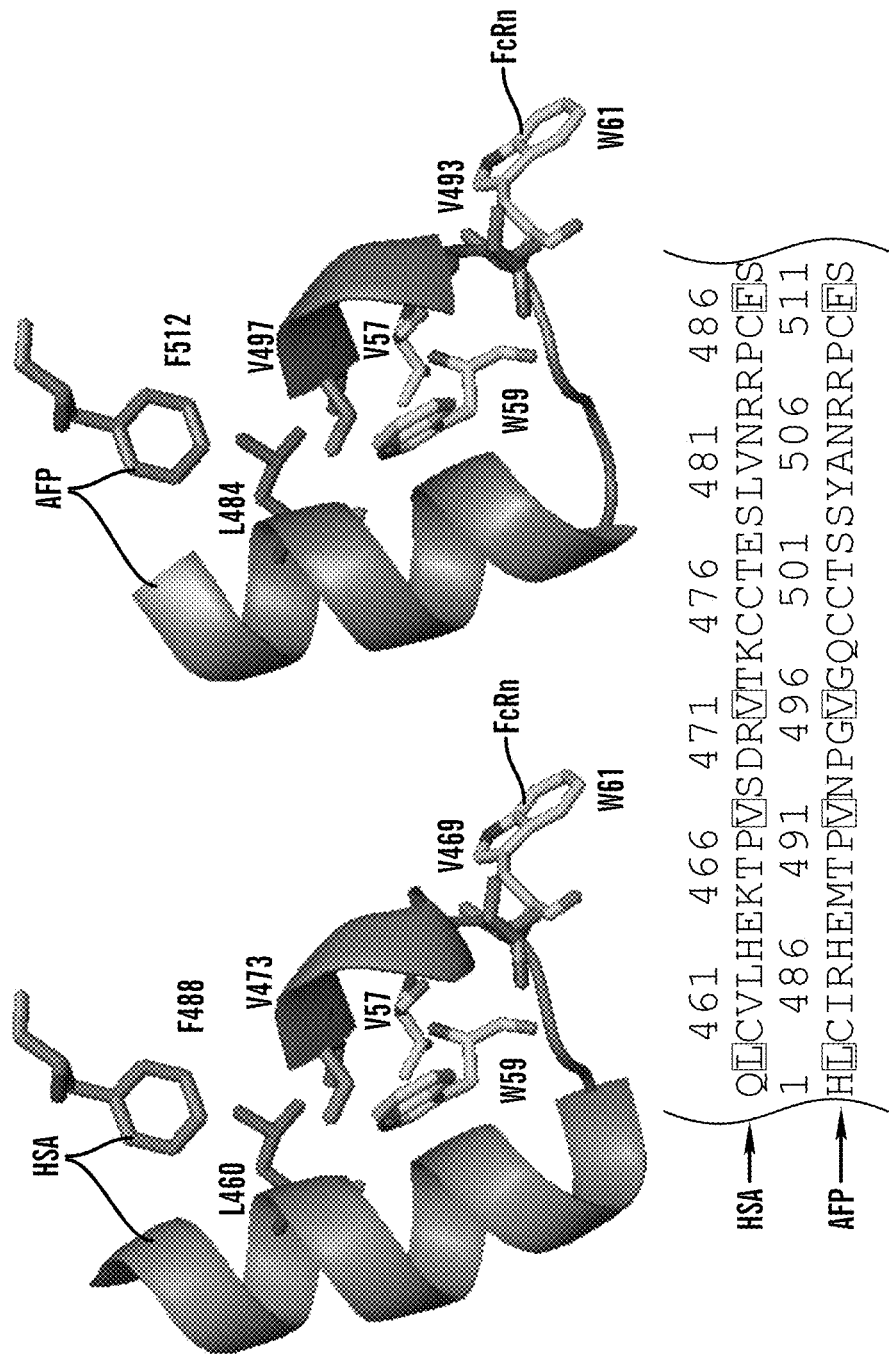
FIG. 17 demonstrates that hydrophobic core centered on HSA L460/V469/V473/F488 is conserved in AFP (L484/V493/V497/F512) and interacts with FcRn V57/W59/W61. HSA/AFP conserved residues in Domain III establish binding to FcRn.

FIG. 17 demonstrates that hydrophobic core centered on HSA L460/V469/V473/F488 is conserved in AFP (L484/V493/V497/F512) and interacts with FcRn V57/W59/W61. HSA/AFP conserved residues in Domain III establish binding to FcRn.

Figure 18:
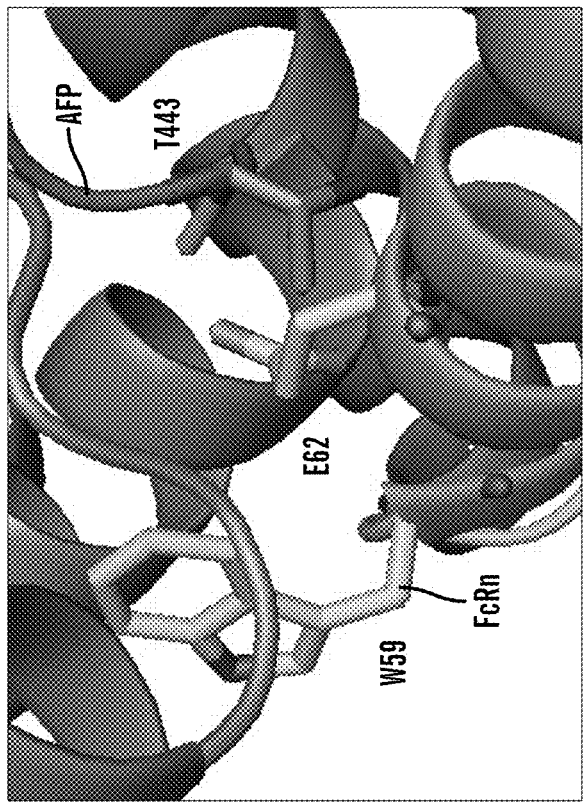
FIG. 18 demonstrates that HSA S419 residue is not conserved in AFP (T443) yet is able to interact with FcRn E62/W59. HSA/AFP non-conserved residues in Domain III preserve AFP binding to FcRn.
Figure 18:
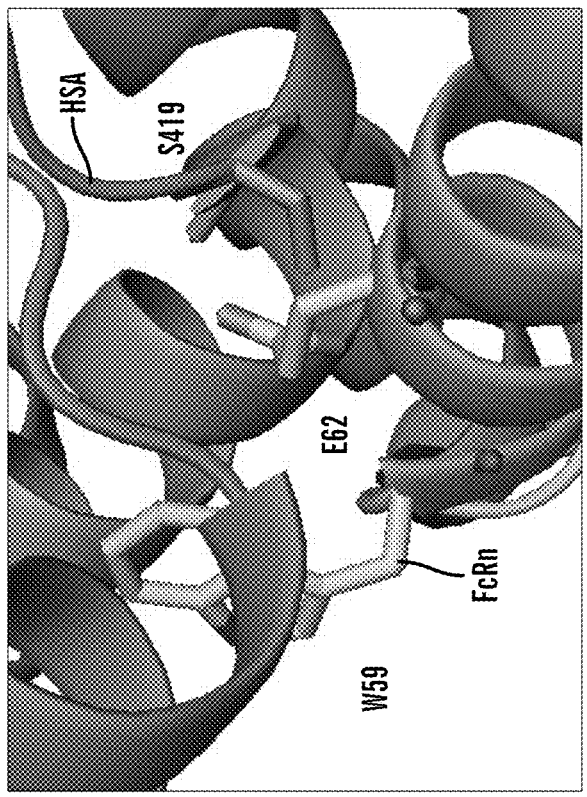

FIG. 18 demonstrates that HSA S419 residue is not conserved in AFP (T443) yet is able to interact with FcRn E62/W59. HSA/AFP non-conserved residues in Domain III preserve AFP binding to FcRn.

Figure 19:
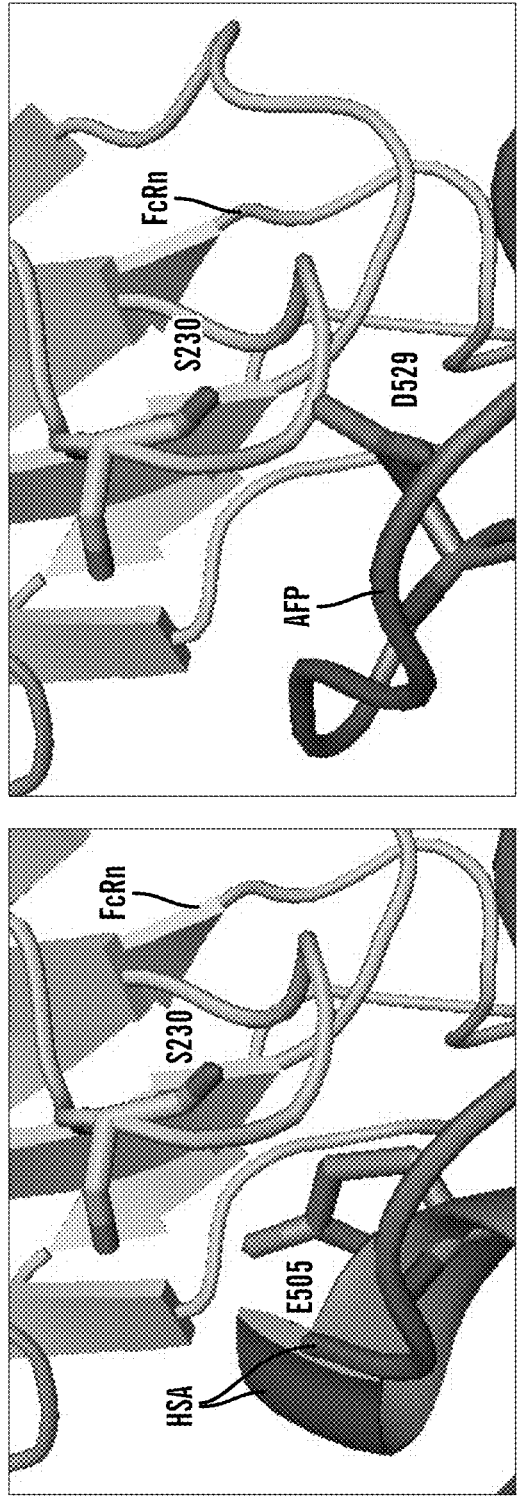
FIG. 19 demonstrates that HSA E505 non-conserved residue in AFP (D529) preserves binding to FcRn S230. HSA/AFP non-conserved residues in Domain III preserve AFP binding to FcRn.

FIG. 19 demonstrates that HSA E505 non-conserved residue in AFP (D529) preserves binding to FcRn S230. HSA/AFP non-conserved residues in Domain III preserve AFP binding to FcRn.

Figure 20:
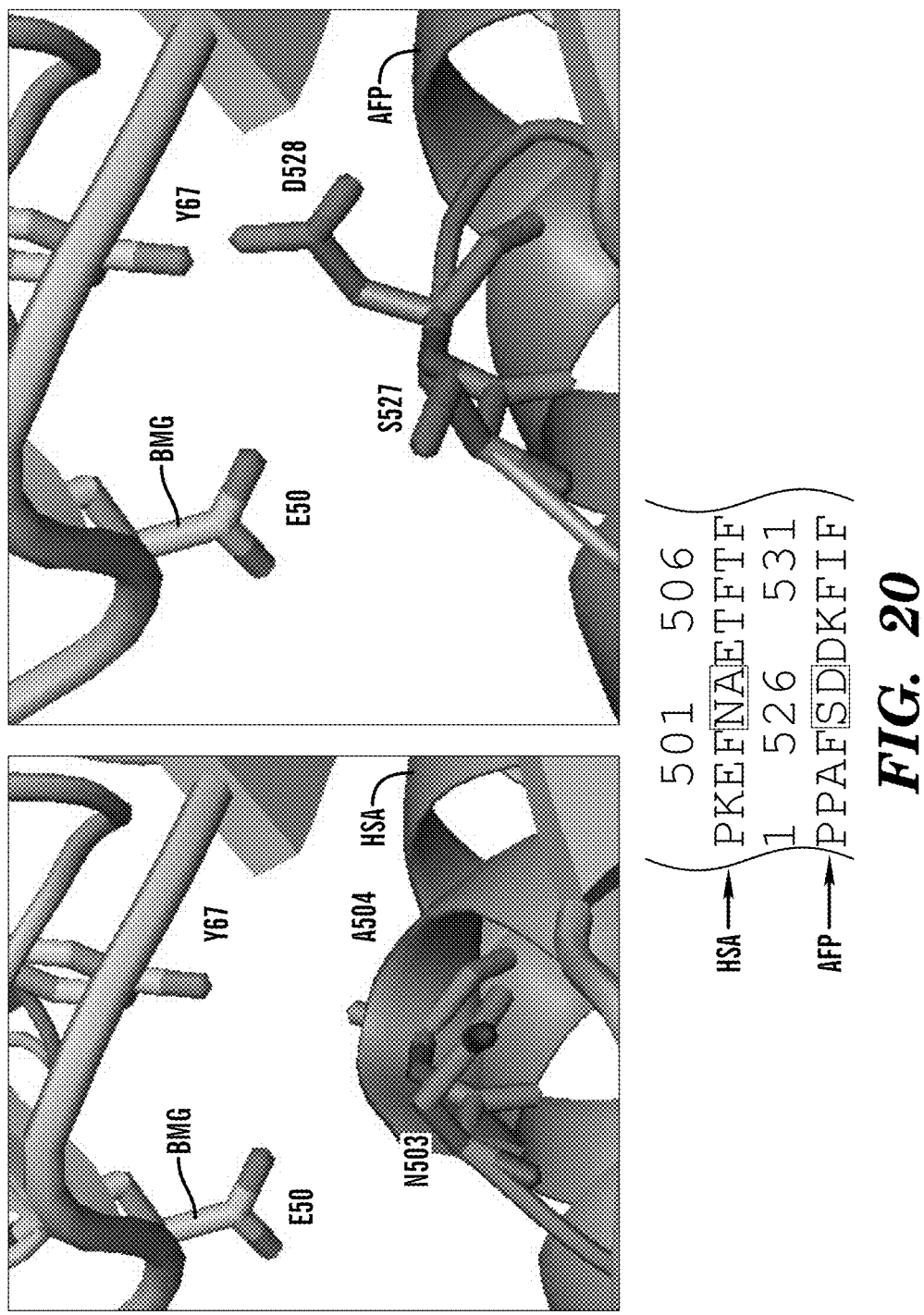
FIG. 20 demonstrates that AFP 5527/D528 residues make contacts with β2m E50 and 67Y that are not present in HSA (N503, A504) providing new interactions. HSA/AFP non-conserved residues that increase AFP binding to FcRn through new contacts with β2m and is not pH dependent.

FIG. 20 demonstrates that AFP S527/D528 residues make contacts with β2m E50 and 67Y that are not present in HSA (N503, A504) providing new interactions. HSA/AFP non-conserved residues that increase AFP binding to FcRn through new contacts with β2m and is not pH dependent.

Figure 21:
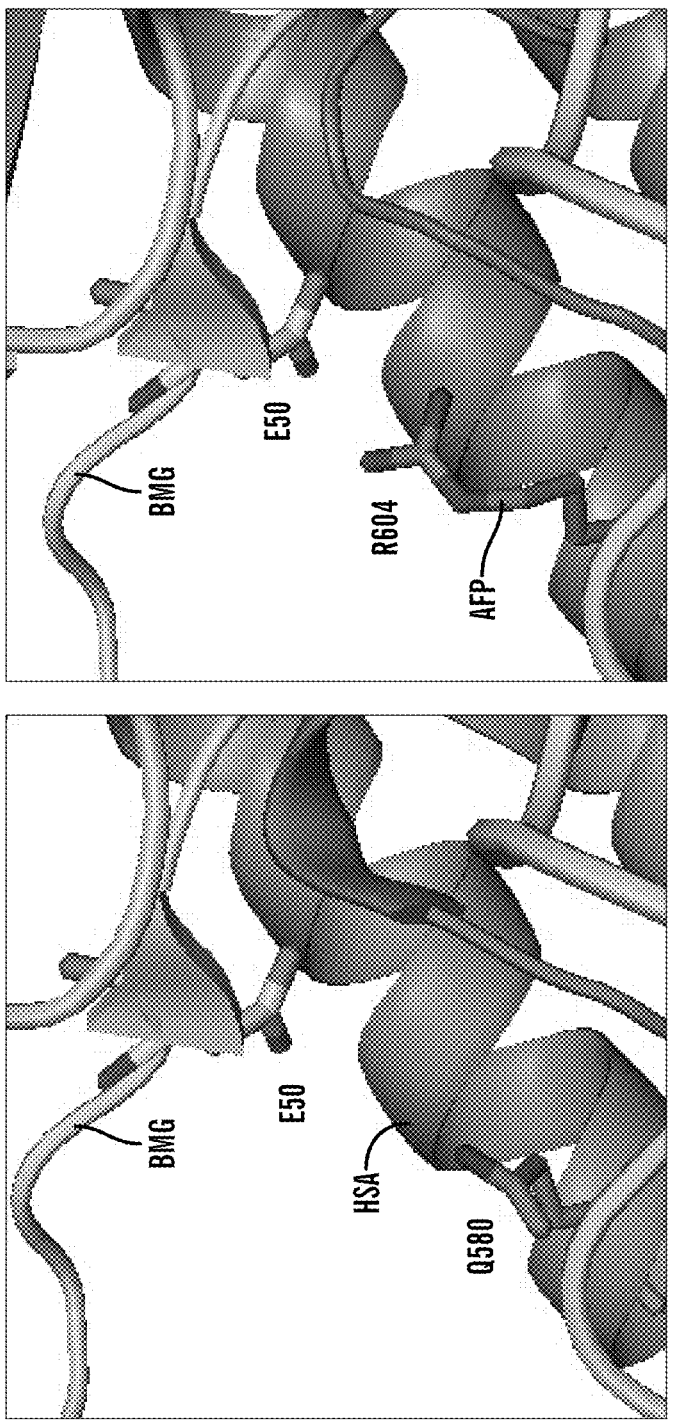
FIG. 21 demonstrates that AFP R604 makes additional contacts with β2m E50, providing new interactions. HSA/AFP non-conserved residues increase AFP binding to β2m. HSA Q580 lacks these interactions.

FIG. 21 demonstrates that AFP R604 makes additional contacts with β2m E50, providing new interactions. HSA/AFP non-conserved residues increase AFP binding to β2m. HSA Q580 lacks these interactions.

Figure 22:
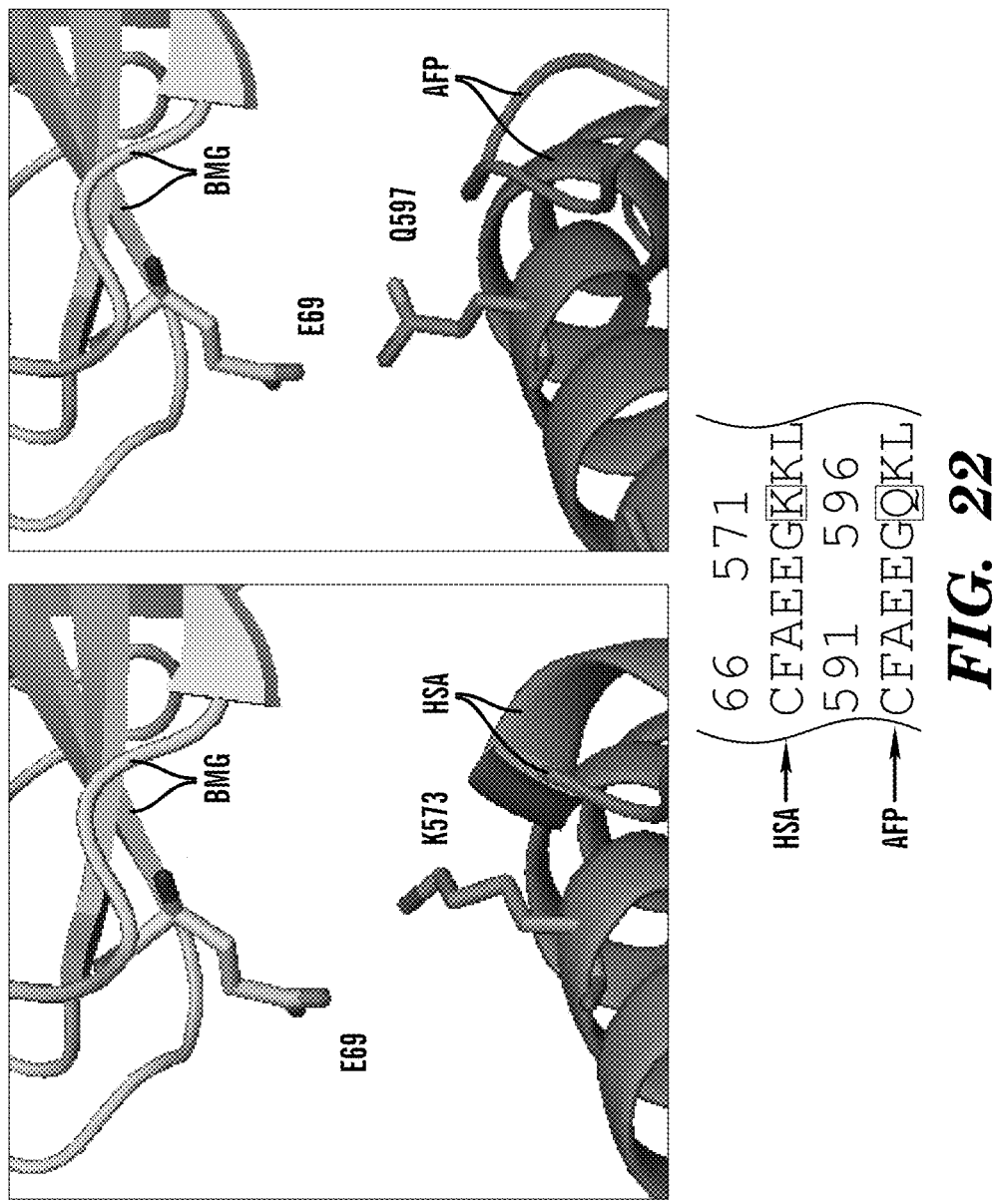
FIG. 22 demonstrates that AFP Q597 residue is better positioned to make contacts with β2m E69 providing stronger interaction. HSA/AFP non-conserved residues establish new and increased AFP-β2m interactions. HSA K573 lacks these interactions.

FIG. 22 demonstrates that AFP Q597 residue is better positioned to make contacts with β2m E69 providing stronger interaction. HSA/AFP non-conserved residues establish new and increased AFP-β2m interactions. HSA K573 lacks these interactions.

Figure 23:
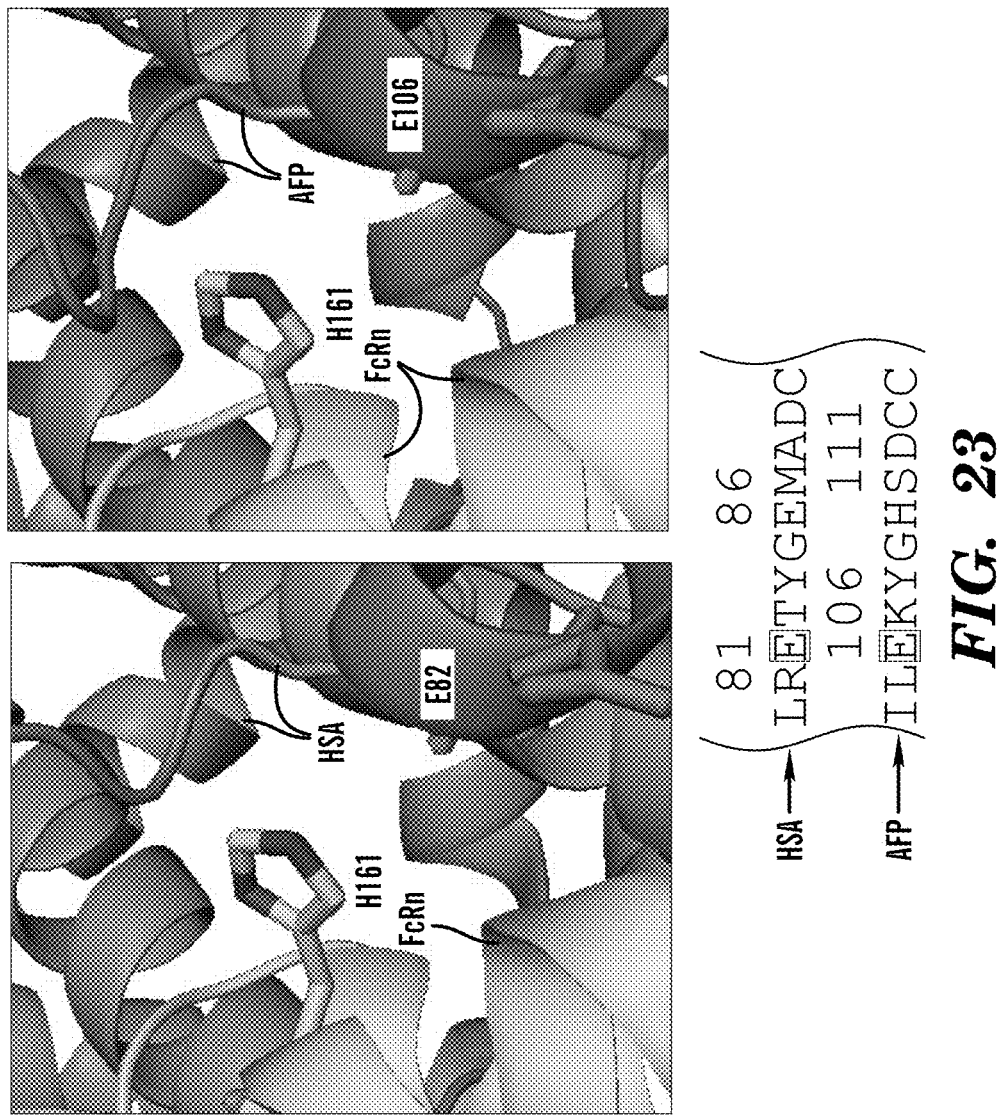
FIG. 23 demonstrates that AFP (E106) conserved residue (with HSA E82) makes long range interaction with FcRn H161. Conserved HSA/AFP residues in Domain that interact with FcRn.

FIG. 23 demonstrates that AFP (E106) conserved residue (with HSA E82) makes long range interaction with FcRn H161. Conserved HSA/AFP residues in Domain I interact with FcRn.

Figure 24:
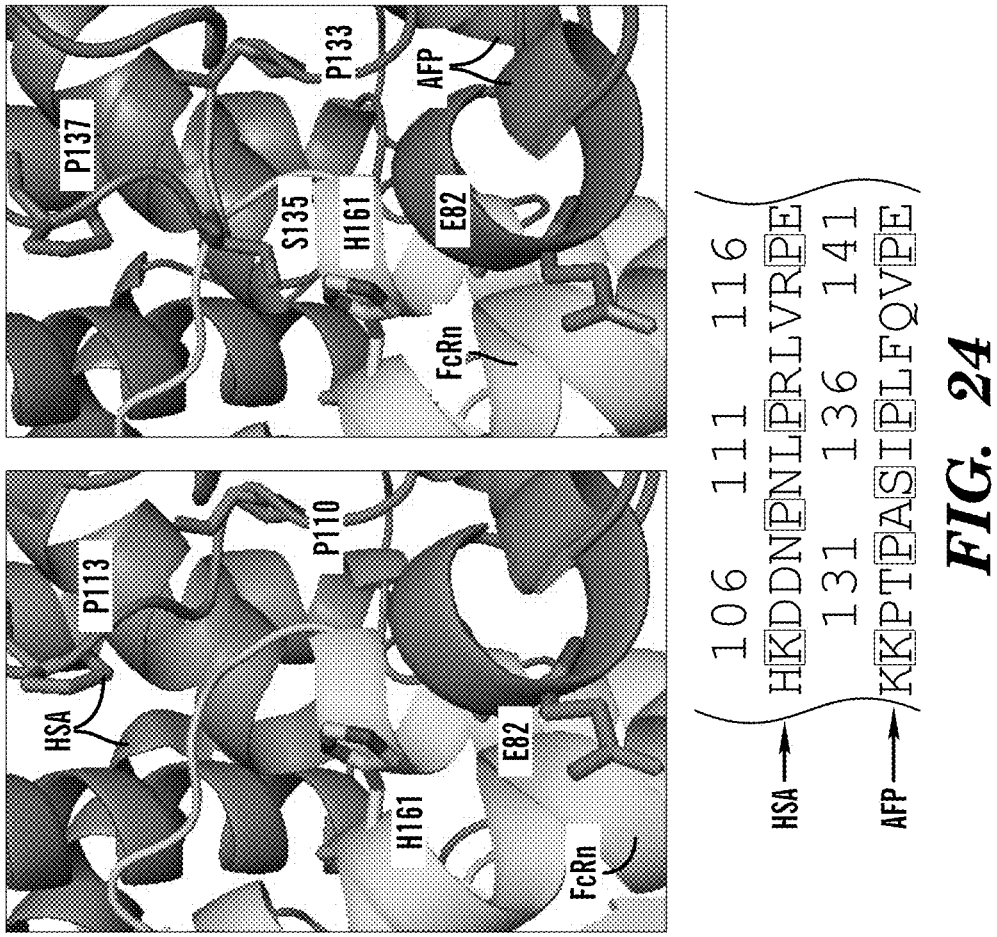
FIG. 24 demonstrates that AFP S135 allows AFP interface to come closer to FcRn and makes ~3 Å interactions with FcRn H161, which is absent in HSA. AFP Domain I-FcRn interaction indicates neutral pH binding. Nearby conserved proline in HSA/AFP occupy same space in interface.
Figure 25:
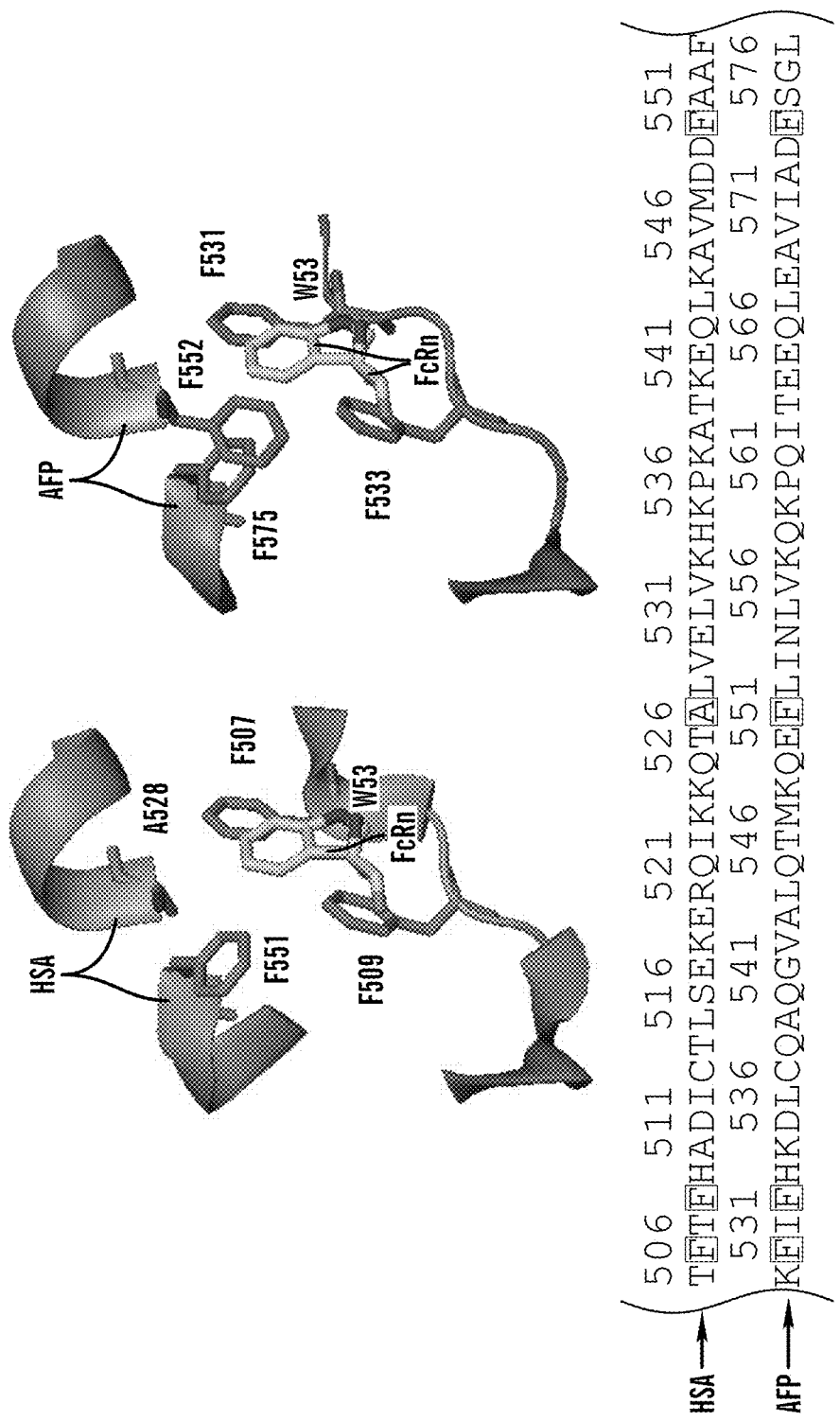
FIG. 25 demonstrates that a substantially conserved hydrophobic core in AFP (F531/F533/F552/F575) centered on FcRn W53: AFP F552 results in stronger AFP-FcRn interactions than HSA A528. AFP-FcRn interactions are consistent with neutral pH binding. AFP (F531/F533/F552/F575) vs HSA (F507/F509/A528/F551)

FIG. 24 demonstrates that AFP S135 allows AFP interface to come closer to FcRn and makes ~3 Å interactions with FcRn H161, which is absent in HSA. AFP Domain I-FcRn interaction suggests neutral pH binding. Nearby conserved proline in HSA/AFP occupy same space in interface.

FIG. 25 demonstrates a larger hydrophobic core in AFP (F531/F533/F552/F575) centered on FcRn W53: AFP F552 results in stronger AFP-FcRn interactions than HSA A528. AFP-FcRn interactions indicates neutral pH binding. AFP (F531/F533/F552/F575) versus HSA (F507/F509/A528/F551).

TABLE 1

SUMMARY OF INTERACTIONS OF AFP WITH FCRN

| HSA Residues | AFP Residues | FcRn Contact Residues | Interaction change |
|---|---|---|---|
| HSA/AFP Conserved Interactions with FcRn | | | |
| Y497 | Y521 | R42 | = |
| V498 | V522 | | |
| P468 | P492 | R69 | = |
| Q417 | Q441 | E44 | = |
| V469 | V493 | | |
| H464 | H488 | | |
| H510 | H534 | N173 | = |
| E565 | E589 | | |
| L460 | L484 | V57 | = |
| V469 | V493 | W59 | |
| V473 | V497 | W61 | |
| F488 | F512 | | |
| D89 | D112 | N149 | = |
| E82 | E106 | H161 | = |
| S419 | T443 | E62, W59 | = |
| E505 | D529 | S230 | = |
| Novel AFP Interactions With FcRn | | | |
| — | S135 | H161 | ↑ Binding |
| F507 | F531 | W53 | ↑ Binding |
| F509 | F533 | | |
| F551 | F575 | | |
| A528 | F552 | | |
| P421 | S445 | Q56 | ↑ Binding |
| Novel AFP Interactions with Beta-2-Microglobulin | | | |
| HSA Residues | AFP Residues | $\beta_2$-Microglobulin Residues | |
| N503 | S527 | E50 | ↑ Binding |
| A504 | D528 | Y67 | |
| Q580 | R604 | | |
| K573 | Q597 | E69 | ↑ Binding |

What is claimed is:

1. A method to inhibit or reduce FcRn and alpha-fetoprotein (AFP) interactions in a disease or disorder associated with elevated AFP levels comprising administering to a subject in need thereof a therapeutically effective amount of a pharmaceutical composition comprising an inhibitor of AFP-FcRn and a pharmaceutically acceptable carrier, wherein said inhibitor of AFP-FcRn inhibits binding between alpha-fetoprotein (AFP) and FcRn, wherein the inhibitor of AFP-FcRn inhibits or blocks the AFP binding site on FcRn, wherein the inhibitor of AFP-FcRn is an antibody or antigen-binding fragment thereof, wherein the inhibitor of AFP-FcRn is an anti-FcRn ADM31 antibody, and wherein the subject has or has been diagnosed with cancer.

2. The method of claim 1, wherein the antibody or antigen-binding fragment thereof is a chimeric, humanized, or completely human antibody or antigen-binding fragment thereof.

3. The method of claim 1, wherein the inhibitor of AFP-FcRn inhibits binding between Y521 and/or V522 of AFP and R42 of FcRn.

4. The method of claim 1, wherein the inhibitor of AFP-FcRn inhibits binding between P492 of AFP and R69 of FcRn.

5. The method of claim 1, wherein the inhibitor of AFP-FcRn inhibits binding between Q441 and/or V493 of AFP and E44 of FcRn.

6. The method of claim 1, wherein the inhibitor of AFP-FcRn inhibits binding between H534 and/or E589 of AFP and N173 of FcRn.

7. The method of claim 1, wherein the inhibitor of AFP-FcRn inhibits binding between the hydrophobic core of AFP and FcRn.

8. The method of claim 1, wherein the inhibitor of AFP-FcRn inhibits binding between L484, V493, V497, and/or F512 of AFP and V57, W59, and/or W61 of FcRn.

9. The method of claim 1, wherein the inhibitor of AFP-FcRn inhibits binding between T443 of AFP and E62 and/or W59 of FcRn.

10. The method of claim 1, wherein the inhibitor of AFP-FcRn inhibits binding between D529 of AFP and S230 of FcRn.

11. The method of claim 1, wherein the inhibitor of AFP-FcRn inhibits binding between S527 and/or D528 of AFP and E50 and/or 67Y of β2m complexed with FcRn.

12. The method of claim 1, wherein the inhibitor of AFP-FcRn inhibits binding between R604 of AFP and the carbonyl oxygen at E50 of β2m complexed with FcRn.

13. The method of claim 1, wherein the inhibitor of AFP-FcRn inhibits binding between Q597 of AFP and E69 of β2m complexed with FcRn.

14. The method of claim 1, wherein the inhibitor of AFP-FcRn inhibits binding between E106 of AFP and H161 of FcRn.

15. The method of claim 1, wherein the inhibitor of AFP-FcRn inhibits binding between S135 of AFP and H161 of FcRn.

16. The method of claim 1, wherein the inhibitor of AFP-FcRn inhibits binding between F531, F533, F552, and/or F575 of AFP and W53 of FcRn.

17. The method of claim 1, further comprising administering an anticancer therapy or agent to the subject.

18. The method of claim 1, wherein the subject has or has been diagnosed with a cancer or tumor of primitive origin, a tumor of liver origin, a hepatoma, a tumor of biliary origin, cholangiocarcinoma, stomach cancer, pancreatic cancer, or a teratocarcinoma.

19. A method to inhibit or reduce FcRn and alpha-fetoprotein (AFP) interactions in a disease or disorder associated with elevated AFP levels comprising administering to a subject in need thereof a therapeutically effective amount of a pharmaceutical composition comprising an inhibitor of AFP-FcRn and a pharmaceutically acceptable carrier, wherein said inhibitor of AFP-FcRn inhibits binding between alpha-fetoprotein (AFP) and FcRn, wherein the inhibitor of AFP-FcRn inhibits or blocks the AFP binding site on FcRn, wherein the inhibitor of AFP-FcRn is an antibody or antigen-binding fragment thereof, wherein the inhibitor of AFP-FcRn is a chimeric anti-FcRn ADM31 antibody or a humanized anti-FcRn ADM31 antibody, and wherein the subject has or has been diagnosed with cancer.

* * * * *

SEQUENCE LISTING

```
<160> NUMBER OF SEQ ID NOS: 31

<210> SEQ ID NO 1
<211> LENGTH: 365
<212> TYPE: PRT
<213> ORGANISM: Homo sapiens

<400> SEQUENCE: 1

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80
```

```
Ser Trp Tyr Trp Glu Lys Glu Thr Thr Asp Leu Arg Ile Lys Glu Lys
                    85                  90                  95

Leu Phe Leu Glu Ala Phe Lys Ala Leu Gly Lys Gly Pro Tyr Thr
            100                 105                 110

Leu Gln Gly Leu Leu Gly Cys Glu Leu Gly Pro Asp Asn Thr Ser Val
            115                 120                 125

Pro Thr Ala Lys Phe Ala Leu Asn Gly Glu Glu Phe Met Asn Phe Asp
            130                 135                 140

Leu Lys Gln Gly Thr Trp Gly Gly Asp Trp Pro Glu Ala Leu Ala Ile
145                 150                 155                 160

Ser Gln Arg Trp Gln Gln Gln Asp Lys Ala Ala Asn Lys Glu Leu Thr
            165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
            195                 200                 205

Ala Arg Pro Ser Ser Pro Gly Phe Ser Val Leu Thr Cys Ser Ala Phe
            210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
            245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
            275                 280                 285

Glu Leu Glu Ser Pro Ala Lys Ser Ser Val Leu Val Val Gly Ile Val
            290                 295                 300

Ile Gly Val Leu Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
            325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
            355                 360                 365

<210> SEQ ID NO 2
<211> LENGTH: 119
<212> TYPE: PRT
<213> ORGANISM: Homo sapiens

<400> SEQUENCE: 2

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
            35                  40                  45

Gly Phe His Pro Ser Asp Ile Glu Val Asp Leu Leu Lys Asn Gly Glu
            50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
```

```
                85                   90                   95
Glu Tyr Ala Cys Arg Val Asn His Val Thr Leu Ser Gln Pro Lys Ile
            100                 105                 110

Val Lys Trp Asp Arg Asp Met
            115

<210> SEQ ID NO 3
<211> LENGTH: 609
<212> TYPE: PRT
<213> ORGANISM: Homo sapiens

<400> SEQUENCE: 3

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
    130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
    210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
        275                 280                 285

Cys Ser Gln Gln Asp Thr Leu Ser Asn Lys Ile Thr Glu Cys Cys Lys
    290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335
```

```
Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
        355                 360                 365

Val Ile Leu Arg Val Ala Lys Gly Tyr Gln Glu Leu Leu Glu Lys Cys
    370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
        435                 440                 445

Ala Ile Thr Arg Lys Met Ala Ala Thr Ala Ala Thr Cys Cys Gln Leu
    450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
                485                 490                 495

Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
        515                 520                 525

Asp Lys Phe Ile Phe His Lys Asp Leu Cys Gln Ala Gln Gly Val Ala
    530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
                565                 570                 575

Gly Leu Leu Glu Lys Cys Cys Gln Gly Gln Glu Gln Glu Val Cys Phe
            580                 585                 590

Ala Glu Glu Gly Gln Lys Leu Ile Ser Lys Thr Arg Ala Ala Leu Gly
        595                 600                 605

Val

<210> SEQ ID NO 4
<211> LENGTH: 575
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80
```

```
Glu Gln Ser Ser Gly Cys Leu Glu Asn Gln Leu Pro Ala Phe Leu Glu
                    85                  90                  95
Glu Leu Cys His Glu Lys Glu Ile Leu Glu Lys Tyr Gly His Ser Asp
            100                 105                 110
Cys Cys Ser Gln Ser Glu Glu Gly Arg His Asn Cys Phe Leu Ala His
            115                 120                 125
Lys Lys Pro Thr Pro Ala Ser Ile Pro Leu Phe Gln Val Pro Glu Pro
        130                 135                 140
Val Thr Ser Cys Glu Ala Tyr Glu Glu Asp Arg Glu Thr Phe Met Asn
145                 150                 155                 160
Lys Phe Ile Tyr Glu Ile Ala Arg Arg His Pro Phe Leu Tyr Ala Pro
                165                 170                 175
Thr Ile Leu Leu Trp Ala Ala Arg Tyr Asp Lys Ile Ile Pro Ser Cys
            180                 185                 190
Cys Lys Ala Glu Asn Ala Val Glu Cys Phe Gln Thr Lys Ala Ala Thr
        195                 200                 205
Val Thr Lys Glu Leu Arg Glu Ser Ser Leu Leu Asn Gln His Ala Cys
210                 215                 220
Ala Val Met Lys Asn Phe Gly Thr Arg Thr Phe Gln Ala Ile Thr Val
225                 230                 235                 240
Thr Lys Leu Ser Gln Lys Phe Thr Lys Val Asn Phe Thr Glu Ile Gln
                245                 250                 255
Lys Leu Val Leu Asp Val Ala His Val His Glu His Cys Cys Arg Gly
            260                 265                 270
Asp Val Leu Asp Cys Leu Gln Asp Gly Glu Lys Ile Met Ser Tyr Ile
        275                 280                 285
Cys Ser Gln Gln Asp Thr Leu Ser Asn Lys Ile Thr Glu Cys Cys Lys
        290                 295                 300
Leu Thr Thr Leu Glu Arg Gly Gln Cys Ile Ile His Ala Glu Asn Asp
305                 310                 315                 320
Glu Lys Pro Glu Gly Leu Ser Pro Asn Leu Asn Arg Phe Leu Gly Asp
                325                 330                 335
Arg Asp Phe Asn Gln Phe Ser Ser Gly Glu Lys Asn Ile Phe Leu Ala
            340                 345                 350
Ser Phe Val His Glu Tyr Ser Arg Arg His Pro Gln Leu Ala Val Ser
        355                 360                 365
Val Ile Leu Arg Val Ala Lys Gly Tyr Gln Glu Leu Leu Glu Lys Cys
        370                 375                 380
Phe Gln Thr Glu Asn Pro Leu Glu Cys Gln Asp Lys Gly Glu Glu Glu
385                 390                 395                 400
Leu Gln Lys Tyr Ile Gln Glu Ser Gln Ala Leu Ala Lys Arg Ser Cys
                405                 410                 415
Gly Leu Phe Gln Lys Leu Gly Glu Tyr Tyr Leu Gln Asn Ala Phe Leu
            420                 425                 430
Val Ala Tyr Thr Lys Lys Ala Pro Gln Leu Thr Ser Ser Glu Leu Met
        435                 440                 445
Ala Ile Thr Arg Lys Met Ala Ala Thr Ala Ala Thr Cys Cys Gln Leu
450                 455                 460
Ser Glu Asp Lys Leu Leu Ala Cys Gly Glu Gly Ala Ala Asp Ile Ile
465                 470                 475                 480
Ile Gly His Leu Cys Ile Arg His Glu Met Thr Pro Val Asn Pro Gly
                485                 490                 495
Val Gly Gln Cys Cys Thr Ser Ser Tyr Ala Asn Arg Arg Pro Cys Phe
```

```
                500             505             510
Ser Ser Leu Val Val Asp Glu Thr Tyr Val Pro Pro Ala Phe Ser Asp
        515                 520                 525

Asp Lys Phe Ile Phe His Lys Asp Leu Cys Gln Ala Gln Gly Val Ala
        530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe
            565                 570                 575
```

<210> SEQ ID NO 5
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Leu Cys Ile Arg His Glu Met Thr Pro Val Asn Pro Gly Val Gly Gln
1               5                   10                  15

Cys Cys Thr Ser Ser Tyr Ala Asn Arg Arg Pro Cys Phe Ser Ser Leu
            20                  25                  30

Val Val Asp Glu Thr Tyr Val Pro Pro Ala Phe Ser Asp Asp Lys Phe
        35                  40                  45

Ile Phe His Lys Asp Leu Cys Gln Ala Gln Gly Val Ala Leu Gln Thr
    50                  55                  60

Met Lys Gln Glu Phe Leu Ile Asn Leu Val Lys Gln Lys Pro Gln Ile
65                  70                  75                  80

Thr Glu Glu Gln Leu Glu Ala Val Ile Ala Asp Phe
                85                  90
```

<210> SEQ ID NO 6
<211> LENGTH: 15
<212> TYPE: PRT
<213> ORGANISM: Homo sapiens

<400> SEQUENCE: 6

```
Leu Glu Val Asp Glu Thr Tyr Val Pro Lys Glu Phe Asn Ala Glu
1               5                   10                  15
```

<210> SEQ ID NO 7
<211> LENGTH: 15
<212> TYPE: PRT
<213> ORGANISM: Homo sapiens

<400> SEQUENCE: 7

```
Leu Val Val Asp Glu Thr Tyr Val Pro Pro Ala Phe Ser Asp Asp
1               5                   10                  15
```

<210> SEQ ID NO 8
<211> LENGTH: 7
<212> TYPE: PRT
<213> ORGANISM: Homo sapiens

<400> SEQUENCE: 8

```
Glu Lys Thr Pro Val Ser Asp
1               5
```

<210> SEQ ID NO 9
<211> LENGTH: 7

```
<212> TYPE: PRT
<213> ORGANISM: Homo sapiens

<400> SEQUENCE: 9

Glu Met Thr Pro Val Asn Pro
1               5

<210> SEQ ID NO 10
<211> LENGTH: 54
<212> TYPE: PRT
<213> ORGANISM: Homo sapiens

<400> SEQUENCE: 10

Pro Gln Val Ser Thr Pro Thr Leu Val Glu Val Ser Arg Asn Leu Gly
1               5                   10                  15

Lys Val Gly Ser Lys Cys Cys Lys His Pro Glu Ala Lys Arg Met Pro
                20                  25                  30

Cys Ala Glu Asp Tyr Leu Ser Val Val Leu Asn Gln Leu Cys Val Leu
            35                  40                  45

His Glu Lys Thr Pro Val
    50

<210> SEQ ID NO 11
<211> LENGTH: 54
<212> TYPE: PRT
<213> ORGANISM: Homo sapiens

<400> SEQUENCE: 11

Pro Gln Leu Thr Ser Ser Glu Leu Met Ala Ile Thr Arg Lys Met Ala
1               5                   10                  15

Ala Thr Ala Ala Thr Cys Cys Gln Leu Ser Glu Asp Lys Leu Leu Ala
                20                  25                  30

Cys Gly Glu Gly Ala Ala Asp Ile Ile Ile Gly His Leu Cys Ile Arg
            35                  40                  45

His Glu Met Thr Pro Val
    50

<210> SEQ ID NO 12
<211> LENGTH: 58
<212> TYPE: PRT
<213> ORGANISM: Homo sapiens

<400> SEQUENCE: 12

Phe His Ala Asp Ile Cys Thr Leu Ser Glu Lys Glu Arg Gln Ile Lys
1               5                   10                  15

Lys Gln Thr Ala Leu Val Glu Leu Val Lys His Lys Pro Lys Ala Thr
                20                  25                  30

Lys Glu Gln Leu Lys Ala Val Met Asp Asp Phe Ala Ala Phe Val Glu
            35                  40                  45

Lys Cys Cys Lys Ala Asp Asp Lys Glu Thr
    50                  55

<210> SEQ ID NO 13
<211> LENGTH: 58
<212> TYPE: PRT
<213> ORGANISM: Homo sapiens

<400> SEQUENCE: 13

Phe His Lys Asp Leu Cys Gln Ala Gln Gly Val Ala Leu Gln Thr Met
1               5                   10                  15
```

```
Lys Gln Glu Phe Leu Ile Asn Leu Val Lys Gln Lys Pro Gln Ile Thr
                20                  25                  30

Glu Glu Gln Leu Glu Ala Val Ile Ala Asp Phe Ser Gly Leu Leu Glu
            35                  40                  45

Lys Cys Cys Gln Gly Gln Glu Gln Glu Val
        50                  55

<210> SEQ ID NO 14
<211> LENGTH: 31
<212> TYPE: PRT
<213> ORGANISM: Homo sapiens

<400> SEQUENCE: 14

Gln Leu Cys Val Leu His Glu Lys Thr Pro Val Ser Asp Arg Val Thr
1               5                   10                  15

Lys Cys Cys Thr Glu Ser Leu Val Asn Arg Arg Pro Cys Phe Ser
                20                  25                  30

<210> SEQ ID NO 15
<211> LENGTH: 31
<212> TYPE: PRT
<213> ORGANISM: Homo sapiens

<400> SEQUENCE: 15

His Leu Cys Ile Arg His Glu Met Thr Pro Val Asn Pro Gly Val Gly
1               5                   10                  15

Gln Cys Cys Thr Ser Ser Tyr Ala Asn Arg Arg Pro Cys Phe Ser
                20                  25                  30

<210> SEQ ID NO 16
<211> LENGTH: 11
<212> TYPE: PRT
<213> ORGANISM: Homo sapiens

<400> SEQUENCE: 16

Lys Lys Val Pro Gln Val Ser Thr Pro Thr Leu
1               5                   10

<210> SEQ ID NO 17
<211> LENGTH: 11
<212> TYPE: PRT
<213> ORGANISM: Homo sapiens

<400> SEQUENCE: 17

Lys Lys Ala Pro Gln Leu Thr Ser Ser Glu Leu
1               5                   10

<210> SEQ ID NO 18
<211> LENGTH: 11
<212> TYPE: PRT
<213> ORGANISM: Homo sapiens

<400> SEQUENCE: 18

Glu Phe Asn Ala Glu Thr Phe Thr Phe His Ala
1               5                   10

<210> SEQ ID NO 19
<211> LENGTH: 11
<212> TYPE: PRT
<213> ORGANISM: Homo sapiens

<400> SEQUENCE: 19

Ala Phe Ser Asp Asp Lys Phe Ile Phe His Lys
```

```
<210> SEQ ID NO 20
<211> LENGTH: 11
<212> TYPE: PRT
<213> ORGANISM: Homo sapiens

<400> SEQUENCE: 20

Pro Lys Glu Phe Asn Ala Glu Thr Phe Thr Phe
1               5                   10

<210> SEQ ID NO 21
<211> LENGTH: 11
<212> TYPE: PRT
<213> ORGANISM: Homo sapiens

<400> SEQUENCE: 21

Pro Pro Ala Phe Ser Asp Asp Lys Phe Ile Phe
1               5                   10

<210> SEQ ID NO 22
<211> LENGTH: 11
<212> TYPE: PRT
<213> ORGANISM: Homo sapiens

<400> SEQUENCE: 22

Lys Leu Val Ala Ala Ser Gln Ala Ala Leu Gly
1               5                   10

<210> SEQ ID NO 23
<211> LENGTH: 11
<212> TYPE: PRT
<213> ORGANISM: Homo sapiens

<400> SEQUENCE: 23

Lys Leu Ile Ser Lys Thr Arg Ala Ala Leu Gly
1               5                   10

<210> SEQ ID NO 24
<211> LENGTH: 9
<212> TYPE: PRT
<213> ORGANISM: Homo sapiens

<400> SEQUENCE: 24

Cys Phe Ala Glu Glu Gly Lys Lys Leu
1               5

<210> SEQ ID NO 25
<211> LENGTH: 9
<212> TYPE: PRT
<213> ORGANISM: Homo sapiens

<400> SEQUENCE: 25

Cys Phe Ala Glu Glu Gly Gln Lys Leu
1               5

<210> SEQ ID NO 26
<211> LENGTH: 11
<212> TYPE: PRT
<213> ORGANISM: Homo sapiens

<400> SEQUENCE: 26

Leu Arg Glu Thr Tyr Gly Glu Met Ala Asp Cys
1               5                   10
```

```
<210> SEQ ID NO 27
<211> LENGTH: 11
<212> TYPE: PRT
<213> ORGANISM: Homo sapiens

<400> SEQUENCE: 27

Ile Leu Glu Lys Tyr Gly His Ser Asp Cys Cys
1               5                   10

<210> SEQ ID NO 28
<211> LENGTH: 15
<212> TYPE: PRT
<213> ORGANISM: Homo sapiens

<400> SEQUENCE: 28

His Lys Asp Asp Asn Pro Asn Leu Pro Arg Leu Val Arg Pro Glu
1               5                   10                  15

<210> SEQ ID NO 29
<211> LENGTH: 15
<212> TYPE: PRT
<213> ORGANISM: Homo sapiens

<400> SEQUENCE: 29

Lys Lys Pro Thr Pro Ala Ser Ile Pro Leu Phe Gln Val Pro Glu
1               5                   10                  15

<210> SEQ ID NO 30
<211> LENGTH: 49
<212> TYPE: PRT
<213> ORGANISM: Homo sapiens

<400> SEQUENCE: 30

Thr Phe Thr Phe His Ala Asp Ile Cys Thr Leu Ser Glu Lys Glu Arg
1               5                   10                  15

Gln Ile Lys Lys Gln Thr Ala Leu Val Glu Leu Val Lys His Lys Pro
            20                  25                  30

Lys Ala Thr Lys Glu Gln Leu Lys Ala Val Met Asp Asp Phe Ala Ala
        35                  40                  45

Phe

<210> SEQ ID NO 31
<211> LENGTH: 49
<212> TYPE: PRT
<213> ORGANISM: Homo sapiens

<400> SEQUENCE: 31

Lys Phe Ile Phe His Lys Asp Leu Cys Gln Ala Gln Gly Val Ala Leu
1               5                   10                  15

Gln Thr Met Lys Gln Glu Phe Leu Ile Asn Leu Val Lys Gln Lys Pro
            20                  25                  30

Gln Ile Thr Glu Glu Gln Leu Glu Ala Val Ile Ala Asp Phe Ser Gly
        35                  40                  45

Leu
```